United States Patent [19]

Crouse et al.

[11] Patent Number: 5,153,316
[45] Date of Patent: Oct. 6, 1992

[54] INTERMEDIATES FOR HERBICIDAL PHENYLIMIDAZOLONES

[76] Inventors: Gary D. Crouse, 1088 N. Shortridge Rd., Indianapolis, Ind. 46219; Michael P. Lynch, 1910 Ridge Dr., Greenfield, Ind. 46140; Jeffery D. Webster, 4444 W. Bittner Ln.; John P. Wright, 4029 S. 700 W., both of New Palestine, Ind. 46163

[21] Appl. No.: 710,223

[22] Filed: Jun. 4, 1991

[51] Int. Cl.$^5$ ............... C07D 211/40; C07D 267/12
[52] U.S. Cl. .................. 540/451; 540/529; 546/221; 548/538
[58] Field of Search .......... 548/538; 546/221; 540/451, 529

[56] References Cited

U.S. PATENT DOCUMENTS 4,977,167 12/1990 Matsumura et al. ............ 548/538

*Primary Examiner*—Bernard Dentz

[57] ABSTRACT

The present invention relates to novel phenylimidazolone compounds of the formula

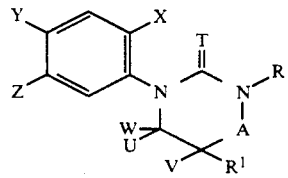

wherein
A is a bond or C=T;
R is —H, Alk, halo-Alk, cyano-Alk, or phenyl;
$R^1$ is —H, Alk, halogen, halo-Alk, —CN; or when A is a bond, R and $R^1$ may together form a saturated, partially saturated, or unsaturated three to seven member carbon ring, and the ring may be substituted at any position independently with one or more Alk, —O—Alk, —CN, halogen, —OH, or =O groups;
T is O or S;
U is —H;
V is —OH, or U and V may together form a bond;
W is halogen or —CN, and when W is halogen, $R^1$ is —CN;
X is —H or halogen;
Y is —H, halogen, —CN, Alk, —CF$_3$, or —OCF$_3$;
Z is —H, halogen, —OH, Alk, aryloxy, C$_{1-6}$ acyl, —NH$_2$, —NO$_2$, —NR$^2$SO$_2$R$^2$, —N(SO$_2$R$^2$)$_2$, —NR$^2$COR$^2$, or B; or Y and Z may together form a saturated, partially saturated, or unsaturated three to seven member carbon ring, wherein each carbon may be independently replaced with N, O, or S, and the ring may be substituted at any position independently with one or more Alk, —O—Alk, =O, —SO$_2$R$^2$, or C$_{1-6}$ acyl groups;
Alk is a straight, branched, or cyclic saturated or unsaturated C$_{1-6}$ hydrocarbon group;
B is —O—Alk, wherein each carbon may be independently replaced with one or more O or S groups, and optionally substituted with one or more halogen or C$_{1-6}$ acyl groups; or the agriculturally acceptable salts, amides, and esters thereof.

The compounds are useful as herbicides.

1 Claim, No Drawings

INTERMEDIATES FOR HERBICIDAL PHENYLIMIDAZOLONES

BACKGROUND OF THE INVENTION

The present invention relates to novel phenylimidazolone derivatives, compositions comprising these derivatives, and their use as herbicides. The present invention further relates to novel intermediates used to make these compounds.

SUMMARY OF THE INVENTION

More particularly, the present invention relates to certain novel phenylimidazolone derivatives represented by Formula A below, as follows:

Formula A

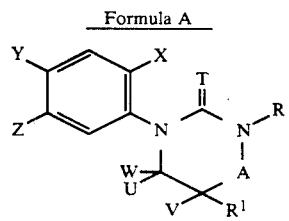

wherein
A is a bond or C=T;
R is —H, Alk, halo-Alk, cyano-Alk, or phenyl;
$R^1$ is —H, Alk, halogen, halo-Alk, or —CN; or when A is a bond, R and $R^1$ may together form a saturated, partially saturated, or unsaturated three to seven member carbon ring, and the ring may be substituted at any position independently with one or more Alk, —O—Alk, —CN, halogen, —OH, or =O groups;
T is O or S;
U is —H;
V is —OH, or U and V may together form a bond;
W is halogen or —CN, and when W is halogen, $R^1$ is —CN;
X is —H or halogen;
Y is —H, halogen, —CN, Alk, —CF$_3$, or —OCF$_3$:
Z is —H, halogen, —OH, Alk, aryloxy, $C_{1-6}$ acyl, —NH$_2$, —NO$_2$, —NR$_2$SO$_2$R$^2$, —N(SO$_2$R$^2$)$_2$, —NR$^2$COR$^2$, or B; or Y and Z may together form a saturated, partially saturated, or unsaturated three to seven member carbon ring, wherein each carbon may be independently replaced with N, O or S, and the ring may be substituted at any position independently with one or more Alk, —O—Alk, =O, —SO$_2$R$^2$, or $C_{1-6}$ acyl groups;
Alk is a straight, branched, or cyclic saturated or unsaturated $C_{1-6}$ hydrocarbon group;
B is —O—Alk, wherein each carbon may be independently replaced with one or more O or S groups, and optionally substituted with one or more halogen or $C_{1-6}$ acyl groups; or
the agriculturally acceptable salts, amides, and esters thereof.

When used herein, the term "halo" or "halogen" includes F, Cl, I, and Br.

When used herein, the term "cyano" includes the —CN group.

When used herein, the term "phenyl", "Ph", or "aryl" includes the $C_6H_5$ group derived from benzene.

When used herein, the term "acyl" includes the

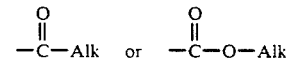

groups.

The term "agriculturally acceptable salts, amides, and esters" includes any salt, amide, or ester of a compound of Formula A which does not substantially negatively affect the herbicidal activity of said compound, or which can be hydrolyzed and/or oxidized in plants or soil to a carboxyl moiety that is in dissociated and/or undissociated form.

Illustrative of the compounds included within the scope of the present invention are the following compounds named below, and their structure as represented in the tables below:

1. 1-(4-Chlorophenyl)-5-chloro-4-cyano-3-propyl-1,3-dihydro-2H-imidazol-2-one.
2. 1-(4-Chlorophenyl)-4,5-dicyano-3-propyl-1,3-dihydro-2H-imidazol-2-one.
3. 1-Phenyl-4,5-dicyano-3-methyl-1,3-dihydro-2H-imidazol-2-one.
4. 1-(4-Chloro-2-fluoro-5-propargyloxyphenyl)-5-chloro-4-cyano-3-methyl -1,3-dihydro-2H-imidazol-2-one.
5. 1-(3,4-Dichlorophenyl)-4,5-dicyano-3-methyl-1,3-dihydro-2H-imidazol-2-one.
6. 1-(4-Methylphenyl)-4,5-dicyano-3-methyl-1,3-dihydro-2H-imidazol-2-one.
7. 1-(4-Chlorophenyl)-4,5-dicyano-3-ethyl-1,3-dihydro-2H-imidazol-2-one.
8. 1-(4-Fluorophenyl)-5-chloro-4-cyano-3-methyl-1,3-dihydro-2H-imidazol-2-one.
9. 1-(4-Trifluoromethylphenyl)-5-chloro-4-cyano-3-methyl-1,3-dihydro-2H-imidazol-2-one.
10. 1-(4-Cyanophenyl)-4,5-dicyano-3-methyl-1,3-dihydro-2H-imidazol-2-one.
11. 1-(4-Trifluoromethoxyphenyl)-5-chloro-4-cyano-3-methyl-1,3-dihydro-2H-imidazol-2-one.
12. 1-(4-Chlorophenyl)-5-chloro-4-cyano-3-phenyl-1,3-dihydro-2H-imidazol-2-one.
13. 1-(4-Chlorophenyl)-5-chloro-4-cyano-3-methyl-1,3-dihydro-2H-imidazol-2-one.
14. 1-(2-Chlorophenyl)-5-chloro-4-cyano-3-methyl-1,3-dihydro-2H-imidazol-2-one.
15. 1-(3,4-Dichlorophenyl)-5-chloro-4-cyano-3-methyl-1,3-dihydro-2H-imidazol-2-one.
16. 1-(4-Methylphenyl)-5-chloro-4-cyano-3-methyl-1,3-dihydro-2H-imidazol-2-one.
17. 1-(4-Chlorophenyl)-4,5-dicyano-3-methyl-1,3-dihydro-2H-imidazol-2-one.
18. 1-(2,4-Dichloro-5-methylethoxyphenyl)-5-chloro-4-cyano-3-methyl-1,3-dihydro -2H-imidazol-2-one.
19. 5-Chloro-4-cyano-3-methyl-1-phenyl-1,3-dihydro-2H-imidazol-2-one.
20. 1-(4-Chloro-2-fluoro-5-propargyloxyphenyl)-4,5-dicyano-3-methyl-1,3-dihydro-2H-imidazol-2-one.
21. 1-(4-Chlorophenyl)-4,5-dicyano-3-phenyl-1,3-dihydro-2H-imidazol-2-one.
22. 1-(4-Chlorophenyl)-5-chloro-4-cyano-3-ethyl-1,3-dihydro-2H-imidazol-2-one.
23. 1-(4-Bromo-2-fluoro-5-propargyloxyphenyl)-5-chloro-4-cyano-3-methyl-1,3-dihydro-2H-imidazol-2-one.
24. 1-(4-Chloro-2-fluoro-5-propargyloxyphenyl)-5-chloro-4-cyano-3-ethyl-1,3-dihydro-2H-imidazol-2-one.

25. 1-(4-Chloro-2-fluoro-5-(1-ethoxycarbonylethoxy)phenyl)-4,5-dicyano-3-methyl-1,3-dihydro-2H-imidazol-2-one.
26. 1-(4-Bromophenyl)-4,5-dicyano-3-ethyl-1,3-dihydro-2H-imidazol-2-one.
27. 1-(2,4-Dichlorophenyl)-4,5-dicyano-3-methyl-1,3-dihydro-2H-imidazol-2-one.
28. 1-(4-Bromophenyl)-5-chloro-4-cyano-3-ethyl-1,3-dihydro-2H-imidazol-2-one.
29. 1-(4-Bromo-2-fluoro-5-methoxyphenyl)-4,5-dicyano-3-methyl-1,3-dihydro-2H-imidazol-2-one.
30. 1-(4-Chloro-2-fluoro-5-propargyloxyphenyl)-5-chloro-4-cyano-3-propyl-1,3-dihydro-2H-imidazol-2-one.
31. 1-(4-Chloro-2-fluloxyphenyl)-4,5-dicyano-3-propyl-1,3-dihydro-2H-imidazol-2-one.
32. 1-(4-Chloro-2-fluoro-5-(1-ethoxycarbonylethoxy)phenyl)-4,5-dicyano-3-propyl-1,3-dihydro-2H-imidazol-2-one.
33. 1-(4-Chloro-2-fluoro-5-methoxyphenyl)-4,5-dicyano-3-methyl-1,3-dihydro-2H-imidazol-2-one.
34. 1-(4-Chloro-2-fluoro-5-hydroxyphenyl)-4,5-dicyano-3-methyl-1,3-dihydro-2H-imidazol-2-one.
35. 1-(4-Chloro-2-fluoro-5-ethoxyphenyl)-4,5-dicyano-3-methyl-1,3-dihydro-2H-imidazol-2-one.
36. 1-(4-Chloro-2-fluoro-5-allyloxyphenyl)-4,5-dicyano-3-methyl-1,3-dihydro-2H-imidazol-2-one.
37. 1-(4-Bromo-2-fluoro-5-(1-methylethoxy)phenyl)-4,5-dicyano-3-methyl-1,3-dihydro-2H-imidazol-2-one.
38. 1-(4-Chloro-2-fluoro-5-(1-methylethoxy)phenyl)-4,5-dicyano-3-methyl-1,3-dihydro-2H-imidazol-2-one.
39. 1-(4-Bromo-2-fluoro-5-propargyloxyphenyl)-4,5-dicyano-3-ethyl-1,3-dihydro-2H-imidazol-2-one.
40. 1-(4-Chloro-2-fluoro-5-methoxymethoxyphenyl)-4,5-dicyano-3-methyl-1,3-dihydro-2H-imidazol-2-one.
41. 1-(4-Chloro-2-fluoro-5-(1-methyl-2-propynyloxy)phenyl)-4,5-dicyano-3-methyl-1,3-dihydro-2H-imidazol-2-one.
42. 1-(4-Chloro-2-fluoro-5-difluoromethoxyphenyl)-4,5-dicyano-3-methyl-1,3-dihydro-2H-imidazol-2-one.
43. 1-(4-Chloro-2-fluoro-5-[(2-methoxyethoxy)methoxy]-phenyl)-4,5-dicyano-3-methyl-1,3-dihydro-2H-imidazol-2-one.
44. 1-(4-Chloro-2-fluoro-5-acetoxyphenyl)-4,5-dicyano-3-methyl-1,3-dihydro-2H-imidazol-2-one.
45. 1-(4-Chloro-2-fluoro-5-methylthiomethoxyphenyl)-4,5-dicyano-3-methyl-1,3-dihydro-2H-imidazol-2-one.
46. 1-(4-Chlorophenyl)-4,5-dicyano-3-benzyl-1,3-dihydro-2H-imidazol-2-one.
47. 1-(4-Chlorophenyl)-4,5-dicyano-1,3-dihydro-2H-imidazol-2-one.
48. 1-(4-Chlorophenyl)-4,5-dicyano-3-(prop-2-yn-1-yl)-1,3-dihydro-2H-imidazol-2-one.
49. 1-(4-Chlorophenyl)-4,5-dicyano-3-cyanomethyl-1,3-dihydro-2H-imidazol-2-one.
50. 1-(4-Chloro-2-fluoro-5-(1-methyl-2-propynyloxy)phenyl)-4-cyano-5-chloro-3-ethyl-1,3-dihydro-2H-imidazol-2-one.
51. 1-(4-Chlorophenyl)-4,5-dicyano-3-difluoromethyl-1,3-dihydro-2H-imidazol-2-one.
52. 1-(4-Chlorophenyl)-4-cyano-5-bromo-3-methyl-1,3-dihydro-2H-imidazol-2-one.
53. 1-(4-Chlorophenyl)-4-cyano-5-fluoro-3-methyl-1,3-dihydro-2H-imidazol-2-one.
54. 1-(4-Chlorophenyl)-3,4-dimethyl-5-cyano-1,3-dihydro-2H-imidazol-2-one.
55. 1-(2,4-Dichlorophenyl)-3,4-dimethyl-5-cyano-1,3-dihydro-2H-imidazol-2-one.
56. 1-(4-Chlorophenyl)-3-methyl-5-cyano-1,3-dihydro-2H-imidazol-2-one.
57. 1-(4-Bromo-2-fluoro-5-methoxyphenyl)-3-difluoromethyl-4,5-dicyano-1,3-dihydro-2H-imidazole-2-one.
58. 1-(4-Chloro-2-fluoro-5-methoxyphenyl)-4,5-dicyano-4-hydroxy-3-methyl-tetrahydro-2H-imidazol-2-one.
59. 1-(4-Chloro-2-fluoro-5-methoxyphenyl)-4,5-dicyano-3-difluoromethyl-dihydro-2H-imidazol-2-one.
60. 1-(4-Chloro-2-fluorophenyl)-3-benzyl-4,5-dicyano-1,3-dihydro-2H-imidazol-2-one.
61. 1-(4-Chloro-2-fluorophenyl)-4,5-dicyano-1,3-dihydro-2H-imidazol-2-one.
62. 1-(4-Chloro-2-fluorophenyl)-4,5-dicyano-3-difluoromethyl-1,3-dihydro-2H-imidazol-2-one.
63. 1-(4-Chloro-2-fluoro-5-nitrophenyl)-4,5-dicyano-3-difluoromethyl-1,3-dihydro-2H-imidazole-2-one.
64. 1-(5-Amino-4-chloro-2-fluorophenyl)-4,5-dicyano-3-difluoromethyl-1,3-dihydro-2H-imidazol-2-one.
65. 1-(4-Chloro-2-fluoro-5-bis(methanesulphonyl)amino-phenyl)-4,5-dicyano-3-difluoromethyl-1,3-dihydro-2H-imidazol-2-one.
66. 1-(4-Chloro-2-fluoro-5-methanesulphonylaminophenyl)-4,5-dicyano-3-difluoromethyl-1,3-dihydro-2H-imidazol-2-one.
67. 1(5-Acetamido-4-chloro-2-fluorophenyl)-4,5-dicyano-3-difluoromethyl-1,3-dihydro-2H-imidazol-2-one.
68. 1-(4-Chlorophenyl)-5,6-dicyano-3-methyl-2,4(1H,3H)-pyrimidinedione.
69. 2-(4-Chlorophenyl)-2,3,5,6,7,8-hexahydro-3-oxoimidazo-[1,5-a]pyridine-1-carbonitrile.
70. 2-(4-Chlorophenyl)-2,3,6,7-tetrahydro-3-oxo-5H-pyrrolo-[1,2-c]imidazole-1-carbonitrile.
71. 2-(4-Chloro-2-fluoro-5-hydroxyphenyl)-2,3,5,6,7,8-hexahydro-3-oxoimidazo-[1,5a]pyridine-1-carbonitrile.
72. 2-(4-Chloro-2-fluoro-5-methoxyphenyl)-2,3,6,7,8,9-hexahydro-3-oxo-5H-imidazo-[1,5a]azepine-1-carbonitrile.
73. 2-(4-Chloro-2-fluoro-5-methoxyphenyl)-2,3,5,6,7,8-hexahydro-3-oxoimidazo-[1,5a]pyridine-1-carbonitrile.
74. 2-(4-Chloro-2-fluoro-5-propargyloxyphenyl)-2,3,5,6,7,8-hexahydro-3-oxoimidazo-[1,5a]pyridine-1-carbonitrile.
75. 2-(4-Chlorophenyl)-2,3,6,7,8,9-hexahydro-3-oxo-5H-imidazo-[1,5-a]azepine-1-carbonitrile.
76. 2-(4-Chloro-2-fluorophenyl)-2,3,5,6,7,8-hexahydro-3-oxoimidazo-[1,5-a]pyridine-1-carbonitrile.
77. 2-(2,4-Dichlorophenyl)-2,3,5,6,7,8-hexahydro-3-oxoimidazo-[1,5-a]pyridine-1-carbonitrile.
78. 2-(4-Chloro-2-fluoro-5-propargyloxyphenyl)-2,3,6,7,8,9-hexahydro-3-oxo-5H-imidazo-[1,5-a]azepine-1-carbonitrile.
79. 2-(4-Chloro-2-fluoro-5-cyanomethoxyphenyl)-2,3,5,6,7,8-hexahydro-3-oxoimidazo-[1,5-a]pyridine-1-carbonitrile.
80. 2-(4-Chloro-2-fluoro-5-(1-ethoxycarbonylethoxy)phenyl)-2,3,5,6,7,8-hexahydro-3-oxoimidazo-[1,5-a]pyridine-1-carbonitrile.

81. 2-(4-Chloro-2-fluoro-5-(ethoxycarbonylmethoxy)-phenyl)-2,3,5,6,7,8-hexahydro-3-oxoimidazo-[1,5-a]pyridine-1-carbonitrile.
82. 2-(4-Chloro-2-fluorophenyl)-octahydro-8a-hydroxy-3-oxoimidazo[1,5-a]pyridine-1-carbonitrile.
83. 2-(4-Chloro-5-ethoxycarbonyl-2-fluorophenyl)-2,3,5,6,7,8-hexahydro-3-oxoimidazo[1,5-a]pyridine-1-carbonitrile.
84. 6-Fluoro-5-(1-cyano-2,3,5,6,7,8-hexahydro-3-oxoimidazo[1,5-a]pyridin-2-yl)-3-propargyl-2-benzothiazolinone.

| CMPD NO | X | Y | Z | W | R | R¹ | A | U,V |
|---|---|---|---|---|---|---|---|---|
| 1 | H | Cl | H | Cl | C₃H₇ | CN | bond | bond |
| 2 | H | Cl | H | CN | C₃H₇ | CN | bond | bond |
| 3 | H | H | H | CN | CH₃ | CN | bond | bond |
| 4 | F | Cl | OCH₂C≡CH | Cl | CH₃ | CN | bond | bond |
| 5 | H | Cl | Cl | CN | CH₃ | CN | bond | bond |
| 6 | H | CH₃ | H | CN | CH₃ | CN | bond | bond |
| 7 | H | Cl | H | CN | C₂H₅ | CN | bond | bond |
| 8 | H | F | H | Cl | CH₃ | CN | bond | bond |
| 9 | H | CF₃ | H | Cl | CH₃ | CN | bond | bond |
| 10 | H | CN | H | CN | CH₃ | CN | bond | bond |
| 11 | H | OCF₃ | H | Cl | CH₃ | CN | bond | bond |
| 12 | H | Cl | H | Cl | C₆H₅ | CN | bond | bond |
| 13 | H | Cl | H | Cl | CH₃ | CN | bond | bond |
| 14 | Cl | H | H | Cl | CH₃ | CN | bond | bond |
| 15 | H | Cl | Cl | Cl | CH₃ | CN | bond | bond |
| 16 | H | CH₃ | H | Cl | CH₃ | CN | bond | bond |
| 17 | H | Cl | H | CN | CH₃ | CN | bond | bond |
| 18 | Cl | Cl | OCH(CH₃)₂ | Cl | CH₃ | CN | bond | bond |
| 19 | H | H | H | Cl | CH₃ | CN | bond | bond |
| 20 | F | Cl | OCH₂C≡CH | CN | CH₃ | CN | bond | bond |
| 21 | H | Cl | H | CN | C₆H₅ | CN | bond | bond |
| 22 | H | Cl | H | Cl | C₂H₅ | CN | bond | bond |
| 23 | F | Br | OCH₂C≡CH | Cl | CH₃ | CN | bond | bond |
| 24 | F | Cl | OCH₂C≡CH | Cl | C₂H₅ | CN | bond | bond |
| 25 | F | Cl | OCH(CH₃)CO₂C₂H₅ | CN | CH₃CN | bond | bond | |
| 26 | H | Br | H | CN | C₂H₅ | CN | | bond |
| 27 | Cl | Cl | H | CN | CH₃ | CN | bond | bond |
| 28 | H | Br | H | Cl | C₂H₅ | CN | bond | bond |
| 29 | F | Br | OCH₃ | CN | CH₃ | CN | bond | bond |
| 30 | F | Cl | OCH₂C≡CH | Cl | C₃H₇ | CN | bond | bond |
| 31 | F | Cl | OCH₂C≡CH | CN | C₃H₇ | CN | bond | bond |
| 32 | F | Cl | OCH(CH₃)CO₂C₂H₅ | CN | C₂H₇ | CN | bond | bond |
| 33 | F | Cl | OCH₃ | CN | CH₃ | CN | bond | bond |
| 34 | F | Cl | OH | CN | CH₃ | CN | bond | bond |
| 35 | F | Cl | OCH₂CH₃ | CN | CH₃ | CN | bond | bond |
| 36 | F | Cl | OCH₂CH=CH₂ | CN | CH₃ | CN | bond | bond |
| 37 | F | Br | OCH(CH₃)₂ | CN | CH₃ | CN | bond | bond |
| 38 | F | Cl | OCH(CH₃)₂ | CN | CH₃ | CN | bond | bond |
| 39 | F | Br | OCH₂C≡CH | CN | C₂H₅ | CN | bond | bond |
| 40 | F | Cl | OCH₂OCH₃ | CN | CH₃ | CN | bond | bond |
| 41 | F | Cl | OCH(CH₃)C≡CH | CN | CH₃ | CN | bond | bond |
| 42 | F | Cl | OCF₂H | CN | CH₃ | CN | bond | bond |
| 43 | F | Cl | OCH₂O(CH₂)₂OCH₃ | CN | CH₃ | CN | bond | bond |
| 44 | F | Cl | OCOCH₃ | CN | CH₃ | CN | bond | bond |
| 45 | F | Cl | OCH₂SCH₃ | CN | CH₃ | CN | bond | bond |
| 46 | H | Cl | H | CN | CH₂Ph | CN | bond | bond |
| 47 | H | Cl | H | CN | H | CN | bond | bond |
| 48 | H | Cl | H | CN | CH₂C≡CH | CN | bond | bond |
| 49 | H | Cl | H | CN | CH₂CN | CN | bond | bond |
| 50 | F | Cl | OCH(CH₃)C≡CH | Cl | CH₂CH₃ | CN | bond | bond |
| 51 | H | Cl | H | CN | CF₂H | CN | bond | bond |
| 52 | H | Cl | H | Br | CH₃ | CN | bond | bond |
| 53 | H | Cl | H | F | CH₃ | CN | bond | bond |
| 54 | H | Cl | H | CN | CH₃ | CH₃ | bond | bond |
| 55 | Cl | Cl | H | CN | CH₃ | CH₃ | bond | bond |
| 56 | H | Cl | H | CN | CH₃ | H | bond | bond |
| 57 | F | Br | OCH₃ | CN | CF₂H | CN | bond | bond |
| 58 | F | Cl | OCH₃ | CN | CH₃ | CH₃ | bond | H,OH |
| 59 | F | Cl | OCH₃ | CN | CF₂H | CN | bond | bond |
| 60 | F | Cl | H | CN | CH₂Ph | CN | bond | bond |
| 61 | F | Cl | H | CN | H | CN | bond | bond |
| 62 | F | Cl | H | CN | CF₂H | CN | bond | bond |
| 63 | F | Cl | NO₂ | CN | CF₂H | CN | bond | bond |
| 64 | F | Cl | NH₂ | CN | CF₂H | CN | bond | bond |
| 65 | F | Cl | N(SO₂CH₃)₂ | CN | CF₂H | CN | bond | bond |
| 66 | F | Cl | NHSO₂CH₃ | CN | CF₂H | CN | bond | bond |
| 67 | F | Cl | NHCOCH₃ | CN | CF₂H | CN | bond | bond |
| 68 | H | Cl | H | CN | CH₃ | CN | C=O | bond |

| CMPD NO | X | Y | Z | W | —R—R¹— | n | A | U,V |
|---|---|---|---|---|---|---|---|---|
| 69 | H | Cl | H | CN | —(CH₂)ₙ— | 4 | bond | bond |
| 70 | H | Cl | H | CN | —(CH₂)ₙ— | 3 | bond | bond |
| 71 | F | Cl | OH | CN | —(CH₂)ₙ— | 4 | bond | bond |

| | | | -continued | | | | | |
|---|---|---|---|---|---|---|---|---|
| 72 | F | Cl | OCH₃ | CN | —(CH₂)ₙ— | 5 | bond | bond |
| 73 | F | Cl | OCH₃ | CN | —(CH₂)ₙ— | 4 | bond | bond |
| 74 | F | Cl | OCH₂C≡CH | CN | —(CH₂)ₙ— | 4 | bond | bond |
| 75 | H | Cl | H | CN | —(CH₂)ₙ— | 5 | bond | bond |
| 76 | F | Cl | H | CN | —(CH₂)ₙ— | 4 | bond | bond |
| 77 | Cl | Cl | H | CN | —(CH₂)ₙ— | 4 | bond | bond |
| 78 | F | Cl | OCH₂C≡CH | CN | —(CH₂)ₙ— | 5 | bond | bond |
| 79 | F | Cl | OCH₂CN | CN | —(CH₂)ₙ— | 4 | bond | bond |
| 80 | F | Cl | OCH(CH₃)CO₂C₂H₅ | CN | —(CH₂)ₙ— | 4 | bond | bond |
| 81 | F | Cl | OCH2CO2C₂H₅ | CN | —(CH₂)ₙ— | 4 | bond | bond |
| 82 | F | Cl | H | CN | —(CH₂)ₙ— | 4 | bond | H,OH |
| 83 | F | Cl | CO₂C₂H₅ | CN | —(CH₂)ₙ— | 4 | bond | bond |

| CMPD NO | X | —Y—Z— | W | —R—R¹— | n | A | U,V |
|---|---|---|---|---|---|---|---|
| 84 | F | —SCON(CH₂C≡CH)— | CN | —(CH₂)ₙ— | 4 | bond | bond |

The compounds of Formula A are useful as herbicides. As used herein, the term "herbicide" includes a compound which controls or adversely modifies the growth, or reduces the vigor of, unwanted vegetation.

Also provided by the present invention are agricultural compositions comprising one or more compounds of Formula A together with a suitable agricultural adjuvant or carrier. A further embodiment of the present invention is a method of controlling or adversely modifying the growth, or reducing the vigor of, undesired vegetation. Such methods comprise, for example, applying a herbicidally-effective amount of one or more compounds of Formula A preemergently and/or postemergently to the locus of the undesired vegetation. The term "herbicidally-effective" includes an amount of compound which causes an adversely modifying effect to, or reduces the vigor of, unwanted vegetation, and includes deviations from natural development, killing, regulation, dessication, retardation, and the like, such that the vegetation is incapable of recovering following application.

The novel phenylimidazolone compounds of Formula A may be prepared by various procedures. One such procedure may be illustrated by Scheme 1, as follows:

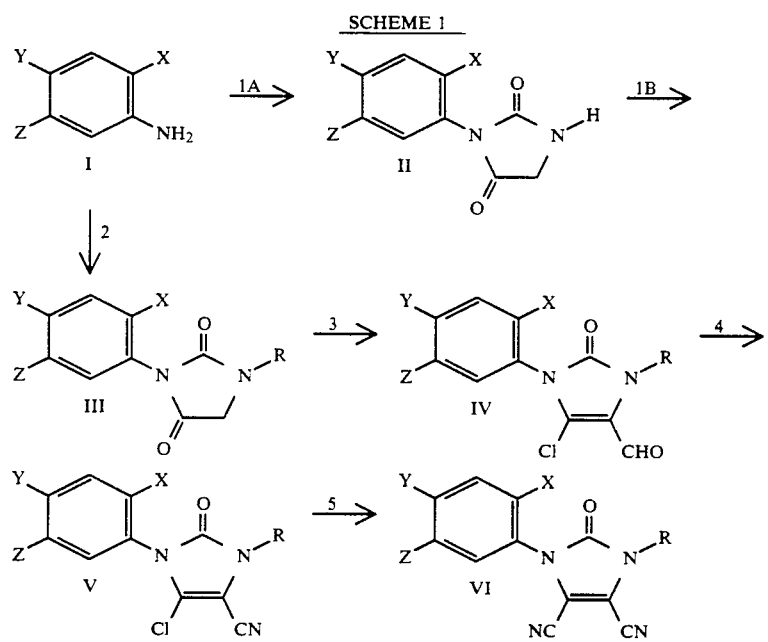

Scheme 1

The phenylimidazolones represented by structure V may be prepared from the corresponding chloroaldehyde IV, which in turn may be prepared from the corresponding hydantoins III. See U.S. Pat. No. 4,345,936 for the preparation of chloroaldehydes I→IV. See also, E. Ware, Chem. Rev., 46 (1950) 406 and Oragi et al, J. Chem. Soc., 1 (1974) 219 for additional preparations of hydantoins and N-3 alkylation of hydantoins. Conversion of the aldehyde IV to the nitrile V is accomplished by dehydration of the corresponding oxime, using standard conditions. See, Synthesis, 9 (1983) 748. The dinitriles represented by VI are prepared from V by chloride displacement with an alkali metal nitrile, such as, for example, NaCN, KCN or LiCN, in an organic solvent, such as, for example, tetrahydrofuran (THF) or dimethylformamide (DMF), at a temperature ranging from about 0° to 150° C., or more preferably at a temperature ranging from about 50° to 110° C.

When Z is a —O—Alk, as defined herein, the compounds may be further modified as illustrated by Scheme 1B, below:

SCHEME 1B

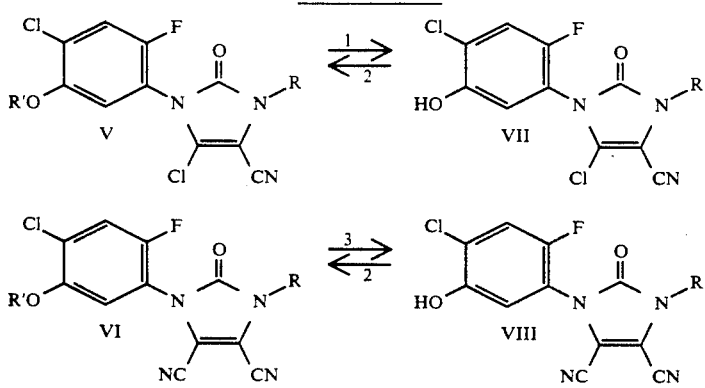

Scheme 1B

Further modification of the Z position of the chlorocyano compounds may be accomplished by cleavage of the ether group in V with boron tribromide to form the phenol VII. Subsequent realkylation with a variety of alkyl halides can then be accomplished, either through use of potassium carbonate in refluxing acetone or sodium hydride in DMF.

Likewise, the dinitriles VI may be modified to generate novel ethers and esters by dealkylation with aluminum chloride followed by realkylation under the conditions described above.

Other procedures utilized to prepare the novel phenylimidazolone compounds wherein W and $R^1$ are each —CN, may be illustrated by Scheme 2 and Scheme 3, below:

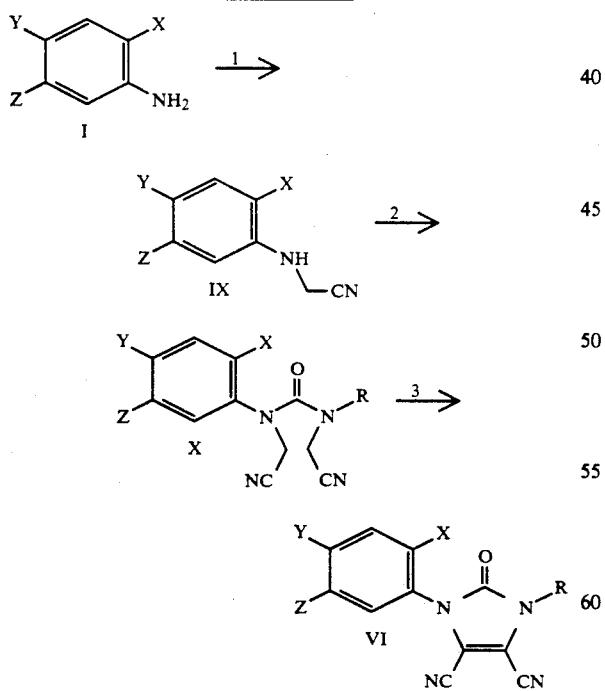

Scheme 2

The dinitriles VI may be prepared via an acyclic dinitrile X. First, an aniline I is treated with a formaldehyde equivalent, such as paraformaldehyde, and an alkali metal cyanide, such as, for example, potassium cyanide, in an organic acid, such as, for example, acetic acid, to form an arylaminoacetonitrile IX. See, Walker et al, *J. Org. Chem.*, 37 (1972) 3755. Next, the arylaminoacetonitrile IX is converted into a carbamoyl chloride by reaction with phosgene, or a phosgene equivalent, such as, for example, triphosgene, in an organic solvent, such as, for example, dioxane, at a temperature ranging from about 50° to 100° C. The carbamoyl chloride is then converted directly into the urea X by reaction with an alkylaminoacetonitrile, either in a basic organic solvent, such as, for example, pyridine, or in a neutral solvent with an organic base, such as, for example, triethylamine (TEA).

The acyclic urea X can then be converted into the dinitrile VI by first generating a dihalide, using two equivalents of a halogenating agent, such as, for example, $SO_2Cl_2$, N-bromosuccinimide (NBS) or bromine, in an organic solvent at a temperature ranging from 0° to 100° C., or more preferably, at a temperature ranging from about 40° to 80° C. Direct treatment of the dihalo urea with a tertiary amine, such as, for example, triethylamine or 1,8-diazabicyclo(5,4,0)undec-7-ene (DBU), in an organic solvent generates the dinitrile VI.

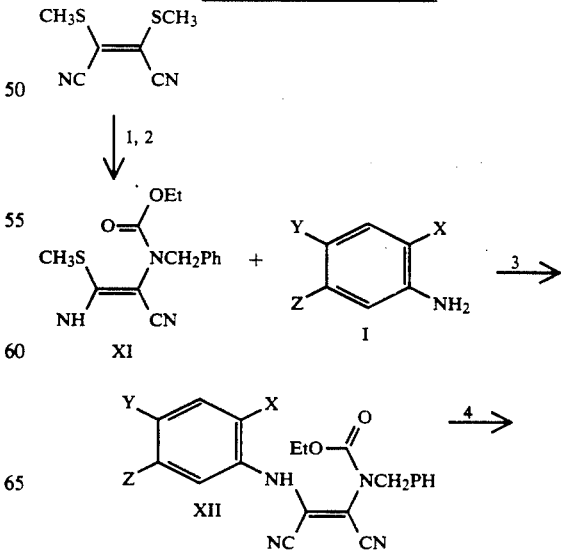

-continued
SCHEME 3 (Z ≠ OR')

XIII

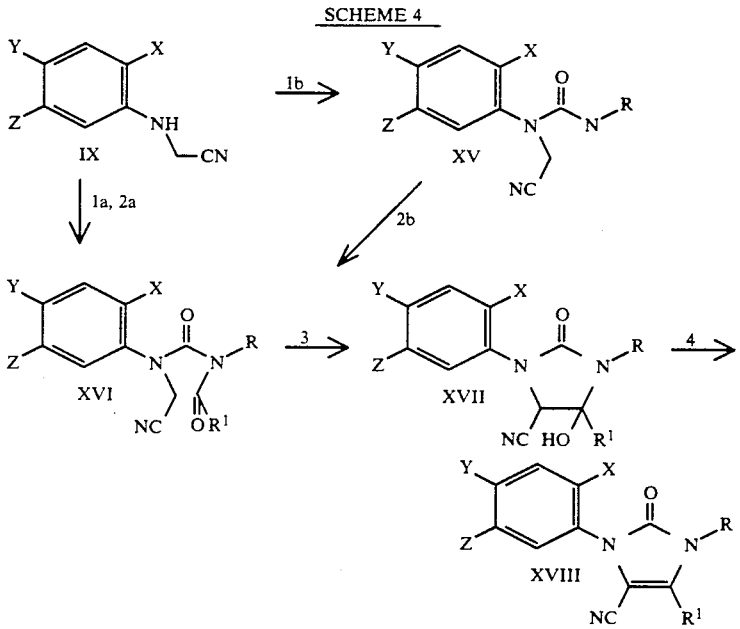

SCHEME 4

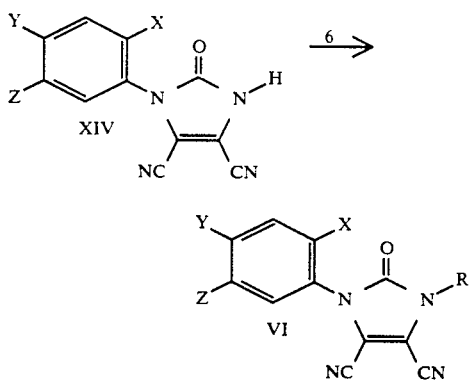

XIV

VI

Scheme 3

The dinitriles VI may also be prepared according to the following general procedure:

The maleonitrile XI is prepared from the known bis(methylthio)maleonitrile (see, *Chem. Ber.*, 88 [1955] 1771 and *Chem. Ber.*, 90 [1957]438) in two stages. The first involves benzylamine displacement from the bis(-methylthio)-maleonitrile (neat). The resulting enamine is then deprotonated with sodium hydride and acylated with ethyl chloroformate. Addition of the lithium salt of a suitable aniline I to 2-((N-ethoxycarbonyl) benzylamino)-3-methylthiomaleonitrile XI in an organic solvent yields the acyclic carbamate XII. Thermal ring closure in hot DMF or N-methylpyrrolidinone (NMP) generates the benzylated imidazolinone XIII. The N-benzyl imidazolinone XIII is debenzylated by the action of aluminum chloride in benzene to form XIV. Realkylation is then accomplished on nitrogen by using the appropriate alkylating agent and a base, such as, for example, sodium hydride, to deliver VI.

Preparation of the ring fused analogs of Formula A, wherein A is a bond and R—R¹ represents a ring, or other analogs of Formula A, wherein R and R1 independently represent alkyl groups, may be illustrated by Scheme 4, below:

Scheme 4

Compounds XVIII wherein R—R1 represent a ring can be prepared from an arylaminoacetonitrile XI. The acylated urea XVI (steps 1a, 2a) is generated by formation of the carbamoyl chloride, as described in Scheme 2, followed by condensation with an amide, such as, for example, γ-valerolactam, in the presence of an organic base, such as TEA. The urea is then cyclized (step 3) by treatment with an organic or inorganic base, such as, for example, lithium diisopropylamide in THF, sodium hydride in DMF, or DBU in hot THF, to form the corresponding cyclized compound XVII. These intermediates are sometimes isolated, however, more often, they spontaneously dehydrate to form XVIII. In the former case, dehydration can be effected either by using an acidic workup, such as 1N hydrochloric acid, following the ring closure step, or by heating the intermediate hydroxy compound XVII in toluene containing a catalytic amount of p-toluenesulphonic acid. Compounds such as XVIII, wherein Z is —O—Alk, as defined herein, can be further modified by the procedures described herein in Scheme 1B.

Acyclic N-acylureas XVI, wherein R and R1 independently represent Alk, as defined herein, can be prepared from the corresponding ureas XV by N-acylation with a alkanoic acid anhydride under standard conditions (see, for example, Barnes et al, *Pest Sci.* 23 [1988] 65). Ring closure and dehydration are effected under the same conditions as the cyclic examples described above. The ureas XV may be prepared from IX by reaction with an alkyl isocyanate in an organic solvent such as toluene, at a temperature ranging from about 50° C. to 110° C.

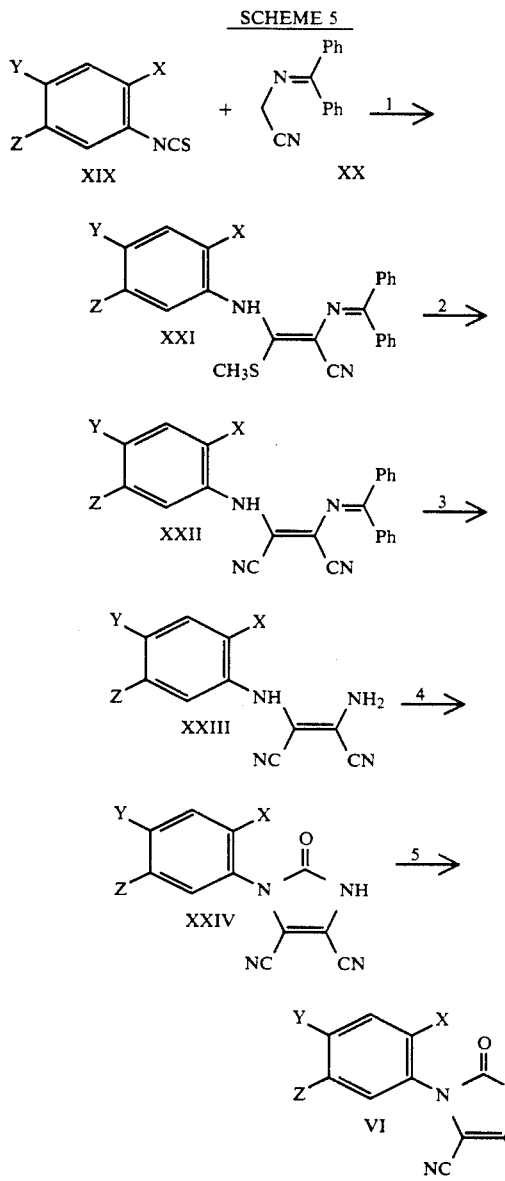

Scheme 5

The dicyanoimidazolinones XXIV can also be prepared from the known benzophenone imine of aminoacetonitrile XX (see, M. J. O'Donnell and R. L. Polt, *J. Org. Chem.* 47 [1982] 2663). Reaction with an aryl isothiocyanate and methyl iodide under basic conditions generates a ketene aminothioacetal XXI. The methylthio group can then be displaced by cyanide with an alkali metal cyanide in hot DMF to form XXII. The diaminomaleonitrile XXIII can be formed by acidic hydrolysis of XXII. Finally, XXIII can be converted into bis-cyanoimidazolinones VI by first forming the imidazolidinone XXIV with phosgene or a phosgene equivalent such as triphosgene in an organic solvent such as dioxane. The N-unsubstituted imidazolidinone can then be alkylated using conditions described in Scheme 3.

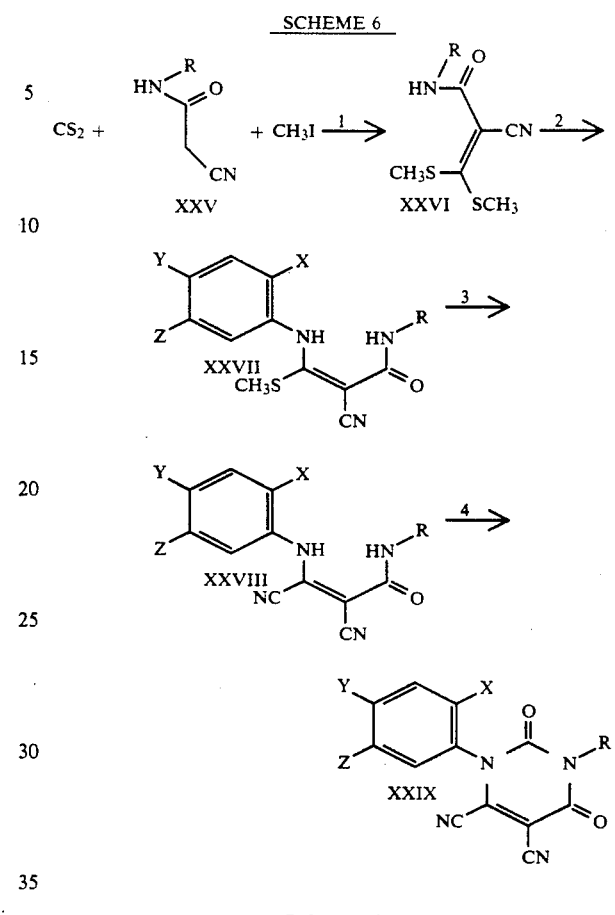

Scheme 6

Compounds of Formula A wherein substituent A is a carbonyl group, C=O, may be prepared according to Scheme 6, above. Carbon disulphide can be reacted with a cyanocyanoacetamide XXV under basic conditions, followed by alkylation as described in Scheme 5 to form the ketene dithioacetal XXVI. Reaction of the dithioacetal with the lithium salt of an aniline in ether generates the arylaminoacrylamide XXVII. Cyanide displacement, using an alkali metal cyanide in an organic solvent, such as DMF, results in the formation of XXVIII. Subsequent reaction with ethyl chloroformate, in the presence of an organic base, such as TEA or pyridine, generates XXIX.

The following non-limiting examples further illustrate the present invention:

EXAMPLE 1

Preparation of 1-(4-chlorophenyl)-5-chloro-4-cyano-3-propyl-1,3-dihydro-2H-imidazol-2-one The compound 1-(4-chlorophenyl)-4-formyl-5-chloro-3-propyl-1,3-dihydro-2H-imidazol-2-one (IV) was prepared according to the procedure disclosed in U.S. Pat. No. 4,345,936. This product (1.1 g, 3.2 mmol) was then stirred in a mixture of approximately 5:1 ethanol:water, to which approximately 3 equivalents of hydroxylamine hydrochloride was added. The mixture was heated briefly on a steam bath to effect total solution, then stirred overnight. The solution was poured over water, extracted three times with ethyl acetate, then the organic layer was washed with water. The solution was then dried, filtered, and evaporated via standard techniques to give 800 mg of material. This material (0.8 g, 2.2 mmol) was dissolved in dichloromethane to which was added triethylamine (1.1 g, 11 mmol). To the resulting solution was added Cl$_3$CCOCl (1.2 g, 6.6 mmol) dropwise in 10 mL dichloromethane, and the solution was stirred at room temperature. After approximately ten minutes, the solution was poured onto water, separated, washed with dilute HCl, then dried, filtered, and evaporated via standard techniques. Recrystallization was initiated from diethyl ether/hexane at −78° C., and the mixture was then filtered to give 220 mg of 1-(4- chlorophenyl)-5-chloro-4-cyano-3-propyl-1,3-dihydro-2H-imidazole-2-one (V) as a white solid (m.p. 102°–3° C.).

EXAMPLE 2

Preparation of 1-(4-chloro-2-fluoro-5-propargyloxyphenyl)-5-chloro-4-cyano-3-propyl-1,3-dihydro-2H-imidazol-2-one The compound 1-(4-chloro-2-fluoro-5-propargyloxyphenyl)-4-formyl-5-chloro-3-propyl-1,3-dihydro-2H-imidazol-2-one (IV) was prepared according to the procedure disclosed in U.S. Pat. No. 4,345,936. This product (2.8 g, 7.5 mmol) was placed in 50 mL of ethanol and 10 mL of H$_2$O and was treated with stirring with 2 equivalents of NH$_2$OH.HCl. This mixture was heated briefly on a steam bath then cooled and stirred for one hour. The mixture was diluted with H$_2$O, extracted with dichloromethane, washed with brine, and dried and concentrated via standard techniques. The residue (2.8 g) was taken up in 30 mL of dichloromethane and treated with 2 mL of triethylamine and 1 mL of Cl$_3$CCOCl (dropwise). The solution was washed with water and brine, then dried and concentrated via standard techniques. Recrystallization of the solid residue from chloroform-petroleum ether gave 1.4 g of 1-(4-chloro-2-fluoro-5-propargyloxyphenyl)-5-chloro-4-cyano-3-propyl-1,3-dihydro-2H-imidazol-2-one (V) (m.p. 122° C.).

EXAMPLE 3

Preparation of 1-(4-chloro-2-fluoro-5-propargyloxyphenyl)-5-chloro-4-cyano-3-methyl-1,3-dihydro-2H-imidazol-2-one 2-Fluoro-4-chloro-5-propargyloxyaniline (see, European Patent Application 0061741) (I) (5.1 g, 25.6 mmol) was dissolved in 100 mL of p-dioxane. Triphosgene (2.5 g, 8.5 mmol) was added and the solution was heated to approximately 70° C. for four hours, then cooled and evaporated to give a dark oil. This material was taken up in 50 mL of dioxane and added to an aqueous solution of sarcosine (3.4 g, 38.4 mmol) and sodium hydroxide (2 g, 50 mmol). This solution was heated to reflux for one-half hour, then cooled and poured onto water. The solution was washed twice with ethyl ether, acidified with concentrated HCl, and extracted with ethyl acetate, then dried, filtered, and evaporated via standard techniques. The mixture was recrystallized with ethyl acetate/heptane, then washed with hexane to yield 3.4 g of a tan colored solid (m.p. 132°–3° C.). This material was heated to reflux with stirring in 1:1 HCl:H$_2$O for two hours, then cooled, diluted with water, and filtered to give 2.7 g of the corresponding methyl-hydantoin (III) (m.p. 189°–91° C.).

The above product (III) (6.4 g) was heated to reflux for four hours in a mixture of approximately 75 mL of POCl$_3$ and 5 mL of DMF. The mixture was cooled, evaporated, poured onto ice, and extracted with 100 mL of CHCl$_3$ (4 times). The mixture was washed twice with water, then dried, filtered and evaporated to give 1.9 g of the corresponding aldehyde (IV) as a dark oil.

The above product (IV) was stirred in approximately 100 mL of 5:1 ethanol:water. To this mixture was added NH$_2$OH.HCl (1.1 g, 16.7 mmol) and the mixture was stirred overnight at room temperature. The mixture was then poured onto water, extracted with ethyl acetate, washed with water, dried, filtered, and evaporated via standard techniques to yield 1.2 g of a yellow foam. This material was stirred in 50 mL of dichloromethane with triethylamine (0.7 g, 6.7 mmol). To this mixture was added trichloroacetylchloride (0.9 g, 5 mmol). After stirring overnight at room temperature, the mixture was poured onto water, shaken, and separated. The organic layer was then washed with dilute HCl, dried, filtered, and evaporated via standard techniques. Recrystallization from ethyl ether/hexane gave 0.5 g of 1-(4-chloro-2-fluoro-5-propargyloxyphenyl)-5-chloro-4-cyano-3-methyl-1,3-dihydro-2H-imidazol-2-one (V) (m.p. 127°–9° C.).

EXAMPLE 4

Preparation of 1-(4-chlorophenyl)-5-chloro-4-cyano-3-phenyl-1,3-dihydro-2H-imidazol-2-one 4-Chlorophenylisocyanate (I) (8.6 g, 56 mmol) was added to a stirred solution of phenylglycine ethyl ester (10 g, 56 mmol) and triethylamine (TEA) (5.6 g, 56 mmol) in tetrahydrofuran and heated to reflux for 3 hours. The mixture was cooled, poured onto water, extracted with ethyl acetate, and washed with dilute HCl. The mixture was then hydrolyzed with sodium hydroxide in ethanol/H$_2$O at room temperature overnight to give 8.1 g of acid (m.p. 123°–4° C.), which was recrystallized from CHCl$_3$/hexane. The acid (approximately 7.9 g) was heated to reflux and stirred for 3 hours in 1:1 HCl:H$_2$O. The mixture was allowed to cool, then diluted with water and filtered to give 5.8 g of (III) (m.p. 137°–8° C.). This material was converted to the chloro-aldehyde (IV) using conditions described previously in Example 3 to give 2.0 g of (IV) recrystallized from ethyl acetate/heptane (m.p. 160°–2° C.).

To the above product (IV) (approximately 1.8 g, 5.4 mmol) stirred in ethanol/H$_2$O was added hydroxylamine.HCl (1 g, 15 mmol). The mixture was heated on a steam bath until the ingredients dissolved, and was stirred at room temperature overnight. The mixture was diluted with water and filtered to give 2.0 g of a solid, which was stirred in approximately 75 mL CH$_2$Cl$_2$ at room temperature. TEA (1.2 g, 11.5 mmol) was added and the solid went into solution. To this solution was then added trichloroacetyl chloride (1.6 g, 8.6 mmol) in approximately 10 mL of CH$_2$Cl$_2$ dropwise and the resulting mixture was stirred overnight. The mixture was washed with water, then dilute HCl, and dried, filtered, and evaporated via standard techniques to give 1.15 g of 1-(4-chlorophenyl)-5-chloro-4-cyano-3-phenyl-1,3-dihydro-2H-imidazol-2-one (V) recrystallized from ethyl acetate/heptane (m.p. 146°–7° C.).

EXAMPLE 5

Preparation of
1-(4-chlorophenyl)-4,5-dicyano-3-propyl-1,3-dihydro-2H-imidazol-2-one The product of Example 1, 1-(4-chlorophenyl)-5-chloro-4-cyano-3-propyl-1,3-dihydro-2H-imidazol-2-one (V) (0.75 g, 2.5 mmol), was stirred in 25 mL of dimethylformamide. To this mixture was added KCN (0.5 g, 7.5 mmol) and the resulting mixture was heated to reflux for ten minutes, cooled, poured onto water, and extracted three times with 50 mL ethyl acetate. This material was then dried, filtered, and evaporated via standard techniques to give 0.38 g of 1-(4-chlorophenyl)-4,5-dicyano-3-propyl-1,3-dihydro-2H-imidazol-2-one (VI) recrystallized from ethyl acetate/hexane (m.p. 163°-5° C.).

EXAMPLE 6

Preparation of
1-(4-chloro-2-fluoro-5-propargyloxyphenyl)-4,5-dicyano-3-propyl-1,3-dihydro-2H-imidazol-2-one The product of Example 2, 1-(4-chloro-2-fluoro5-propargyloxyphenyl)-5-chloro-4-cyano-3-propyl-1,3-dihydro-2H-imidazol-2-one (V) (0.25 g, 0.68 mmol), was stirred in 10 mL dimethylformamide (DMF). To this mixture was added LiCN (2 mL of 0.5M in DMF, 1 mmol) and the resulting mixture was heated to 120° C. for 15 minutes. The mixture was cooled poured onto water, extracted with ethyl acetate, dried, concentrated and eluted through silica gel (50:50 ethyl acetate:hexane) to give 0.11 g of 1-(4-chloro-2-fluoro-5-propargyloxyphenyl)-4,5-dicyano-3-propyl-1,3-dihydro-2H-imidazol-2-one (VI) (m.p. 76° C.).

EXAMPLE 7

Preparation of
1-(4-chloro-2-fluoro-5-propargyloxyphenyl)-4,5-dicyano-3-methyl-1,3-dihydro-2H-imidazol-2-one The product of Example 3, 1-(4-chloro-2-fluoro-5-propargyloxyphenyl)-5-chloro-4-cyano-3-methyl-1,3-dihydro-2H-imidazol-2-one (V) (0.14 9, 0.4 mmol) was stirred in 20 mL dimethylformamide. To this mixture was added KCN (0.13 g, 2.0 mmol) and the resulting mixture was heated to reflux for ten minutes, however some starting material remained. The mixture was again heated to reflux one hour with the addition of CuCN (0.18 g, 2.0 mmol). The mixture was cooled, poured onto water, and extracted three times with 50 mL ethyl acetate. The organic solution was dried over MgSO4, filtered, and evaporated, then chromatographed to give approximately 30 mg of a glassy oil. Recrystallization with ethyl ether/hexane gave 22 mg of 1-(4-chloro-2-fluoro-5-propargyloxyphenyl)-4,5-dicyano-3-methyl-1,3-dihydro-2H-imidazol-2-one (VI) (m.p. 124°-6° C.).

EXAMPLE 8

Preparation of
1-(4-chlorophenyl)-4,5-dicyano-3-phenyl-1,3-dihydro-2H-imidazol-2-one The product of Example 4, 1-(4-chlorophenyl)-5-chloro-4-cyano-3-phenyl-1,3-dihydro-2H-imidazol-2-one (V) (0.94 g, 2.8 mmol) was stirred in 25 mL dimethylformamide. To this mixture was added KCN (0.6 g, 8.5 mmol) and the resulting mixture was heated to reflux for ten minutes. The mixture was then allowed to cool, poured onto water, extracted with ethyl acetate, dried, filtered, and evaporated via standard techniques. Recrystallization with ethyl acetate/heptane gave 0.5 g of 1-(4-chlorophenyl)-4,5-dicyano-3-phenyl-1,3-dihydro-2H-imidazol-2-one (VI) as an orange solid (m.p. 182°-4° C.).

The following examples were prepared according to the general procedure of Scheme 1, above.

EXAMPLE 9

1-(4-Chloro-2-fluoro-5-propargyloxyphenyl)-5-chloro-4-cyano-3-ethyl-1,3-dihydro-2H-imidazol-2-one (V) (m.p. 118° C.).

EXAMPLE 10

1-(4-Chlorophenyl)-4,5-dicyano-3-methyl-1,3-dihydro-2H-imidazol-2-one (VI) (m.p. 171° C.).

EXAMPLE 11

1-(4-Bromophenyl)-5-chloro-4-cyano-3-ethyl-1,3-dihydro-2H-imidazol-2-one (V) (m.p. 137°-8° C.).

EXAMPLE 12

1-(4-Chlorophenyl)-5-chloro-4-cyano-3-ethyl-1,3-dihydro-2H-imidazol-2-one (V) (m.p. 139°-40° C.).

EXAMPLE 13

1-(2,4-Dichlorophenyl)-4,5-dicyano-3-methyl-1,3-dihydro-2H-imidazol-2-one (VI) (m.p. 162°-5° C.).

EXAMPLE 14

1-(4-Fluorophenyl)-5-chloro-4-cyano-3-methyl-1,3-dihydro-2H-imidazol-2-one (V) (m.p. 144°-5° C.).

EXAMPLE 15

1-(4-Trifluoromethylphenyl)-5-chloro-4-cyano-3-methyl-1,3-dihydro-2H-imidazol-2-one (V) (m.p. 153°-4° C.).

EXAMPLE 16

1-(4-Trifluoromethoxyphenyl)-5-chloro-4-cyano-3-methyl-1,3-dihydro-2H-imidazol-2-one (V) (m.p. 112°-4° C.).

EXAMPLE 17

1-(4-Bromo-2-fluoro-5-propargyloxyphenyl)-5-chloro-4-cyano-3-methyl-1,3-dihydro-2H-imidazol-2-one (V) (m.p. 140° C.).

EXAMPLE 18

1-(4-Chlorophenyl)-5-chloro-4-cyano-3-methyl-1,3-dihydro-2H-imidazol-2-one (V) (m.p. 143° C.).

EXAMPLE 19

1-(2-Chlorophenyl)-5-chloro-4-cyano-3-methyl-1,3-dihydro-2H-imidazol-2-one (V) (m.p. 114° C.).

EXAMPLE 20

1-(3,4-Dichlorophenyl)-5-chloro-4-cyano-3-methyl-1,3-dihydro-2H-imidazol-2-one (V) (m.p. 161°-3° C.).

EXAMPLE 21

1-(4-Methylphenyl)-5-chloro-4-cyano-3-methyl-1,3-dihydro-2H-imidazol-2-one (V) (m.p. 166°-70° C.).

EXAMPLE 22

1-(2,4-Dichloro-5-(1-methylethoxy)phenyl)-5-chloro-4-cyano-3-methyl-1,3-dihydro-2H-imidazol-2-one (V) (m.p. 140°-2° C.).

EXAMPLE 23

1-Phenyl-5-chloro-4-cyano-3-methyl-1,3-dihydro-2H-imidazol-2-one (V) (m.p. 138°-40° C.).

EXAMPLE 24

1-(4-Chlorophenyl)-4,5-dicyano-3-ethyl-1,3-dihydro-2H-imidazol-2-one (VI) (m.p. 149°-50° C.).

EXAMPLE 25

1-Phenyl-4,5-dicyano-3-methyl-1,3-dihydro-2H-imidazol-2-one (VI) (m.p. 197°-8° C.).

EXAMPLE 26

1-(3,4-Dichlorophenyl)-4,5-dicyano-3-methyl-1,3-dihydro-2H-imidazol-2-one (VI) (m.p. 150°-2° C.).

EXAMPLE 27

1-(4-Methylphenyl)-4,5-dicyano-3-methyl-1,3-dihydro-2H-imidazol-2-one (VI) (m.p. 142°-3° C.).

EXAMPLE 28

1-(4-Cyanophenyl)-4,5-dicyano-3-methyl-1,3-dihydro-2H-imidazol-2-one (VI) (m.p. 207°-9° C.).

EXAMPLE 29

Preparation of 1-(4-chloro-2-fluoro-5-methoxyphenyl)-4,5-dicyano-3-methyl-1,3-dihydro-2H-imidazol-2-one 5-Methoxy-2-fluoro-4-chloroaniline (I) (46.4 g, 0.265 mmol), KCN (34.5 g, 0.530 mmol), and paraformaldehyde (15.9 g, 0.530 mmol) were stirred together in 300 mL of acetic acid. Initially, the temperature of the mixture rose on its own to 45° C., then heating was applied to approximately 60° C. and the mixture was stirred for one hour. The mixture was then poured onto water and filtered, leaving a peach colored solid. This material was taken up in ethyl acetate, filtered again, and treated with water and saturated sodium bicarbonate solution. The mixture was then dried, filtered, and evaporated via standard techniques to give 55.6 g of the corresponding arylaminoacetonitrile (IX) (m.p. 133°-4° C.).

To 300 mL of pyridine stirred at 0° C. was added 215 g (280 mmol) of 12.5% phosgene in toluene. The addition produced an exothermic reaction to approximately 25° C. and a yellow solid slurry was formed. The mixture was then cooled to 0° C. and the arylaminoacetonitrile product prepared above (IX) in 225 mL of pyridine was added dropwise and the resulting mixture was stirred for one and one-half hours at 0° C. In one portion was added $CH_3NHCH_2CN \cdot HCl$ (10.5 g, 98 mmol) and the cooling bath was removed and the mixture was stirred overnight at room temperature. The mixture was poured onto dilute HCl solution, extracted three times with 400 mL of ethyl acetate, and the organic layer was washed with dilute HCl until the washings were acidic, then washed with brine. The mixture was then dried over $MgSO_4$, filtered and evaporated, then recrystallized from ethyl acetate/heptane to give 18.8 g of material (X) (m.p. 96°-7° C.).

The material obtained above (X) (10 g, 32.3 mmol) was stirred in 600 mL of $CCl_4$, heated to reflux, and the material went into solution. Heating was removed, and N-bromosuccinimide (NBS) (12.6 g, 71.0 mmol) was added. The solution was treated with a catalytic amount of azobisisobutyronitrile (AIBN), and irradiated with a sun lamp 2.5 hours. The mixture was stirred overnight at room temperature and then filtered and evaporated to give 13.5 g of material, which was taken up in approximately 300 mL of benzene and added dropwise to an ice cold solution of 1,8-diazabicyclo[5,4,0]cycloundec-7-ene (DBU) (10.8 g, 71 mmol) in 300 mL benzene. After addition to DBU was completed, the mixture was stirred one-half hour, then filtered. The filtrate was washed with benzene, then the benzene solution was washed with water, and dried, filtered, and evaporated. The remaining aqueous mixture was washed with ethyl acetate and dried, filtered, and evaporated, then added to the organic material. Recrystallization with ethyl acetate/hexane gave 3.9 g. of 1-(4-chloro-2-fluoro-5-methoxyphenyl)-4,5-dicyano-3-methyl-1,3-dihydro-2H-imidazol-2-one. (VI) (m.p. 163°-4° C.).

The following examples were prepared according to the general procedure of Scheme 2, above.

EXAMPLE 30

1-(4-Bromophenyl)-4,5-dicyano-3-ethyl-1,3-dihydro-2H-imidazol-2-one (VI) (m.p. 124°-6° C.).

EXAMPLE 31

1-(4-Bromo-2-fluoro-5-methoxyphenyl)-4,5-dicyano-3-methyl-1,3-dihydro-2H-imidazol-2-one (VI) (m.p. 181° C.).

EXAMPLE 32

Preparation of 1-(4-chloro-2-fluoro-5-hydroxyphenyl)-4,5-dicyano-3-methyl-1,3-dihydro-2H-imidazol-2-one The product of Example 29, 1-(4-chloro-2-fluoro-5-methoxyphenyl)-4,5-dicyano-3-methyl-1,3-dihydro-2H-imidazol-2-one (VI) (2.7 g, 8.82 mmol) was stirred in 100 mL benzene. To this mixture was added $AlCl_3$ (4.68 g, 35.3 mmol) and the mixture was heated to reflux for 15 minutes. The mixture was cooled to room temperature, poured onto water, and extracted three times with 100 mL ethyl acetate. The organic solution was washed with water and brine, dried over $MgSO_4$, filtered, and evaporated. The crude product was purified by elution from a short silica gel column. Recrystallization with ethyl acetate/heptane gave 1.6 g of 1-(4-chloro-2-fluoro-5-hydroxyphenyl)-4,5-dicyano-3-methyl-1,3-dihydro-2H-imidazol-2-one (VIII) (m.p. 210°-12° C.).

EXAMPLE 33

Preparation of 1-(4-chloro-2-fluoro-5-acetoxyphenyl)-4,5-dicyano-3-methyl-1,3-dihydro-2H-imidazol-2-one The product of Example 32, 1-(4-chloro-2-fluoro-5-hydroxyphenyl)-4,5-dicyano-3-methyl-1,3-dihydro-2H-imidazol-2-one, (VIII) (200 mg, 0.68 mmol) was stirred in 10 mL pyridine at room temperature. To this mixture was added acetic anhydride (100 mg, 0.98 mmol). After stirring for 10 minutes the mixture was poured over a mixture of ice/HCl and filtered. Recrystallization from ethyl acetate/heptane gave 60 mg of 1-(4-chloro-2-fluoro-5-acetoxyphenyl)-4,5-dicyano-3-methyl-1,3-dihydro-2H-imidazol-2-one (VI) (m.p. 164°-6° C.).

EXAMPLE 34

Preparation of
1-(4-chloro-2-fluoro-5-ethoxyphenyl)-4,5-dicyano-3-methyl-1,3-dihydro-2H-imidazol-2-one The product of Example 32, 1-(4-chloro-2-fluoro-5-hydroxyphenyl)-4,5-dicyano-3-methyl-1,3-dihydro-2H-imidazol-2-one, (VIII) (0.7 g, 2.4 mmol) was heated to reflux in 30 mL acetone after the addition of $K_2CO_3$ (0.5 g, 3.6 mmol), then cooled. To this mixture was added ethyl iodide (0.75 g, 4.8 mmol), and the resulting mixture was heated to reflux for four hours. The mixture was cooled, filtered, and evaporated via standard techniques. The residue was taken up in 100 mL ether, filtered, evaporated, and recrystallized from ethyl ether/hexane to give 0 5 g of 1-(4-chloro-2-fluoro-5-ethoxyphenyl)-4,5-dicyano-3-methyl-1,3-dihydro-2H-imidazol-2-one (VI) (m.p. 124°-5° C.).

EXAMPLE 35

Preparation of
1-(4-chloro-2-fluoro-5-methoxymethoxyphenyl)-4,5-dicyano-3-methyl-1,3-dihydro-2H-imidazol-2-one The product of Example 32, 1-(4-chloro-2-fluoro-5-hydroxyphenyl)-4,5-dicyano-3-methyl-1,3-dihydro-2H-imidazol-2-one, (VIII) (200 mg, 0.68 mmol) was stirred in approximately 10 mL of dimethylformamide. To this mixture was added NaH (30 mg of 60% in oil, 0.68 mmol) at room temperature. The resulting mixture began to effervesce and became yellow and turbid. The mixture was then stirred for approximately 15 minutes until the evolution of $H_2$ subsided. To this mixture was then added chloromethyl methyl ether (100 mg, 1.4 mmol) in one portion. The solution immediately decolorized. The mixture was stirred ten minutes at room temperature, poured onto ice/HCl, and extracted three times with 25 ml ethyl acetate. The organic solution was washed with water and brine, dried over $MgSO_4$, filtered, and evaporated via standard techniques. The crude product was purified by elution from a short silica gel column to give 150 mg of 1-(4-chloro-2-fluoro-5-methoxymethoxyphenyl)-4,5-dicyano-3-methyl-1,3-dihydro-2H-imidazol-2-one (VI) as an oil (M.S. M+336).

EXAMPLE 36

Preparation of
1-(4-chloro-2-fluoro-5-(1-methyl-2-propynyloxy)-phenyl)-5-chloro-4-cyano-3-ethyl-1,3-dihydro-2H-imidazol-2-one The product of Example 3, 1-(4-chloro-2-fluoro-5-propargyloxyphenyl)-5-cyano-4-chloro-3-ethyl-1,3-dihydro-2H-imidazole-2-one, (V) (0.65 g, 1.8 mmol) was stirred in 20 mL of $CH_2Cl_2$ at 0° C. To this solution was added $BBr_3$ (3 mL of a 1M solution in $CH_2Cl_2$) dropwise. Stirring was continued at 0° C. for two hours, then the solution was treated with 10 mL of water. Stirring was continued overnight, then the layers were separated and the organic layer was treated with brine, dried ($MgSO_4$), and concentrated via standard techniques. The residue was chromatographed through silica to give approximately 0.2 g of the corresponding dealkylated product (VII) which was treated directly with 3-bromo-2-butyne (0.1 g, 0.7 mmol) and $K_2CO_3$ (0.2 g, 1.4 mmol) in 10 mL of acetone, and the resulting mixture was heated at reflux for six hours. The mixture was then cooled, diluted with 40 mL of ethyl ether, then filtered and concentrated via standard techniques. The residue was chromatographed (25:75 ethyl acetate:petroleum ether) to give 65 mg of 1-(4-chloro-2-fluoro-5-(1-methyl-2-propynyloxy) phenyl)-5-chloro-4-cyano-3-ethyl-1,3-dihydro-2H-imidazole-2-one (V) (m.p. 121°-3° C.).

The following examples were prepared according to the general procedure of Scheme 1B, above.

EXAMPLE 37

1-(4-Chloro-2-fluoro-5-propargyloxyphenyl)-4,5-dicyano-3-methyl-1,3-dihydro-2H-imidazol-2-one (VI) (m.p. 124°-6° C.).

EXAMPLE 38

1-(4-Chloro-2-fluoro-5-allyloxyphenyl)-4,5-dicyano-3-methyl-1,3-dihydro-2H-imidazol-2-one (VI) (m.p. 103°-4° C.).

EXAMPLE 39

1-(4-Chloro-2-fluoro-5-(1-methylethoxy)phenyl)-4,5-dicyano-3-methyl-1,3-dihydro-2H-imidazol-2-one (VI) (m.p. 121°-3° C.).

EXAMPLE 40

1-(4-Chloro-2-fluoro-5-(1-ethoxycarbonylethoxy) phenyl)-4,5-dicyano-3-propyl-1,3-dihydro-2H-imidazol-2-one (VI) (M.S. M+420).

EXAMPLE 41

1-(4-Chloro-2-fluoro-5-(1-ethoxycarbonylethoxy) phenyl)-4,5-dicyano-3-methyl-1,3-dihydro-2H-imidazol-2-one (VI) (M.S. M+392).

EXAMPLE 42

1-(4-Bromo-2-fluoro-5-propargyloxyphenyl)-4,5-dicyano-3-ethyl-1,3-dihydro-2H-imidazol-2-one (VI) (m.p. 101° C.).

EXAMPLE 43

1-(4-Chloro-2-fluoro-5-(1-methyl-2-propynyloxy) phenyl)-4,5-dicyano-3-methyl-1,3-dihydro-2H-imidazol-2-one (VI) (M.S. M+344).

EXAMPLE 44

1-(4-Chloro-2-fluoro-5-difluoromethoxyphenyl)-4,5-dicyano-3-methyl-1,3-dihydro-2H-imidazol-2-one (VI) (M.S. M+342).

EXAMPLE 45

1-(4-Chloro-2-fluoro-5-[(2-methoxyethoxy)-methoxy]-phenyl)-4,5-dicyano-3-methyl-1,3-dihydro-2H-imidazol-2-one (VI) (m.p. 82°-4° C.).

EXAMPLE 46

1-(4-Chloro-2-fluoro-5-methylthiomethoxyphenyl) 4,5-dicyano-3-methyl-1,3-dihydro-2H-imidazol-2-one (VI) (M.S. M+352).

EXAMPLE 47

1-(4-Bromo-2-fluoro-5-(1-methylethoxy) phenyl)-4,5-dicyano-3-methyl-1,3-dihydro-2H-imidazol-2-one (V) (m.p. 147° C.).

EXAMPLE 48

Preparation of
1-(4-chlorophenyl)-4,5-dicyano-3-benzyl-1,3-dihydro-2H-imidazol-2-one Powdered p-chloroaniline (I) (2.2 g, 17.3 mmol) was added to a solution of lithium diisopropylamide (from 3.67 g, 36.3 mmol, of diisopropylamine, and 17.3 mL of 2.1M butyllithium) in 50 mL of tetrahydrofuran (THF) at approximately −65° C. and the solution was allowed to warm briefly to approximately −40° C., then the solution was cooled to −78° C. 2-((N-ethoxycarbonyl)-benzylamino)-3-methylthiomaleonitrile (2.6 g, 8.6 mmol) in 50 mL THF was added dropwise and the mixture was stirred for one-half hour at −78° C., then poured onto a mixture of ice/HCl. The mixture was extracted with ethyl acetate, washed with water, then dried, filtered and evaporated. To the residue was added N-methylpyrrolidone (100 mL) and the mixture was heated to reflux one-half hour. The mixture was cooled, poured onto water, extracted three times with 100 mL of ethyl acetate, dried, filtered, and evaporated via standard techniques. Isolation by chromatography then recrystallization from ethyl acetate/heptane gave 1.2 g of 1-(4-chlorophenyl)-4,5-dicyano-3-benzyl-1,3-dihydro-2H-imidazol-2-one (XIII) (m.p. 192°-4° C.).

EXAMPLE 49

Preparation of
1-(4-chlorophenyl)-4,5-dicyano-1,3-dihydro-2H-imidazol-2-one

The product of Example 48, 1-(4-chlorophenyl)-4,5-dicyano-3-benzyl-1,3-dihydro-2H-imidazol-2-one, (XIII) (1.2 g, 3.6 mmol) was stirred in 50 mL of benzene. To this solution was added $AlCl_{13}$ (1.9 g, 14.4 mmol) and the mixture was heated to reflux for one-half hour. The mixture was then poured onto water and extracted with ethyl acetate, then dried, filtered and evaporated via standard techniques. The residue was recrystallized from ethyl acetate/heptane to give 0.72 g of 1-(4-chlorophenyl)-4,5-dicyano-1,3-dihydro-2H-imidazol-2-one (XIV) (m.p. 242°-5° C.).

EXAMPLE 50

Preparation of
1-(4-chlorophenyl)-4,5-dicyano-3-difluoromethyl-1,3-dihydro-2H-imidazol-2-one The product of Example 49, 1-(4-chlorophenyl)-4,5-dicyano-1,3-dihydro-2H-imidazol-2-one, (XIV) (300 mg, 1.34 mmol) was stirred in 25 mL of dimethylformamide at room temperature. To this mixture was added 1 equivalent of NaH (53 mg, 1.34 mmol), and the resulting mixture was stirred one-half hour. The mixture was then heated while bubbling through excess $CClF_2H$ for approximately 15 minutes at 70° C., then a dry ice/acetone condenser was attached and heating was continued for approximately four hours at 70° C. The mixture was then poured on ice/HCl and extracted with ethyl ether, dried, filtered, and evaporated via standard techniques. Purification by eluting from a short silica gel column gave 180 mg of 1-(4-chlorophenyl)-4,5-dicyano-3-difluoromethyl-1,3-dihydro-2H-imidazole-2-one (VI) (m.p. 167°-8° C.).

EXAMPLE 51

Preparation of
1-(4-chlorophenyl)-4,5-dicyano-3-cyanomethyl-1,3-dihydro-2H-imidazol-2-one The product of Example 49, 1-(4-chlorophenyl)-4,5-dicyano-1,3-dihydro-2H-imidazol-2-one, (200 mg, 0.82 mmol) was stirred in 25 mL of dimethylformamide at room temperature. To this solution was added NaH (65 mg of 60% in oil, 1.6 mmol) and the resulting mixture was stirred for one hour. To this mixture was added chloroacetonitrile (250 mg, 3.2 mmol) and stirring was continued for ten days. The mixture was poured onto ice/HCl and extracted with ethyl acetate. Isolation by chromatography and recrystallization from ethyl acetate/heptane gave 90 mg of 1-(4-chlorophenyl)-4,5-dicyano-3-cyanomethyl-1,3-dihydro-2H-imidazol-2-one (VI) (m.p. 169°-71° C.).

The following example was prepared according to the general procedure of Example 51, above.

EXAMPLE 52

1-(4-Chlorophenyl)-4,5-dicyano-3-(prop-2-yn-1-yl)-1,3-dihydro-2H-imidazol-2-one (m.p. 146° C.).

EXAMPLE 53

Preparation of
2-(4-chloro-2-fluoro-5-methoxyphenyl)-2,3,5,6,7,8-hexahydro-3-oxoimidazo[1,5-a]pyridine-1-carbonitrile N-(2-fluoro-4-chloro-5-methoxyphenyl) aminoacetonitrile, prepared as described in Example 29, (29 g, 0.135 mol) in 150 mL of dioxane was treated with 207 mL of a 1.3M solution of phosgene in toluene (0.27 mol), and the solution was heated on a steam bath for three hours. After removal of the solvent, the residue was combined with 200 mL of toluene, 24 ml (0.17 mol) of TEA and 14.7 g (0.148 mol) of Y-valerolactam, and the mixture was heated on a steam bath overnight. The solution was then cooled and combined with 200 mL of 2N HCl and the product was extracted into 200 mL of ethyl acetate. The organic layer was washed with brine, dried, and concentrated. Recrystallization of the solid residue furnished 35.7 g of urea (m.p. 138° C.). To the above product (7 g, 0.021 mol) in 40 mL of dimethylformamide at 0° C. was added 1.6 g (0.04 mol) of sodium hydride (60% in oil) portion wise, and the solution was stirred at that temperature for one hour. The mixture was then poured onto ice and 100 mL of 1N HCl, and stirred for 30 minutes. The product was then filtered to furnish a solid, which was recrystallized from toluene/hexane to yield 4.4 g of 2-(4-chloro-2-fluoro-5-methoxyphenyl)-2,3,5,6,7,8-hexahydro-3-oxoimidazo[1,5-a]pyridine-1-carbonitrile (XXI) (m.p. 173°-5° C.). An additional 0.5 g of product was obtained by concentration of the mother liquors and recrystallization from toluene-hexane.

The following examples were prepared according to the general procedure described in Example 53, above.

EXAMPLE 54

2-(4-Chloro-2-fluorophenyl)-2,3,5,6,7,8-hexahydro-3-oxoimidazo[1,5-a]pyridine-1-carbonitrile (m.p. 100° C.).

EXAMPLE 55

2-(4-Chlorophenyl)-2,3,5,6,7,8-hexahydro-3-oxoimidazo[1,5-a]pyridine-1-carbonitrile (m.p. 167°-9° C.).

EXAMPLE 56

2-(2,4-Dichlorophenyl)-2,3,5,6,7,8-hexahydro-3-oxo-5H-imidazo-[1,5-a]pyridine-1-carbonitrile (m.p. 127°–9° C.).

EXAMPLE 57

Preparation of
2-(4-chloro-2-fluoro-5-hydroxyphenyl)-2,3,5,6,7,8-hexahydro-3-oxoimidazo[1,5-a]pyridine-1-carbonitrile The product of Example 53, 2-(4-chloro-2-fluoro-5-methoxyphenyl)-2,3,5,6,7,8-hexahydro-3-oxoimidazo[1,5-a]pyridine-1-carbonitrile, (4 g, 0.012 mol) was dissolved in benzene and treated with 8.3 g (0.062 mol) of AlCl₃ using conditions described in Example 32 to furnish 3.1 g of 2-(4-chloro-2-fluoro-5-hydroxyphenyl)-2,3,5,6,7,8-hexahydro-3-oxoimidazo[1,5-a]pyridine-1-carbonitrile (m.p. 204°–6° C.).

EXAMPLE 58

Preparation of
2-(4-chloro-2-fluoro-5-propargyloxyphenyl)-2,3,5,6,7,8-hexahydro-3-oxoimidazo[1,5-a]pyridine-1-carbonitrile The product of Example 57, 2-(4-chloro-2-fluoro-5-hydroxyphenyl)-2,3,5,6,7,8-hexahydro-3-oxoimidazo[1,5-a]pyridine-1-carbonitrile (2.6 g, 0.0085 mol) was treated with 1.5 g (0.010 mol) of an 80% solution of propargyl bromide in toluene and 1.4 g (0.01 mol) of potassium carbonate in refluxing acetone, as described in Example 34, to furnish, after recrystallization from ethanol, 2.2 g of 2-(4-chloro-2-fluoro-5-propargyloxyphenyl)-2,3,5,6,7,8-hexahydro-3-oxoimidazo[1,5-a]pyridine-1-carbonitrile (XXI) (m.p. 166°–8° C.).

The following examples were prepared according to the general procedure described in Example 58, above.

EXAMPLE 59

2-(4-Chloro-2-fluoro-5-(cyanomethoxy)phenyl)-2,3,5,6,7,8-hexahydro-3-oxoimidazo[1,5-a]pyridine-1-carbonitrile (m.p. 180°–2° C.)

EXAMPLE 60

2-(4-Chloro-2-fluoro-5-(1-ethoxycarbonyl-ethoxy)-phenyl)-2,3,5,6,7,8-hexahydro-3-oxoimidazo[1,5-a]pyridine-1-carbonitrile (M.S. M+407).

EXAMPLE 61

2-(4-Chloro-2-fluoro-5-(1-ethoxycarbonyl-methoxy)-phenyl)-2,3,5,6,7,8-hexahydro-3-oxoimidazo[1,5-a]pyridine-1-carbonitrile (M.S. M+393)

EXAMPLE 62

Preparation of
2-(4-chlorophenyl)-2,3,6,7-tetrahydro-3-oxo-5H-pyrrolo-[1,2-c]imidazol-1-carbonitrile.

N-(4-chlorophenyl)-N-cyanomethylcarbamoyl chloride, prepared as described in Example 53, (2.7 g, 0.012 mol) was dissolved in 10 mL of dimethylformamide and added dropwise to a cold solution (0° C.) of 2-pyrrolidinone (1.0 g, 0.012 mol) and sodium hydride (0.96 g, 0.024 mol) in 20 mL of DMF. The solution was allowed to warm to ambient temperature over two hours, then it was poured onto ice water and extracted with ethyl acetate. The organic layer was washed with saturated brine solution, dried over magnesium sulfate, and concentrated to yield an oil. Elution of this oil through a silica gel column using 1:2 ethyl acetate:hexane furnished 0.4 g of 2-(4-chlorophenyl)-2,3,6,7-tetrahydro-3-oxo-5H-pyrrolo-[1,2-c]imidazol-1-carbonitrile, as a solid (m.p. 154°–6° C.).

EXAMPLE 63

Preparation of
2-(4-chloro-2-fluoro-5-methoxyphenyl)-2,3,6,7,8,9-hexahydro-3-oxo-5H-imidazo[1,5-a]azepine-1-carbonitrile N-(2-fluoro-4-chloro-5-methoxyphenyl) aminoacetonitrile, prepared as described in Example 29 (1.8 g, 0.084 mol), was treated with phosgene and ε-caprolactam, using conditions described in Example 53, to furnish 1.9 g of the urea (XX). The urea was then dissolved in 15 mL of tetrahydrofuran, cooled to −60° C., and treated successively with diisopropylamine (0.8 g, 0.008 mol) and butyllithium (4 mL of a 2.01M solution in hexane, 0.008 mol). After the solution had stirred for two hours, it was poured over 100 mL of an ice cold 1N HCl solution, extracted with ethyl acetate, washed with saturated brine solution, dried, and concentrated in vacuo to give a solid residue. Recrystallization from ethyl acetate-hexane gave 0.8 g of 2-(4-chloro-2-fluoro-5-methoxyphenyl)-2,3,6,7,8,9-hexahydro-3-oxo-5H-imidazo[1,5-a]azepine-1-carbonitrile (m.p. 144°–6° C.).

EXAMPLE 64

2-(4-Chlorophenyl)-2,3,6,7,8,9-hexahydro-3-oxo-5H-imidazo[1,5-a]azepine-1-carbonitrile (m.p. 149°–51° C.).

EXAMPLE 65

Preparation of
2-(4-chloro-2-fluoro-5-propargyloxyphenyl)-2,3,6,7,8,9-hexahydro-3-oxo-5H-imidazo[1,5-a]azepine-1-carbonitrile The product of Example 6, 2-(4-chloro-2-fluoro-5-methoxyphenyl)-2,3,6,7,8,9-hexahydro-3-oxo-5H-imidazo[1,5-a]azepine-1-carbonitrile (0.68 g, 2 mmol) was treated with 1.3 g (10.1 mmol) of AlCl₃ using conditions described in Example 58, to furnish 0.6 g of 2-(4-chloro-2-fluoro-5-hydroxyphenyl)-2,3,6,7,8,9-hexahydro-3-oxo-5H-[1,5-a]azepine-1-carbonitrile. A portion of this material (0.3 g, 0.93 mmol) was treated with 0.17 g (1.12 mmol) of an 80% solution of propargyl bromide in toluene and 0.15 g (1.40 mmol) of potassium carbonate in refluxing acetone, as described in Example 34, to furnish, after recrystallization from ethanol, 0.25 g of 2-(4-Chloro-2-fluoro-5-propargyloxyphenyl)-2,3,6,7,8,9-hexahydro-3-oxo-5H-imidazo[1,5-a]azepine-1-carbonitrile (XXI) (m.p. 148°–150° C.).

EXAMPLE 66

Preparation of
1-(4-chlorophenyl)-5-bromo-4-cyano-3-methyl-1,3-dihydro-2H-imidazol-2-one A stirred solution of 2.2 g (0.072 mol) of 1-(4-chlorophenyl)-4-cyano-5-ethoxycarbonyl-3-methyl-1,3-dihydro-2H-imidazol-2-one, prepared from ethyl p-chlorophenylaminoacetate according to the procedure described in Example 29, was dissolved in 25 mL of ethanol and 5 mL of water. Sodium hydroxide (0.3 g, 0.075 mol) was added to the solution, which was then allowed to stir at ambient temperature for thirty minutes. After concentration in vacuo to 5 mL volume, the material was diluted with 50 mL of water, washed with ether, and acidified using concentrated HCl. The precipitated solid was collected and air-dried to give 1.2 g of the carboxylic acid (m.p. 260° C., dec).

The acid (0.8 g, 2.9 mmol) was dissolved in 10 mL of dimethylformamide and treated successively at ambient temperature with 0.58 g of potassium bisulfate (0.0058 mol) and 0.64 g of N-bromsuccinimide (3.6 mmol). After allowing the solution to stir an additional 60 minutes, it was poured onto 75 mL of water. The solidified product was filtered and air-dried, then recrystallized from ethyl acetate-petroleum ether to furnish 0.5 g of 1-(4-chlorophenyl)-5-bromo-4-cyano-3-methyl-1,3-dihydro-2H-imidazol-2-one (m.p. 185° C.).

EXAMPLE 67

Preparation of
1-(4-chlorophenyl)-4-cyano-5-fluoro-3-methyl-1,3-dihydro-2H-imidazol-2-one A solution of the product of Example 66, 1-(4-chlorophenyl)-5-bromo-4-cyano-3-methyl-1,3-dihydro-2H-imidazol-2-one (0.4 g, 1.3 mmol) and potassium fluoride (0.14 g, 2.66 mmol) in 100 mL of dry dimethyl sulfoxide was heated to 130° C. for two hours, then cooled and poured into 100 mL of water. The product was extracted into ethyl acetate, washed with saturated brine solution, dried, and concentrated to an oil. The oil was chromatographed through silica gel (25:75 ethyl acetate:petroleum ether). Collection of the appropriate fractions furnished 0.14 g of 1-(4-chlorophenyl)-4-cyano-5-fluoro-3-methyl-1,3-dihydro-2H-imidazol-2-one (m.p. 105° C.).

EXAMPLE 68

Preparation of
1-(4-chlorophenyl)-3,4-dimethyl-5-cyano-1,3-dihydro-2H-imidazol-2-one A solution of N-(4-chlorophenyl) aminoacetonitrile (7 g, 42 mmol), prepared as described in Example 29, and methyl isocyanate (4 g, 70 mmol) in 100 mL of toluene was heated to reflux for 16 hours. The solution was then cooled and concentrated in vacuo, and the solid residue was recrystallized from ethyl acetate-petroleum ether to give 7 g of urea (m.p. 109° C.). A portion of the urea (2.5 g, 11.2 mmol) was dissolved in 20 mL of acetic anhydride, and 4 drops of concentrated sulfuric acid were added. The solution was heated to reflux for four hours, then cooled and concentrated in vacuo. The residue was chromatographed on silica gel to furnish 2.7 g of the acylated urea (M+265). A portion of this product (2.5 g, 10 mmol) was dissolved in 50 mL of tetrahydrofuran and treated with diazabicycloundecene (3.04 g, 10 mmol). The solution was heated at reflux for three hours, then cooled and concentrated in vacuo. The residue was partitioned between ethyl acetate and 1N HCl, and the organic layer was dried, concentrated, and chromatographed on silica gel to furnish 1.45 g of 1-(4-chlorophenyl)-3,4-dimethyl-5-cyano-1,3-dihydro-2H-imidazol-2-one (m.p. 138°-140° C.).

The following examples were prepared according to the general procedure described in Example 68, above.

EXAMPLE 69

1-(2,4-Dichlorophenyl)-3,4-dimethyl-5-cyano-1,3-dihydro-2H-imidazol-2-one (M+281).

EXAMPLE 70

1-(4-chlorophenyl)-3-methyl-5-cyano-1,3-dihydro-2H-imidazol-2-one (XVI) (m.p. 149°-151° C.) was prepared by the general procedure of Example 68, except acetic anhydride was replaced by acetic formic anhydride and the sulfuric acid catalyst was omitted.

EXAMPLE 71

1-(4-Chloro-2-fluoro-5-methoxyphenyl)-3-methyl-4,5-dicyano-4-hydroxy-tetrahydro-2H-imidazol-2-one (M.S. M+324). [58 ]

EXAMPLE 72

Preparation of
1-(4-bromo-2-fluoro-5-methoxyphenyl)-3-difluoromethyl-4,5-dicyano-1,3-dihydro-2H-imidazol-2-one 4-Bromo-2-fluoro-5-methoxyaniline (I) was converted to the isothiocyanate using standard conditions. (See, for example, Kim and Yi, *J. Org. Chem.* 51 [1986]2615). The isothiocyanate (1.96 9, 7.5 mmol) was added over three minutes to a stirred and cooled (5° C.) solution of diphenyliminoacetonitrile (1.67 g, 7.6 mmol) and sodium hydride (0.7 g of 60%, 17.4 mmol) in 20 mL of dimethylformamide. After an additional 30 minutes at that temperature, methyl iodide (2.5 g, 17.6 mmol) was added dropwise and stirring was continued an additional 30 minutes. The semisolid mixture was then poured onto ice and the solution was made acidic with 1N HCl. A yellow solid formed, and was filtered and air-dried. The solid was taken up in 10 mL of dry dimethylformamide and treated with 1 g (15 mmol) of powdered potassium cyanide. The solution was heated on a steam bath for one hour, then cooled and poured onto water. The product was extracted into ethyl ether, dried, and concentrated to an oil, which was chromatographed to remove unreacted starting material and impurities. Elution with 25% ethyl acetate-petroleum ether furnished 0.6 g of the dicyano intermediate, which was treated directly with 5 mL of 1N HCl and 15 mL of ethanol at steam bath temperature for 30 minutes. The solution was then cooled and concentrated in vacuo, then chromatographed over a short silica gel column to remove benzophenone.

The residue (0.20 g, 0.64 mmol) was dissolved in 10 mL of dioxane and treated with 0.2 g (6.7 mmol) of triphosgene with heating on a steam bath for three hours. The solution was then cooled and concentrated, then eluted through a short silica gel column. Elution with 50% ethyl acetate-petroleum ether gave 0.1 g of the dicyanoimidazolidinone. This material was then taken up in 25 mL of dry tetrahydrofuran and treated with 0.2 g of 20% potassium hydride (1 mmol). The solution was saturated with chlorodifluoromethane and heated to reflux for eight hours, using a dry ice-acetone condenser. After the solution had cooled, it was poured onto 50 mL of ice and water, and the product extracted into ethyl acetate. The organic layer was washed with saturated brine solution, dried, and concentrated to yield an oil, which was chromatographed (25% ethyl acetate-petroleum ether). The product-containing fractions were combined and concentrated to give 18.5 mg of 1-(4-bromo-2-fluoro-5-methoxyphenyl)-3-difluoromethyl-4,5-dicyano-1,3-dihydro-2H-imidazole-2-one (m.p. 150° C.).

The following example was prepared according to the general procedure described in Example 72, above:

EXAMPLE 73

1-(4-Chloro 2-fluoro-5-methoxyphenyl)-3-difluoromethyl-4,5-dicyano-1,3-dihydro-2H-imidazol-2-one (m.p. 166° C.)

The following example was prepared according to the general procedure described in Example 48, above:

EXAMPLE 74

1-(4-Chloro-2-fluorophenyl)-3-benzyl-4,5-dicyano-1,3-dihydro-2H-imidazol-2-one (m.p. 161°-3° C.)

The following example was prepared according to the general procedure described in Example 49, above:

EXAMPLE 75

1-(4-Chloro-2-fluorophenyl)-4,5-dicyano-1,3-dihydro-2H-imidazol-2-one (m.p. 149 151° C.)

The following example was prepared according to the general procedure described in Example 50, above:

EXAMPLE 76

1-(4-Chloro-2-fluorophenyl)-4,5-dicyano-3-difluoromethyl-1,3-dihydro-2H-imidazol-2-one (m.p. 100° C.).

EXAMPLE 77

Preparation of 1-(4-chloro-2-fluoro-5-nitrophenyl)-4,5-dicyano-3-difluoromethyl-1,3-dihydro-2H-imidazol-2-one.

The product of Example 76, 1-(4-chloro-2-fluorophenyl)-4,5-dicyano-3-difluoromethyl-1,3-dihydro-2H-imidazol-2-one, (920 mg, 2.9mmol) was dissolved in 15 mL of concentrated sulfuric acid, and this solution was stirred and treated at 0° C. with 0.30 g (3.3 mmol) of 70% nitric acid solution. After one hour, the solution was poured onto 50 g of ice, then the precipitated solid was filtered and air-dried to furnish 1.05 g of 1-(4-chloro-2-fluoro-5-nitrophenyl)-4,5-dicyano-3-difluoromethyl-1,3-dihydro-2H-imidazol-2-one (VI) (m.p. 150° C.).

EXAMPLE 78

Preparation of 1-(5-amino-4-chloro-2-fluorophenyl)-4,5-dicyano-3-difluoromethyl-1,3-dihydro-2H-imidazol-2-one The product of Example 77, 1-(4-chloro-2-fluoro-5-nitrophenyl)-4,5-dicyano-3-difluoromethyl-1,3-dihydro-2H-imidazol-2-one, (1.05 g, 2.9 mmol) was dissolved in 10 mL of glacial acetic acid and added dropwise to a stirred solution of iron powder (1 g, 17.9 g-atom) in 5 mL of water. The solution was stirred two hours maintaining the reaction temperature below 35° C. with the aid of a cold water bath. The solution was then diluted with 50 mL of ether and filtered. The filtrate was washed with 3x 50 mL of water, then dried and concentrated via standard techniques to furnish 0.70 g of 1-(5-amino-4-chloro-2-fluorophenyl)-4,5-dicyano-3-difluoromethyl-1,3-dihydro-2H-imidazol-2-one (VI) (m.p. 155°-6° C.).

EXAMPLE 79

Preparation of 1-(4-chloro-2-fluoro-5-bis(methanesulphonyl) amino-phenyl)-4,5-dicyano-3-difluoromethyl-1,3-dihydro-2H-imidazol-2-one.

The product of Example 77, 1-(4-chloro-2-fluoro-5-nitrophenyl)-4,5-dicyano-3-difluoromethyl-1,3-dihydro-2H-imidazol-2-one, (0.7 g, 2.1 mmol) was dissolved in dichloromethane and treated sequentially at 0° C. with triethylamine (0.56 g, 5.5 mmol) and methanesulphonyl chloride (0.56 g, 5 mmol). The solution was allowed to stir 16 hours at ambient temperature, then poured onto 10 mL of 1N hydrochloric acid solution. The organic layer was separated, washed with brine, and dried and concentrated via standard techniques to furnish 1 g of 1-(4-chloro-2-fluoro-5-bis(methanesulphonyl) amino-phenyl)-4,5-dicyano-3-difluoromethyl-1,3-dihydro-2H-imidazol-2-one (VI) (M.S. M+483).

EXAMPLE 80

Preparation of 1-(4-chloro-2-fluoro-5-methanesulphonylaminophenyl) -4,5-dicyano-3-difluoromethyl-1,3-dihydro-2H-imidazol-2-one The product of Example 77, 1-(4-chloro-2-fluoro-5-nitrophenyl)-4,5-dicyano-3-difluoromethyl-1,3-dihydro-2H-imidazol-2-one, (0.7 g, 2.1 mmol) is dissolved in dichloromethane and treated sequentially at 0° C. with triethylamine (0.27 g, 2.8 mmol) and methanesulphonyl chloride (0.28 g, 2.5 mmol). The solution is allowed to stir 16 hours at ambient temperature, then poured onto 10 mL of 1N hydrochloric acid solution. The organic layer is separated, washed with brine, and dried and concentrated via standard techniques to furnish 1-(4-chloro-2-fluoro-5-methanesulphonylaminophenyl) -4,5-dicyano-3-difluoromethyl-1,3-dihydro-2H-imidazol-2-one (VI).

EXAMPLE 81

Preparation of 1-(5-N-acetylamino-4-chloro-2-fluorophenyl)-4,5-dicyano-3-difluoromethyl-1,3-dihydro-2H-imidazol-2-one The product of Example 79, 1-(4-chloro-2-fluoro-5-bis(methanesulphonyl)amino-phenyl)-4,5-dicyano-3-difluoromethyl-1,3-dihydro-2H-imidazol-2-one, (0.7 g, 2.1 mmol) is dissolved in dichloromethane and treated sequentially at 0° C. with triethylamine (0.27 g, 2.8 mmol) and acetyl chloride (0.2 g, 2.5 mmol). The solution is allowed to stir 16 hours at ambient temperature, then poured onto 10 mL of 1N hydrochloric acid solution. The organic layer is separated, washed with brine, and dried and concentrated via standard techniques to furnish 1-(5-N-acetylamino-4-chloro-2-fluorophenyl)-4,5-dicyano-3-difluoromethyl-1,3-dihydro-2H-imidazol-2-one (VI).

The following example was prepared according to the general procedure described in Example 53, above.

EXAMPLE 82

2-(4-Chloro-2-fluorophenyl)-octahydro-8a-hydroxy-3-oxoimidazo[1,5-a]pyridine-1-carbonitrile was prepared from 4-chloro-2-fluorophenylaminoacetonitrile (IX) according to the general procedure of Example 53, except in the final workup, the acid wash resulting in dehydration was replaced with a neutral workup to deliver the intermediate (XVII) (m.p. 155°-7° C.).

EXAMPLE 83

2-(4-Chloro-5-ethoxycarbonyl-2-fluorophenyl)-2,3,5,6,7,8-hexahydro-3-oxo-2H-imidazo[1,5-a]pyridine-1-carbonitrile was prepared from ethyl-5-amino-4-chloro-2-fluorobenzoate (M.S. M+363) according to the general procedure described in Example 53, above. [81]

EXAMPLE 84

6-(1-Cyano-2,3,5,6,7,8-tetrahydro-3-oxo-2H-imidazo[1,5-a]pyridin-2-yl)-5-fluoro-1-propargyl-2-oxo-2(3H)-benzothiazol-2-one is prepared from 6-amino-5-fluoro-1-propargyl-2-oxo-2(3H)-benzothiazol-2-one (for preparation, see Japanese AP JP86/1172 960106)) according to the general procedure described in Example 53, above.

EXAMPLE 85

Preparation of
1-(4-Chlorophenyl)-5,6-dicyano-3-methyl-2,4(1H,3H)-pyrimidinedione Ethyl cyanoacetate (10 g, 88.4 mmol) was stirred at 0° C. while 40% aqueous methylamine (45 mL, 530 mmol) was added dropwise. The mixture was allowed to stir with warming to room temperature over the next 16 hours. Solvent was removed in vacuo and several portions of toluene were added and removed in vacuo to remove the last traces of water. Recrystallization from chloroform furnished N-methylcyanoacetamide (XXV, $R\alpha C_3$). A portion of this material (5.0 g, 51 mmol) was dissolved in 100 mL of DMF and stirred at 0° C. while sodium hydride (60%, 2.1 g, 54 mmol) was added portionwise. The mixture was stirred for one hour, then carbon disulphide (4.3 g, 56 mmol) in 25 mL of DMF was added dropwise to the cold reaction mixture. The solution was stirred for an additional one hour, then an additional 2.1 g of sodium hydride (60%, 2.1 g, 54 mmol) was then added portionwise and the mixture was stirred for one hour. Methyl iodide (16 g, 112 mmol) was then added dropwise over five minutes. After an additional 30 minutes, the reaction mixture was poured onto ice-cold, dilute hydrochloric acid, then extracted into ethyl acetate, and the organic phase is washed with water and brine, dried and concentrated via standard techniques to furnish, after recrystallization from ethyl acetate/heptane, 6.84 g of XXVI (R=CH3), m.p. 93°–5° C. A portion of this material (2.0 g, 10 mmol) was combined with 4-chloroaniline (1.26 g, 10 mmol) in 50 mL of 5:1 methanol:water and heated at reflux for 72 hours. The solution was cooled, poured onto ice-cold, dilute hydrochloric acid solution, and the solid product was collected via filtration to furnish 1.63 g of XXVII (X=H, Z=H, Y=Cl, and R=CH3), m.p. 178°–180° C. A portion of this material (1.4 g, 5 mmol) was combined with KCN (1 g, 15 mmol) in 25 mL DMF and stirred at room temperature for 16 hours. The mixture was poured onto water, extracted into ethyl acetate, washed with water and brine, dried and concentrated via standard techniques, then eluted through silica gel to furnish after recrystallization from ethyl acetate/petroleum ether, 0.77 g of XXVIII (X=H, Z=H, Y=Cl, and R=CH3), m.p. 191°–2° C. A portion of this material (0.8 g, 3 mmol) is stirred in 40 mL of toluene at room temperature while triethylamine (1.0 g, 10 mmol) and ethyl chloroformate (0.65 g, 6 mmol) are added consecutively to the solution. The mixture is then stirred for one hour at room temperature and then heated to reflux for two hours. The crude mixture is then further heated in an organic solvent, such as DMF to effect ring closure to deliver 1-(4-chlorophenyl)-5,6-dicyano-3-methyl-2,4(1H,3H)-pyrimidinedione (XXIX).

The compounds of the present invention have been found to exhibit useful preemergent and post emergent activity against a variety of weed species. These weed species commonly occur in cropland areas utilized for growing desired crops, such as, for example, corn, soybeans, wheat, barley, rice, and the like. Also included within the scope of this invention is the non-cropland use of the compounds of the present invention in industrial vegetative control, such as, along fences, roadways, railroad tracks, etc. The selective herbicidal activity of representative compounds of Formula A have been analyzed in standard greenhouse tests. One such test, a broad spectrum test, whereby various representative compounds of Formula A were evaluated at various application rates in a multiple species greenhouse test, was performed in the following manner:

TEST 1

The initial screen used to evaluate herbicidal efficacy, was conducted at a test compound concentration of 8 lb/A (9 kg/ha). In this test tomato, large crabgrass and pigweed seeds were planted by row in containers containing standard growing media.

The test compounds were formulated for application by dissolving the compound into a solvent prepared by combining TOXIMUL R and TOXIMUL S (proprietary blends of anionic and nonionic surfactants manufactured by Stepan Chemical Company, Northfield, Ill.) with a 9:1 (v/v) mixture of acetone:ethanol. The solvent/compound solution was diluted with deionized water and applied postemergence to some planted containers and preemergence to others using a compressed air sprayer at low pressure. Postemergence treatment was made 8 to 10 days after planting while preemergence treatment was made 1–2 days after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury, and "5" indicated death to the plant or no seedling emergence. A "0" indicates that no reading was taken.

The herbicidal activity of some of the compounds of the present invention was further evaluated at various application rate is a multiple species greenhouse test described below.

Method:

Growing Medium: The growing medium for preemergence surface applied treatments is a 1:1 mixture of top soil of medium texture, 2–3% organic matter content, and coarse sand. The medium for postemergence treatments is an artificial soil composed of vermiculite, sphagnum peat moss, processed bark, granite sand, and supplemental nutrients (Metro-Mix 360, W. R. Grace and Co.).

Container and Planting: All plantings are made in plastic or galvanized pans (flats), approximately 31.5 cm long, 21.5 cm wide, and 8.0 cm deep. Calculated surface area is 0.72 sq. ft. The bottoms of the flats have holes to facilitate drainage. The planting procedure starts by filling a flat two-thirds full with growing medium (approximately 5 cm deep). The medium is then leveled and tamped firm. Two flats are prepared for each compound rate. Seeds of the indicator species are planted in rows parallel to the long axis of the flat, one species per half row. Species which may be used in each test are as follows:

| Name | Abbreviation |
| --- | --- |
| Barley (*Hordeum vulgare*) | Brly |
| Corn (*Zea mays*) | Corn |
| Rice (*Oryza sativa*) | Rice |
| Wheat (*Triticum aestivum*) | Whet |
| Foxtail Millet (*Seteria italica*) | FtMi |
| Large Crabgrass (*Digitaria sanguinalis*) | LaCg |
| Wild Oat (*Avena fatua*) | WiOa |
| Cotton (*Gossypium hirsutum*) | Cttn |
| Soybean (*Glycine max*) | Sybn |
| Sugarbeet (*Beta vulgaris*) | Sgbt |
| Lambsquarter (*Chenopodium album*) | Lmqr |
| Jimsonweed (*Datura stramonium*) | Jmwd |
| Morningglory (*Ipomoea sp.*) | Mngy |
| Mustard (*Brassica sp.*) | Mstd |
| Redroot Pigweed (*Amaranthus retroflexus*) | RdPw |
| Tomato (*Lycopersicon esculentum*) | Tmto |
| Velvetleaf (*Abutilon Theophrasti*) | Vele |

The seeds are covered with approximately 1 cm of growing medium. Flats prepared for postemergence treatment are planted 8 to 11 days prior to treatment and placed in a growth chamber under artificial lighting. Environmental conditions are a 12 to 18 hour day length and 75° F. to 85° F. temperature. Preemergent test flats are planted 1 to 2 days prior to treatment.

Formulation: Each compound (30 mg per type application) is dissolved in acetone and ethanol (1:1) containing a small amount of Toximul-R and Toximul-S (3:2) surfactants. The solution is diluted with deionized water to 12.5 mL for preemergence-only or postemergence-only applications, or 25 mL for preemergence and postemergence applications. After dilution with deionized water, concentrations in the stock solution are as follows:

| Test Compound | 0.2% |
| --- | --- |
| Acetone | 4.0% |
| Ethanol | 4.0% |
| Toximul R and S (combined) | 0.2% |
| Deionized Water | 91.6% |
| | 100.0% |

Treatment: The formulated compounds are applied with a compressed air sprayer operated at low pressure. The formulation is applied uniformly over the soil surface (preemergence) or over the foliage of plants (postemergence). Each flat receives 12.5 mL of the formulation, equal to 200 gallons per acre (gpa). Each compound is generally applied at different rates. The rates of application may be 0.5, 1.0, 2.0, or 4.0 lb/A. If the level of activity at 0.5 lb/A is substantial, then the compound may be retested at 0.06, 0.12, 0.25, or 0.5 lb/A under the same method. Preemergence flats are top-watered shortly after treatment. Both preemergence and postemergence treated flats are moved to a greenhouse equipped with supplemental lighting and watered as needed until ready for evaluation.

Evaluation: Preemergence applications are evaluated 18 to 21 days after treatment. Postemergence applications are evaluated 12 to 14 days after treatment. Each species per treatment is evaluated according to plant response and type of injury as follows:

Plant Response Scale:
0 = Evaluation not performed
1 = No injury or effect
2 = Slight injury
3 = Moderate injury
4 = Severe injury
5 = Death of all plants Type of Injury:
A = Leaf abscission
B = Burning
C = Chlorosis
D = Death
E = Epinasty
F = Formative effects
G = Dark green color
I = Increased growth
N = No emergence
P = Purple pigmentation
R = Reduced emergence
S = Stunting
Z = Increased branching The results obtained were as follows:

PREEMERGENCE

| Cmpd No. | Rate (lb./A) | Brly | Corn | Rice | Wheat | FtMi | LaCg | WiOa | Cttn | Sybn | Sgbt | Lmqr | Jiwe | Mngy | Mstd | RrPw | Tmto | Vele |
|---|---|---|---|---|---|---|---|---|---|---|---|---|---|---|---|---|---|---|
| 1 | 4.00 | 2SB | 0 | 0 | 0 | 5D | 5D | 0 | 0 | 2S | 0 | 0 | 0 | 4RBS | 5D | 5D | 5D | 0 |
|  | 2.00 | 3BS | 4BS | 3BS | 2BS | 5D | 5D | 4BS | 2BS | 2BS | 4BS | 5D | 5D | 5D | 5D | 4BS | 5D | 5D |
|  | 1.00 | 2BS | 3BS | 2BS | 3BS | 5D | 5D | 4BS | 2BS | 2BS | 2BS | 5D | 5D | 4BS | 4BS | 4BS | 5D | 5D |
|  | .500 | 2B | 3BS | 2B | — | 5D | 4BS | 3BS | 2BS | — | 3BS | 5D | 5D | 2BS | 3BS | 4BS | 5D | 4BS |
|  | .250 | 2B | 3SF | 2B | — | 3SF | 4SBF | 2SB | 2S | 1 | 4RSB | 4BS | 3RSF | 3SB | 4RBS | 4RBS | 4RBS | 4RFS |
|  | .125 | 1 | 1 | — | — | 2BS | 3FBS | — | — | — | 3SF | 3S | 3FS | 1 | 2S | 3BS | 3RFS | 2S |
|  |  |  |  |  |  | 2S | 2SF |  |  |  |  |  |  |  |  |  |  | — |
| 2 | 4.00 | 2S | 0 | 0 | 0 | 5D | 5D | 0 | 0 | 3S | 0 | 0 | 0 | 3BS | 3BS | 5D | 4RSB | — |
|  | 2.00 | 2B | 4BS | 3BS | 2B | 5D | 5D | 2BS | 3BS | 4SB | 5D | 5D | 5D | 3BS | 5D | 5D | 4BS | 5D |
|  | 1.00 | 2B | 3BS | 4BS | 2B | 5D | 5D | 2B | 1 | 3BS | 2SB | 5D | 4BS | 3BS | 4BS | 5D | 4BS | 5D |
|  | .500 | 2B | 3BS | — | — | 5D | 5D | 2B | 2BS | 2BS | 2BS | 5D | 2BS | 3BS | 4BS | 5D | 4RBS | 5D |
|  | .250 | — | 3SB | 2B | — | 5D | 5D | 2S | — | 3SBF | 4RBS | 5D | 5D | 3S | 4BS | 5D | 4RBS | 4SB |
|  | .125 | 1 | 2SB | 2B | — | 4SBF | 4SFB | — | — | 2BS | 3RBS | 5D | 2BS | 2B | 4RSB | 5D | 2BS | 2SB |
|  |  |  |  |  |  | 3BSF | 3SFB |  |  |  | 3RBS |  | 2SB |  | 2BS | 3BS | 3BS |  |
| 3 | 4.00 | 1 | 0 | 0 | 0 | 5D | 5D | 0 | 0 | 1 | 0 | 0 | 0 | 1 | 0 | 5D | 5D | 4RBS |
| 4 | 2.00 | 5D | 5D | 5D | 4BS | 5D | 5D | 5D | 4BS | 4RBS | 5D | 5D | 5D | 5D | 5D | 5D | 5D | 4RBS |
|  | 1.00 | 4BS | 3BS | 4BS | 4BS | 5D | 4BS | 5D | 2SB | 3SB | 5D | 5D | 5D | 5D | 5D | 5D | 5D | 3SB |
|  | .500 | 2BS | 3BS | 3BS | 3BS | 5D | 3BS | 5D | 2SB | 3BS | 5D | 5D | 5D | 3S | 5D | 5D | 5D | — |
| 5 | 4.00 | 0 | 0 | 0 | 0 | 5 | — | 0 | 0 | 0 | 0 | 0 | 0 | 0 | 0 | 0 | 0 | 0 |
|  | 2.00 | 0 | 0 | 0 | 0 | — | — | — | — | — | — | — | — | — | — | — | — | — |
|  | 1.00 | 0 | 0 | 0 | 0 | — | — | — | — | — | — | — | — | — | — | — | — | — |
|  | .500 | 0 | 0 | 0 | 0 | — | — | — | — | — | — | — | — | — | — | — | — | — |
| 6 | 4.00 | 0 | 0 | 0 | 0 | 5D | 5D | 5D | — | 2S | 4BS | 5D | 3BS | 2B | 5D | 5D | 5D | 4BS |
|  | 2.00 | 0 | 0 | 0 | 0 | 4BS | 4BS | 5D | — | 4RBS | 4BS | 5D | 2SB | — | 4BS | 3BS | 5D | 3BS |
|  | 1.00 | 0 | 0 | 0 | 0 | 3BS | 3BS | — | — | 3SB | — | — | — | — | 2B | 3BS | 2S | — |
|  | .500 | 0 | 0 | 0 | 0 | 5 | — | — | — | 3BS | — | — | — | 2B | — | — | — | — |
| 7 | 4.00 | 0 | — | 0 | 0 | 5D | 5D | 2B | — | 4SBF | 5D | 5D | 5D | 4SBF | 5D | 5D | 5D | 3RBS |
| 8 | 4.00 | 2BS | — | — | 0 | 4RBS | 4RSB | — | — | — | 4BS | — | 2B | — | 4B | 3BS | — | — |
|  | 2.00 | — | — | — | 0 | 5D | 4RSB | — | — | 2B | 4BS | — | 2B | 4BS | — | — | 4BS | — |
|  | 1.00 | — | — | — | 0 | 3SB | 3SB | — | — | — | — | — | 2B | 3BS | 3BS | 3BS | 2B | 3SB |
| 52 | 2.00 | 0 | 0 | 0 | 0 | 4BS | 4RSB | 0 | — | 0 | 5D | — | 2B | 4SB | 4RSB | 5D | 0 | 0 |
|  | 1.00 | 0 | 0 | 0 | 0 | 3SB | 4RSB | 2B | — | 0 | 5D | — | 2B | 3SB | 4B | 5D | 0 | 0 |
|  | .500 | 0 | 0 | 0 | 0 | 3SB | 3SB | — | — | 0 | 5D | — | 2B | — | 3BS | — | — | — |
| 53 | 2.00 | 0 | 0 | 0 | 0 | — | 1 | — | — | — | — | — | — | — | — | — | — | — |
|  | 1.00 | 0 | 0 | 0 | 0 | — | — | — | — | — | — | — | — | — | — | — | — | — |
|  | .500 | 0 | 0 | 0 | 0 | — | — | — | — | — | — | — | — | — | — | — | — | — |
| 27 | 4.00 | 0 | 0 | 0 | 0 | 5D | 4BS | 0 | 0 | 0 | 5D | 5D | 5D | 5N | 5N | 5D | 5D | 0 |
|  | 2.00 | 0 | 0 | 0 | 0 | 4BS | 5N | 2F | — | 0 | 5D | 5D | 4BS | 4SB | 4SB | 5N | 5D | 5D |
|  | 1.00 | 0 | 0 | 0 | 0 | 3BS | 5N | — | — | 0 | 5D | 5D | 4BS | 3RSB | 3BS | 5D | 5D | 5D |
|  | .500 | 0 | 0 | 0 | 0 | 4BS | 3RSB | — | — | 0 | — | — | — | 4RSB | 4BSF | 5D | 4BS | 4BS |
| 26 | 4.00 | 4BS | 4BSF | — | 2B | 5N | 4BS | 0 | — | 4SBF | 5D | 5D | 0 | 2BS | 2BS | 5D | 3BS | 3BS |
|  | 2.00 | 2B | 3BS | 2B | — | 5D | 5D | 2F | — | 2C | 5D | 5D | 5D | 5N | 5N | 5D | 5D | 0 |
|  | 1.00 | 0 | — | — | 0 | 5D | 5D | — | — | — | — | — | — | — | — | 5N | — | — |
|  | .500 | — | — | — | — | — | — | — | — | — | — | — | — | — | — | — | — | — |
| 46 | 4.00 | 0 | 0 | 0 | 0 | 5D | 5D | — | 0 | 0 | 0 | 0 | 0 | 2C | 2C | 5D | 3BS | — |
| 47 | 2.00 | 0 | 0 | 0 | 0 | — | — | — | 0 | 0 | 0 | 0 | — | 1 | 1 | — | — | — |
|  | 1.00 | 0 | 0 | 0 | 0 | — | — | — | — | — | — | — | — | — | — | — | — | — |
|  | .500 | 0 | 0 | 0 | 0 | — | — | — | — | — | — | — | — | — | 0 | — | 0 | — |
| 49 | 2.00 | 0 | 0 | 0 | 0 | 5D | 5D | 3CS | 0 | 0 | 0 | 0 | 4BS | 4BS | 0 | 5D | 0 | 5D |

-continued

PREEMERGENCE

| Cmpd No. | Rate (lb./A) | Brly | Corn | Rice | Wheat | FlMi | LaCg | WiOa | Cttn | Sybn | Sght | Lmqr | Jiwe | Mngy | Mstd | RrPw | Tmto | Vele |
|---|---|---|---|---|---|---|---|---|---|---|---|---|---|---|---|---|---|
| 48 | 1.00 | 0 | 0 | 0 | 0 | 5D | 5 | 2C | 0 | 0 | 0 | 0 | 5D | 3SC | 0 | 5D | 0 | 4BS |
|  | .500 | 0 | 0 | 0 | 0 | 4CS | 4BS | 2C | 0 | 0 | 0 | 0 | 5D | 2CS | — | 5D | 0 | 3SC |
|  | 2.00 | 0 | 0 | 0 | 0 | 5D | 4RS | — | 0 | 0 | 0 | 0 | 5N | — | — | 5N | 0 | 5N |
|  | 1.00 | 0 | 0 | 0 | 0 | 4RS | 3S | — | 0 | 0 | 0 | 0 | 5D | — | — | 5N | 0 | 5N |
| 51 | .500 | 0 | 0 | 0 | 0 | 2RS | 5N | 4BS | 0 | 0 | 0 | 0 | — | — | — | 4RS | 0 | 3RS |
|  | 2.00 | 0 | 0 | 0 | 0 | 5D | 5N | 4BS | 0 | 0 | 0 | 0 | 5D | 5D | 5D | 5D | 0 | 5D |
|  | 1.00 | 0 | 0 | 0 | 0 | 5D | 5D | 4BS | 0 | 0 | 0 | 0 | 5D | 5D | 5D | 5D | 0 | 5D |
|  | .500 | 0 | 0 | 0 | 0 | 5D | 5D | 0 | 0 | 0 | 0 | 0 | 4BS | 4BS | 5D | 5D | 0 | 5D |
| 16 | 4.00 | 1 | 0 | 1 | 0 | 2B | 3BS | 2B | 1 | 2B | 0 | 0 | 0 | 2SF | 3RS | 4BS | 3RS | 2BS |
|  | 2.00 | 1 | 1 | — | 0 | 2BS | — | 2B | 1 | 2S | 5D | 0 | 5D | 2B | 2S | 4BS | 3RBS | 2B |
|  | 1.00 | 1 | — | — | 0 | — | — | — | 1 | 2S | 4RBS | 0 | 5D | — | 1 | 2RS | 2SB | 1 |
|  | .500 | 1 | — | — | 0 | — | — | — | 1 | — | 2S | 0 | 2BS | 2B | 1 | — | 1 | — |
| 17 | 4.00 | 2B | 0 | 0 | 0 | 5D | 5D | 0 | 0 | 2C | 5D | 5D | 0 | 3SR | 4RS | 5D | 5D | 5D |
|  | 2.00 | 1 | 2B | 2B | 0 | 5D | 5D | 2BS | 2BS | 1 | 5D | 5D | 5D | 4RBS | 3RS | 5D | 5D | 5D |
|  | 1.00 | 1 | — | — | 0 | 5D | 5D | — | — | 1 | 5D | 5D | 5D | 2B | — | 5D | 4RBS | 5D |
|  | .500 | 1 | — | — | 0 | 3BS | 4RBS | 3BS | 1 | — | 4BS | 5D | 4BS | — | 4RBS | 5D | 3BS | 3BS |
|  | .250 | 1 | — | — | 0 | — | 1 | — | 1 | — | — | — | — | — | 3BS | — | 3S | — |
|  | .125 | — | — | — | 0 | 2B | 1 | — | 1 | — | 2B | 0 | 4BS | 2BS | 4BS | 5D | 1 | 1 |
| 18 | 4.00 | 2S | 0 | 0 | 0 | 5N | 5D | 0 | 0 | 3SF | 5D | 5N | 0 | 4RS | 4BS | 5D | 4RS | 0 |
|  | 2.00 | 1 | 0 | 0 | 0 | 5N | 5D | 3BS | 0 | — | 4BS | 5N | 5D | 2B | 2S | 5D | 4BS | 0 |
|  | 1.00 | 1 | 0 | 1 | 2BS | 5N | 5D | 2B | 0 | 2S | 4BS | 5D | 5D | — | 4RBS | 5D | 4BS | 0 |
|  | .500 | 3BS | 3BS | 1 | 1 | 5D | 5D | 4BS | 1 | 2B | 3S | 5D | 5D | 3SB | 3BS | 5D | 4BS | 3BS |
|  | .250 | 1 | — | — | 0 | 3BS | 4BS | — | 0 | — | 3BS | 5D | 5D | — | 2S | 5D | 3BS | — |
|  | .125 | 1 | — | — | 0 | 2BS | 2BS | — | 0 | — | 2B | 5D | 4BS | — | — | 3BS | 1 | — |
| 19 | 4.00 | 3BS | 0 | 0 | 0 | 5N | 2BS | 0 | 0 | 2S | 0 | 0 | 0 | 4RS | 3BS | 3BS | 2BS | 0 |
| 21 | 4.00 | 2B | 3BS | 0 | 0 | 5N | — | 3BS | 0 | 2B | 0 | 0 | 5D | 2B | — | — | — | 0 |
| 22 | 4.00 | 2B | 2BS | 3BS | 2B | 5N | 5N | 2B | — | 2B | 0 | 0 | 5D | — | — | 5D | 5D | 4RBS |
|  | 2.00 | 1 | 2B | 3BS | 1 | 5N | 5D | — | 1 | — | 5D | 4RBS | 5D | 5D | 5D | 4RBS | 5N | 3RBS |
|  | 1.00 | 1 | 2B | — | 1 | 4RBS | 4RBS | 4RBS | 1 | — | 4RBS | 4RS | 2SB | 3BS | 5D | 4RBS | 5N | 2BS |
|  | .500 | 1 | — | — | 0 | 0 | 3BS | 3BS | 1 | — | 3RS | 2S | 5D | 2BS | 2S | 3BS | 5D | 0 |
| 15 | 4.00 | 1 | 0 | 0 | 0 | 5D | 4BS | 0 | 0 | 0 | 2S | 5D | 0 | 4RBS | 5D | 4BS | 3BS | 0 |
|  | 2.00 | 1 | — | — | 1 | 5D | 3BS | — | 0 | 0 | 3BS | 4BS | 5D | 4RBS | 5D | 4BS | 3RS | — |
|  | 1.00 | 1 | — | — | 1 | 2BS | — | — | 1 | 0 | 2S | — | 4BS | — | 2BS | 0 | — | — |
|  | .500 | 2BS | — | — | 1 | — | 2BS | — | 1 | — | — | — | — | — | 2BS | 2BS | 1 | — |
| 13 | 4.00 | 1 | 4BFS | 1 | 0 | 5N | 5N | 0 | 0 | 3RBS | 4RBS | 0 | 0 | 5D | 4RS | 3BS | 5D | 4RS |
|  | 2.00 | 1 | 3BFS | — | 1 | 5N | 5D | 4RBS | 1 | — | 3RS | 4RBS | 4RBS | 5N | 4SB | 4RBS | 4RBS | 3S |
|  | 1.00 | — | 2B | — | — | 5N | 4RBS | 3BS | — | — | 2S | 4RS | 5D | 5N | 2S | 4RBS | 5D | 2S |
|  | .500 | — | 2B | — | 0 | 4RBS | 3BS | — | — | — | 2S | 2S | 2SB | 4RBS | — | 3BS | 5D | — |
| 9 | 4.00 | — | 0 | 0 | 0 | 0 | 4BS | 0 | 0 | — | 0 | 5D | 5D | — | — | 2BS | 5D | — |
|  | 2.00 | 1 | — | — | 1 | 3BS | 3BS | 3BS | 1 | — | 3BS | 5D | 0 | 4RS | 2C | 2BS | 4RBS | — |
|  | 1.00 | 2BS | — | — | — | 3BS | — | — | — | — | — | 4BS | 5D | — | 5D | 0 | 2C | 1 |
|  | .500 | 1 | — | — | 0 | 2B | 1 | — | — | — | 3BS | 0 | 4BS | — | 2BS | 0 | 3BS | 1 |
| 11 | 4.00 | — | 0 | 0 | 0 | 4RBS | 4BS | 0 | 0 | — | 0 | 0 | 0 | — | 3RS | 2S | 4RS | 2S |
|  | 2.00 | 1 | 1 | 1 | 0 | 4RBS | 1 | 0 | 1 | — | 5D | 5D | 4BS | — | 3SB | — | 4RS | — |
|  | 1.00 | 1 | — | — | — | — | — | — | — | — | — | — | — | — | — | — | — | — |

-continued

PREEMERGENCE

| Cmpd No. | Rate (lb./A) | Brly | Corn | Rice | Wheat | FlMi | LaCg | WiOa | Cttn | Sybn | Sgbt | Lmqr | Jiwc | Mngy | Mstd | RrPw | Tmto | Vele |
|---|---|---|---|---|---|---|---|---|---|---|---|---|---|---|---|---|---|
| 14 | .500 | — | — | — | — | — | — | — | — | — | — | — | — | — | — | — | — | — |
|  | 4.000 | — | — | — | — | — | — | — | — | — | — | — | — | — | — | — | — | 0 |
|  | 2.000 | 0 | 0 | 0 | 0 | — | — | 0 | 0 | — | — | — | 0 | 0 | 0 | 0 | — | — |
|  | 1.000 | — | — | — | — | — | — | — | — | — | — | — | — | — | — | — | — | — |
|  | 0.500 | 0 | 0 | 0 | 0 | — | — | 0 | 0 | — | — | — | 0 | 0 | 0 | 0 | — | — |
| 28 | 8.000 | 0 | 0 | 0 | 0 | 0 | 5N | 0 | 0 | 0 | 0 | 0 | 0 | 5D | 0 | 5N | 5N | 0 |
|  | 2.000 | 0 | 0 | 0 | 0 | 0 | 5N | 4BS | 0 | 0 | 0 | 0 | 0 | 4SB | 0 | 4BS | 0 | 3BS |
|  | 1.000 | — | — | — | — | — | 4BS | 2B | — | — | — | — | — | 4SB | 2SB | — | 0 | 2BS |
|  | 0.500 | 0 | 0 | 0 | 0 | 0 | 3SB | 0 | 0 | 0 | 0 | 0 | 0 | 3RS | 2BS | 2B | 5N | — |
| 33 | 8.000 | 0 | 0 | 0 | 0 | 5D | 5N | 0 | 0 | 0 | 0 | 0 | 0 | 4BS | 2RS | 5N | 5D | 0 |
|  | 4.000 | — | — | — | — | 5D | 5D | 0 | — | — | — | — | — | 3RS | 3SFB | 5D | 5N | 0 |
| 34 | 4.000 | 4BS | — | — | — | 4BSF | 4RBS | 0 | 0 | 0 | 4RS | 4RS | 0 | 2S | — | A | — | 4RS |
|  | 2.000 | 1 | — | — | — | 4SB | 3S | 2S | 0 | 0 | 4RS | 4RS | 0 | 2S | — | 4RS | — | 4RS |
|  | 1.000 | 1 | — | — | — | 4SC | 2S | 0 | 0 | 0 | 3RS | 4RS | 0 | — | — | 4RS | — | 3RS |
|  | 0.500 | — | — | — | 2S | 3S | — | 0 | — | — | — | — | — | — | — | — | — | — |
| 56 | 8.000 | 0 | 0 | 0 | 0 | 0 | 5D | 0 | 0 | 0 | 0 | 0 | 0 | 0 | 0 | 5D | 0 | 0 |
| 54 | 4.000 | — | — | — | — | 5D | 5D | — | — | — | — | — | — | — | — | A | 5D | 4BS |
|  | 2.000 | — | — | — | — | 4BSF | 4RBS | 0 | — | — | — | — | — | 3SB | 4BS | 3SB | 5N | 3SB |
|  | 1.000 | — | — | — | — | 3SB | 3S | 0 | — | — | — | — | — | — | — | — | — | — |
| 55 | 8.000 | 0 | 0 | 0 | 0 | 3SB | 5N | 0 | 0 | 0 | 0 | 0 | 0 | 3S | 0 | 5N | 0 | 0 |
|  | 2.000 | 0 | 0 | 0 | 0 | 3SB | 4BS | 3BS | 0 | 0 | 0 | 0 | 0 | 2S | 0 | 5D | 0 | 5D |
|  | 1.000 | — | — | — | — | 2B | 2S | — | — | — | — | — | — | — | — | — | — | — |
|  | 0.500 | 0 | 0 | 0 | 0 | 0 | — | 0 | 0 | 0 | 0 | 0 | 0 | — | — | — | — | — |
| 58 | 8.000 | 0 | 0 | 0 | 0 | 4SB | 4RSB | 4BS | 0 | 0 | 0 | 0 | 0 | 4SB | — | 4RSB | 0 | 5D |
|  | 2.000 | 0 | 0 | 0 | 0 | 4SB | 4SFB | 2SB | 0 | 0 | 0 | 0 | 0 | 2S | 5D | — | 0 | 5D |
|  | 1.000 | — | — | — | — | — | — | 2SB | — | — | — | — | — | 2S | 5D | — | 0 | 5D |
|  | 0.500 | — | — | — | — | — | — | 0 | — | — | — | — | — | — | — | — | — | — |
| 59 | 8.000 | 0 | 0 | 0 | 0 | 5D | 5N | 4BS | 0 | 0 | 0 | 0 | 0 | 4SB | 0 | 5N | 0 | 5D |
|  | 2.000 | 0 | 0 | 0 | 0 | 5D | 5D | 2SB | 0 | 0 | 0 | 0 | 0 | 2S | 5D | 5D | 0 | 5D |
|  | 1.000 | 0 | 0 | 0 | 0 | 5D | 5D | 2SB | 0 | 0 | 0 | 0 | 0 | 2S | 5D | 5D | 0 | 5D |
|  | 0.500 | 0 | 0 | 0 | 0 | 5D | 4SB | 0 | 0 | 0 | 0 | 0 | 0 | 4SB | 0 | 5D | 0 | 5D |
| 62 | 8.000 | 0 | 0 | 0 | 0 | 5D | 5D | 3BS | 0 | 0 | 0 | 0 | 0 | 4S | 0 | 5D | 5D | 5D |
|  | 2.000 | 0 | 0 | 0 | 0 | 5D | 5D | 2B | 0 | 0 | 0 | 0 | 0 | 3S | 0 | 3BS | 0 | 3BS |
|  | 1.000 | — | — | — | — | — | — | 1 | — | — | — | — | — | — | — | — | — | — |
|  | 0.500 | 0 | 0 | 0 | 0 | 0 | 5N | 0 | 0 | 0 | 0 | 0 | 0 | 0 | 0 | 2S | 5N | 0 |
| 10 | 8.000 | 0 | 0 | 0 | 0 | 4RBD | 4SB | 5D | 0 | 0 | 0 | 0 | 0 | 5N | 5N | 5N | 5N | 5N |
|  | 2.000 | 0 | 0 | 0 | 0 | 5D | 4SB | 5D | 0 | 0 | 0 | 0 | 0 | 5N | 5N | 5N | 5N | 5D |
|  | 1.000 | 0 | 0 | 0 | 0 | 5D | 2S | 5D | 0 | 0 | 0 | 0 | 0 | 5N | 5N | 5D | 5D | 5D |
|  | 0.500 | 0 | 0 | 0 | 0 | 2B | 5N | 2S | 0 | 0 | 0 | 0 | 0 | 2S | 1 | 4SB | 5N | 5D |
| 66 | 8.000 | 0 | 0 | 0 | 0 | 5D | 5D | 1 | 0 | 0 | 0 | 0 | 0 | 2RS | 1 | 5D | 0 | 5D |
|  | 2.000 | 0 | 0 | 0 | 0 | 5D | 5D | 3RSB | 0 | 0 | 0 | 0 | 0 | 3RSC | 2R | 5D | 0 | 4RSB |
|  | 1.000 | 0 | 0 | 0 | 0 | 5D | 5D | 2SB | 0 | 0 | 0 | 0 | 0 | 2S | 2RS | 5D | 0 | 5D |
|  | 0.500 | 0 | 0 | 0 | 0 | 5D | 5D | 2RSB | 0 | 0 | 0 | 0 | 0 | 2RS | 5D | 5D | 0 | 5D |
| 67 | 8.000 | 0 | 0 | 0 | 0 | 0 | 5N | 0 | 0 | 0 | 0 | 0 | 0 | — | 5D | 3BS | 5N | 5D |
|  | 2.000 | 0 | 0 | 0 | 0 | 5N | 5N | 4R | 0 | 0 | 0 | 0 | 0 | 4R | 5N | 5N | 5N | 5N |
|  | 1.000 | 0 | 0 | 0 | 0 | 5N | 5N | 4RSB | 0 | 0 | 0 | 0 | 0 | 5N | 5N | 5N | 5N | 5N |
|  | 0.500 | 0 | 0 | 0 | 0 | 5N | 5N | 3RSF | 0 | 0 | 0 | 0 | 0 | 5RN | 5N | 5N | 0 | 5N |
| 58 | 2.00 | 0 | 0 | 0 | 0 | 5D | 5RS | 3B | 0 | 0 | 0 | 0 | 5D | 3SB | 5D | 5N | 0 | 5N |
|  | 1.00 | 0 | 0 | 0 | 0 | 4RB | 4BR | 2SB | 0 | 0 | 0 | 0 | 4RB | — | 5D | 5D | 0 | 5D |

-continued

PREEMERGENCE

| Cmpd No. | Rate (lb./A) | Brly | Corn | Rice | Wheat | FtMi | LaCg | WtOa | Cttn | Sybn | Sght | Lmqr | Jiwc | Mngy | Mstd | RrPw | Tmto | Vele |
|---|---|---|---|---|---|---|---|---|---|---|---|---|---|---|---|---|---|---|
| 82 | .500 | 0 | 0 | 0 | 0 | 3SB | 3S | 1 | 0 | 0 | 0 | 0 | 1 | 2S | 3RS | 4R | 0 | 5R |
|  | 2.00 | 0 | 0 | 0 | 0 | 5D | 5D | 3RB | 0 | 0 | 0 | 0 | 5D | 5D | 5D | 5D | 0 | 5D |
|  | 1.00 | 0 | 0 | 0 | 0 | 5D | 5D- | 2B | 0 | 0 | 0 | 0 | 5D | 2S | 5D | 4SB | 0 | 5D |
|  | .500 | 0 | 0 | 0 | 0 | 4SB | 5D | 1 | 0 | 0 | 0 | 0 | 5D | 2S | 5D | 4RS | 0 | 5D |
| 76 | 2.00 | 0 | 0 | 0 | 0 | 5D | 5D | 4SB | 0 | 0 | 0 | 0 | 5D | 5D | 5D | 5D | 0 | 5D |
|  | 1.00 | 0 | 0 | 0 | 0 | 5D | 5D | 4SB | 0 | 0 | 0 | 0 | 5D | 5D | 5D | 5D | 0 | 5D |
|  | .500 | 0 | 0 | 0 | 0 | 5D | 5D | 3SCB | 0 | 0 | 0 | 0 | 5D | 3RS | 5D | 5D | 0 | 5D |

| | | POSTEMERGENCE | | | | | | | | |
|---|---|---|---|---|---|---|---|---|---|---|
| Cmpd No. | Rate (lb./A) | Brly | Corn | Rice | Wheat | FtMi | LaCg | WiOa | Cttn | Sybn |
| 1 | 4.00 | 2B | 0 | 0 | 0 | 3BS | 3BS | 0 | 0 | 3BS |
| | 2.00 | 2BS | 4BS | 2B | 2B | 4BS | 4BS | 2BS | 3BS | 3BS |
| | 1.00 | 2B | 4BS | 1 | 2B | 3BS | 4BS | 2BS | 2BS | 3BCS |
| | .500 | 2B | 4BS | 2B | 2B | 3BS | 4BS | 2BS | 2BS | 3CBS |
| 2 | 4.00 | 1 | 0 | 0 | 0 | 4BS | 2B | 0 | 0 | 2CB |
| | 2.00 | 2B | 4BS | 2BS | 2B | 4BS | 4BS | 1 | 4BS | 3BS |
| | 1.00 | 2B | 4BS | 2BS | 2B | 3BS | 3BS | 1 | 4BS | 3BS |
| | .500 | 2B | 4BS | 1 | 2B | 3BS | 3BS | 1 | 3BS | 3BS |
| 3 | 4.00 | 1 | 0 | 0 | 0 | 1 | 1 | 0 | 0 | 1 |
| 4 | 2.00 | 3BS | 5D | 3BS | 4BS | 5D | 5D | 5D | 5D | 5D |
| | 1.00 | 3BS | 4BS | 3BS | 3BS | 5D | 5D | 5D | 5D | 4BS |
| | .500 | 3BS | 4BS | 3SB | 3BS | 5D | 5D | 5D | 5D | 4BS |
| 5 | 4.00 | 1 | 0 | 0 | 0 | 3BS | 2SB | 0 | 0 | 2BS |
| | 2.00 | 0 | 0 | 0 | 0 | 0 | 0 | 0 | 0 | 0 |
| | 1.00 | 2B | 2B | 2B | 1 | 2B | 1 | 1 | 2BS | 3B |
| | .500 | 2B | 1 | 1 | 1 | 2B | 2B | 1 | 1 | 3B |
| 6 | 4.00 | 1 | 0 | 0 | 0 | 2B | 2B | 0 | 0 | 2BS |
| | 2.00 | 2B | 2BS | 2B | 1 | 2B | 2B | 1 | 3BS | 3CBS |
| | 1.00 | 1 | 1 | 2B | 1 | 2B | 1 | 1 | 3BS | 3CB |
| | .500 | 1 | 1 | 1 | 1 | 2B | 1 | 1 | 2B | 2CB |
| 7 | 4.00 | 2B | 0 | 0 | 0 | 5D | 5D | 0 | 0 | 3BS |
| 8 | 4.00 | 1 | 0 | 0 | 0 | 1 | 4BS | 0 | 0 | 2B |
| | 2.00 | 1 | 2B | 1 | 2B | 3BS | 5D | 2B | 2B | 2BS |
| | 1.00 | 1 | 2B | 1 | 2B | 4BS | 3BS | 1 | 2B | 2B |
| | .500 | 1 | 2B | 1 | 1 | 2B | 2B | 1 | 1 | 2B |
| 52 | 2.00 | 0 | 0 | 0 | 0 | 3BS | 3BS | 2B | 0 | 0 |
| | 1.00 | 0 | 0 | 0 | 0 | 3BS | 2B | 2B | 0 | 0 |
| | .500 | 0 | 0 | 0 | 0 | 4BS | 2SB | 2B | 0 | 0 |
| 27 | 4.00 | 1 | 0 | 0 | 0 | 2B | 2BS | 0 | 0 | 2BCF |
| | 2.00 | 0 | 0 | 0 | 0 | 3BS | 2B | 2B | 0 | 0 |
| | 1.00 | 0 | 0 | 0 | 0 | 3SB | 2B | 2S | 0 | 0 |
| | .500 | 0 | 0 | 0 | 0 | 2SB | 2B | 1 | 0 | 0 |
| 26 | 4.00 | 2B | 0 | 0 | 0 | 4BS | 5D | 0 | 0 | 4BS |
| | 2.00 | 2BS | 3BFS | 2BS | 2BS | 4BS | 4BS | 2BS | 4BS | 4BFS |
| | 1.00 | 2B | 4BFS | 1 | 2B | 3BS | 4BS | 2B | 4BS | 3BS |
| | .500 | 2B | 3BFS | 1 | 2B | 2BS | 3BS | 2B | 4BS | 3BS |
| 46 | 4.00 | 1 | 0 | 0 | 0 | 1 | 1 | 0 | 0 | 1 |
| 47 | 2.00 | 0 | 0 | 0 | 0 | 1 | 1 | 1 | 0 | 0 |
| | 1.00 | 0 | 0 | 0 | 0 | 1 | 1 | 1 | 0 | 0 |
| | .500 | 0 | 0 | 0 | 0 | 1 | 1 | 1 | 0 | 0 |
| 49 | 2.00 | 0 | 0 | 0 | 0 | 1 | 1 | 1 | 0 | 0 |
| | 1.00 | 0 | 0 | 0 | 0 | 1 | 1 | 1 | 0 | 0 |
| | .500 | 0 | 0 | 0 | 0 | 1 | 1 | 1 | 0 | 0 |
| 48 | 2.00 | 0 | 0 | 0 | 0 | 4BS | 3BS | 2B | 0 | 0 |
| | 1.00 | 0 | 0 | 0 | 0 | 4BS | 3BS | 2B | 0 | 0 |
| | .500 | 0 | 0 | 0 | 0 | 4BS | 3BS | 2B | 0 | 0 |
| 51 | 2.00 | 0 | 0 | 0 | 0 | 4BS | 5D | 3BS | 0 | 0 |
| | 1.00 | 0 | 0 | 0 | 0 | 4BS | 3BS | 2BS | 0 | 0 |
| | .500 | 0 | 0 | 0 | 0 | 3BS | 3BS | 2B | 0 | 0 |
| 16 | 4.00 | 1 | 0 | 0 | 0 | 2B | 3BS | 0 | 0 | 2B |
| | 2.00 | 2B | 3FSB | 2B | 1 | 2BS | 3BS | 2BS | 2B | 2SF |
| | 1.00 | 2B | 3FSB | 2B | 1 | 2B | 2BS | 2B | 2B | 2SF |
| | .500 | 1 | 3BFS | 1 | 1 | 2B | 2BS | 2B | 1 | 2SBF |
| 17 | 4.00 | 2B | 0 | 0 | 0 | 4BS | 4BS | 0 | 0 | 3BS |
| | 2.00 | 2BS | 4BS | 2B | 2BS | 3BS | 2BS | 2B | 3BS | 3CBS |
| | 1.00 | 2B | 3BS | 2B | 2B | 3BS | 3BS | 2B | 3BS | 3BCS |
| | .500 | 1 | 2BS | 2B | 1 | 2B | 2BS | 1 | 2BS | 2BC |
| 18 | 4.00 | 2B | 0 | 0 | 0 | 3BS | 4BS | 0 | 0 | 3BSF |
| | 2.00 | 2B | 4BS | 3BS | 2B | 4BS | 3BS | 2BS | 3BS | 3CBS |
| | 1.00 | 2B | 3BS | 3BS | 2B | 2BS | 2BS | 2B | 3BS | 2CB |
| | .500 | 2B | 3BS | 1 | 2B | 2BS | 2BS | 2B | 3BS | 2CB |
| 19 | 4.00 | 1 | 0 | 0 | 0 | 2SB | 3BS | 0 | 0 | 2B |
| 21 | 4.00 | 1 | 0 | 0 | 0 | 2B | 1 | 0 | 0 | 1 |
| 22 | 4.00 | 4BS | 0 | 0 | 0 | 5D | 5D | 0 | 0 | 4BS |
| | 2.00 | 4BS | 4BS | 3BS | 2BS | 5D | 5D | 3BS | 3BS | 4BS |
| | 1.00 | 3BS | 4BS | 3BS | 2BS | 5D | 5D | 3B | 3BS | 3BS |
| | .500 | 3BS | 4BS | 2B | 2B | 5D | 5D | 3BS | 3BS | 4BS |
| 15 | 4.00 | 1 | 0 | 0 | 0 | 4BS | 3BS | 0 | 0 | 2BS |
| | 2.00 | 2B | 4BS | 2B | 1 | 3BS | 2BS | 2B | 2BS | 3BS |
| | 1.00 | 1 | 4BS | 2B | 1 | 3BS | 2BS | 2B | 1 | 3BS |
| | .500 | 1 | 3BS | 1 | 1 | 2BS | 2BS | 1 | 1 | 2B |
| | .500 | 1 | 3BFS | 2B | 1 | 3BS | 2SB | 1 | 1 | 2BF |
| | .250 | 2B | 3FBS | 2B | 1 | 2SB | 3SB | 2BS | 2B | 2BF |
| | .125 | 1 | 3FBS | 2B | 1 | 2BS | 3SB | 1 | 1 | 2B |
| 13 | 4.00 | 1 | 0 | 0 | 0 | 4BS | 3BS | 0 | 0 | 2BS |
| | 2.00 | 2B | 3BSF | 3BS | 2B | 3BS | 4BS | 2BS | 2B | 4BS |
| | 1.00 | 2B | 3BSF | 2BS | 2B | 2BS | 3BS | 2B | 2B | 3BS |
| | .500 | 2B | 3BSF | 2BS | 2B | 2BS | 2BS | 2B | 1 | 3BS |

-continued

POSTEMERGENCE

| Cmpd No. | Rate | | | | | | | | | |
|---|---|---|---|---|---|---|---|---|---|---|
| | .500 | 2B | 2BS | 3BS | 2B | 5D | 4BS | 2BS | 3B | 3BS |
| | .250 | 2B | 2BS | 3BS | 2B | 2BS | 4BS | 2BS | 2B | 3SB |
| | .125 | 2B | 2BS | 2B | 2B | 3BS | 2BS | 2B | 2B | 3BS |
| 9 | 4.00 | 1 | 0 | 0 | 0 | 1 | 2BS | 0 | 0 | 2B |
| | 2.00 | 2B | 2B | 1 | 2B | 2B | 2BS | 1 | 2B | 2B |
| | 1.00 | 2B | 2B | 2B | 1 | 3BS | 3BS | 2B | 1 | 2B |
| | .500 | 2B | 1 | 1 | 1 | 2B | 3BS | 1 | 1 | 2B |
| 11 | 4.00 | 2BS | 0 | 0 | 0 | 2B | 2B | 0 | 0 | 2BS |
| | 2.00 | 2BS | 2B | 2B | 2BS | 2BS | 2S | 2B | 2B | 2BS |
| | 1.00 | 2B | 2B | 2B | 2B | 2BS | 2SB | 1 | 1 | 2CB |
| | .500 | 2B | 2B | 2B | 2BS | 2S | 2SB | 1 | 1 | 2C |
| 12 | 4.00 | 1 | 0 | 0 | 0 | 1 | 1 | 0 | 0 | 1 |
| 14 | 4.00 | 1 | 0 | 0 | 0 | 2BS | 2BS | 0 | 0 | 2CB |
| | 2.00 | 1 | 2BS | 1 | 1 | 2B | 1 | 1 | 1 | 2B |
| | 1.00 | 1 | 2B | 1 | 1 | 1 | 1 | 1 | 1 | 2B |
| | .500 | 1 | 1 | 1 | 1 | 1 | 1 | 1 | 1 | 2B |
| 28 | 8.000 | 0 | 0 | 0 | 0 | 0 | 5D | 0 | 0 | 0 |
| | 2.000 | 0 | 0 | 0 | 0 | 4BS | 3BS | 3SB | 0 | 0 |
| | 1.000 | 0 | 0 | 0 | 0 | 4BS | 4BS | 1 | 0 | 0 |
| | 0.500 | 0 | 0 | 0 | 0 | 3BS | 2B | 1 | 0 | 0 |
| 33 | 8.000 | 0 | 0 | 0 | 0 | 0 | 5D | 0 | 0 | 0 |
| | 4.000 | 3BS | 0 | 0 | 0 | 5D | 4BS | 0 | 0 | 4BS |
| 34 | 4.000 | 3BS | 0 | 0 | 0 | 5D | 5D | 0 | 0 | 4BS |
| | 2.000 | 3BS | 4BSF | 3BS | 3BS | 5D | 5D | 4BS | 5D | 4BS |
| | 1.000 | 3BS | 4SBF | 3BS | 3BS | 5D | 5D | 3BS | 5D | 4BS |
| | 0.500 | 3BS | 4SFB | 3BS | 3BS | 5D | 5D | 2BS | 5D | 4BS |
| 56 | 8.000 | 0 | 0 | 0 | 0 | 0 | 2B | 0 | 0 | 0 |
| | 2.000 | 0 | 0 | 0 | 0 | 0 | 2B | 2B | 0 | 0 |
| | 1.000 | 0 | 0 | 0 | 0 | 0 | 1 | 1 | 0 | 0 |
| | 0.500 | 0 | 0 | 0 | 0 | 0 | 1 | 1 | 0 | 0 |
| 54 | 8.000 | 0 | 0 | 0 | 0 | 0 | 5D | 0 | 0 | 0 |
| | 2.000 | 0 | 0 | 0 | 0 | 3BS | 3BS | 1 | 0 | 0 |
| | 1.000 | 0 | 0 | 0 | 0 | 3BS | 2BS | 1 | 0 | 0 |
| | 0.500 | 0 | 0 | 0 | 0 | 3BS | 2B | 1 | 0 | 0 |
| 55 | 8.000 | 0 | 0 | 0 | 0 | 0 | 5D | 0 | 0 | 0 |
| | 2.000 | 0 | 0 | 0 | 0 | 4BS | 3BS | 3SB | 0 | 0 |
| | 1.000 | 0 | 0 | 0 | 0 | 4BS | 3SB | 3SB | 0 | 0 |
| | 0.500 | 0 | 0 | 0 | 0 | 3BS | 3SB | 2B | 0 | 0 |
| 58 | 8.000 | 0 | 0 | 0 | 0 | 0 | 5D | 0 | 0 | 0 |
| | 2.000 | 0 | 0 | 0 | 0 | 4BS | 4BS | 3BS | 0 | 0 |
| | 1.000 | 0 | 0 | 0 | 0 | 3BS | 4BS | 2B | 0 | 0 |
| | 0.500 | 0 | 0 | 0 | 0 | 3BS | 4BS | 2B | 0 | 0 |
| 59 | 8.000 | 0 | 0 | 0 | 0 | 0 | 5D | 0 | 0 | 0 |
| | 2.000 | 0 | 0 | 0 | 0 | 4BS | 5D | 3BS | 0 | 0 |
| | 1.000 | 0 | 0 | 0 | 0 | 4BS | 4BS | 3BS | 0 | 0 |
| | 0.500 | 0 | 0 | 0 | 0 | 4BS | 5D | 3BS | 0 | 0 |
| 62 | 8.000 | 0 | 0 | 0 | 0 | 0 | 5 | 0 | 0 | 0 |
| | 2.000 | 0 | 0 | 0 | 0 | 5D | 5D | 5D | 0 | 0 |
| | 1.000 | 0 | 0 | 0 | 0 | 5D | 5D | 5D | 0 | 0 |
| | 0.500 | 0 | 0 | 0 | 0 | 5D | 5D | 5D | 0 | 0 |
| 10 | 8.000 | 0 | 0 | 0 | 0 | 0 | 3SB | 0 | 0 | 0 |
| | 2.000 | 0 | 0 | 0 | 0 | 2B | 2B | 1 | 0 | 0 |
| | 1.000 | 0 | 0 | 0 | 0 | 2B | 2B | 1 | 0 | 0 |
| | 0.500 | 0 | 0 | 0 | 0 | 2B | 2B | 1 | 0 | 0 |
| 66 | 8.000 | 0 | 0 | 0 | 0 | 0 | 5D | 0 | 0 | 0 |
| | 2.000 | 0 | 0 | 0 | 0 | 5D | 5D | 3SB | 0 | 0 |
| | 1.000 | 0 | 0 | 0 | 0 | 5D | 5D | 2SB | 0 | 0 |
| | 0.500 | 0 | 0 | 0 | 0 | 5D | 4SB | 3SB | 0 | 0 |
| 67 | 8.000 | 0 | 0 | 0 | 0 | 0 | 5D | 0 | 0 | 0 |
| | 2.000 | 0 | 0 | 0 | 0 | 5D | 5D | 5D | 0 | 0 |
| | 1.000 | 0 | 0 | 0 | 0 | 5D | 5D | 4SB | 0 | 0 |
| | 0.500 | 0 | 0 | 0 | 0 | 5D | 5D | 4SB | 0 | 0 |
| 58 | 2.00 | 0 | 0 | 0 | 0 | 5D | 5D | 2B | 0 | 0 |
| | 1.00 | 0 | 0 | 0 | 0 | 5D | 5D | 3BS | 0 | 0 |
| | .500 | 0 | 0 | 0 | 0 | 5D | 5DB | 2BS | 0 | 0 |
| 76 | 2.00 | 0 | 0 | 0 | 0 | 5D | 5D | 4SB | 0 | 0 |
| | 1.00 | 0 | 0 | 0 | 0 | 5D | 5D | 4SB | 0 | 0 |
| | .500 | 0 | 0 | 0 | 0 | 5D | 4B | 3SB | 0 | 0 |
| 82 | 2.00 | 0 | 0 | 0 | 0 | 5D | 2SB | 2SB | 0 | 0 |
| | 1.00 | 0 | 0 | 0 | 0 | 4SB | 2SB | 2B | 0 | 0 |
| | .500 | 0 | 0 | 0 | 0 | 3SB | 2SB | 1 | 0 | 0 |
| 53 | 2.00 | 0 | 0 | 0 | 0 | 4BS | 2B | 2B | 0 | 0 |
| | 1.00 | 0 | 0 | 0 | 0 | 4BS | 2B | 2B | 0 | 0 |
| | .500 | 0 | 0 | 0 | 0 | 4BS | 2BS | 2B | 0 | 0 |

| Cmpd No. | Sgbt | Lmqr | Jiwe | Mngy | Mstd | RrPw | Tmto | Vele |
|---|---|---|---|---|---|---|---|---|
| 1 | 0 | 0 | 0 | 4BS | 3BS | 5D | 5D | 0 |
| | 4BS | 5D | 5D | 4BS | 4BS | 4BS | 5D | 3BS |
| | 3BS | 4BS | 4BS | 4BS | 4BS | 3BS | 4BS | 3BS |
| | 3BS | 2BS | 0 | 4BS | 3BS | 3BS | 4BS | 3BS |

-continued

POSTEMERGENCE

| | | | | | | | | |
|---|---|---|---|---|---|---|---|---|
| 2 | 0 | 0 | 0 | 2BS | 1 | 5D | 3BS | 0 |
| | 4BS | 5D | 4BS | 3BS | 3BS | 4BS | 3BS | 5D |
| | 4BS | 5D | 4BS | 3BS | 2BS | 4BS | 4BS | 5D |
| | 3BS | 5D | 3BS | 3BS | 2BS | 3BS | 3BS | 4BS |
| 3 | 0 | 0 | 0 | 1 | 1 | 1 | 1 | 0 |
| 4 | 5D | 5D | 5D | 5D | 5D | 5D | 5D | 5D |
| | 5D | 5D | 5D | 5D | 5D | 5D | 5D | 5D |
| | 4BS | 5D | 5D | 5D | 5D | 5D | 5D | 5D |
| 5 | 0 | 0 | 0 | 3BS | 2BS | 5D | 5D | 0 |
| | 0 | 0 | 0 | 0 | 0 | 0 | 0 | 0 |
| | 1 | 1 | 1 | 2B | 1 | 2BS | 3BS | 1 |
| | 1 | 1 | 1 | 1 | 1 | 1 | 2B | 1 |
| 6 | 0 | 0 | 0 | 2BS | 1 | 4BS | 4BS | 0 |
| | 2S | 3BS | 2BS | 3SB | 1 | 4BS | 3CBS | 3BS |
| | 1 | 2B | 3BS | 2BS | 1 | 3BS | 3BS | 3BS |
| | 1 | 1 | 2BS | 1 | 1 | 1 | 2CB | 2BS |
| 7 | 0 | 0 | 0 | 5D | 3BS | 5D | 5D | 0 |
| 8 | 0 | 0 | 0 | 3BS | 1 | 3BS | 5D | 0 |
| | 2BS | 2BS | 5D | 4BS | 2B | 4BS | 5D | 5D |
| | 2B | 1 | 4BS | 4BS | 1 | 3BS | 4BS | 4BS |
| | 2BS | 1 | 4BS | 2BS | 2BS | 4BS | 4BS | 3SB |
| 52 | 0 | 0 | 4BS | 3SB | 2SB | 2SB | 0 | 1 |
| | 0 | 0 | 4BS | 3SB | 1 | 3SB | 0 | 1 |
| | 0 | 0 | 4BS | 2B | 1 | 2B | 0 | 1 |
| 27 | 0 | 0 | 0 | 2B | 1 | 5D | 2BF | 0 |
| | 0 | 0 | 4BS | 4SBF | 0 | 5D | 0 | 3SB |
| | 0 | 0 | 4BS | 4SBF | 0 | 5D | 0 | 3SB |
| | 0 | 0 | 4BS | 3BS | 0 | 5D | 0 | 2SB |
| 26 | 0 | 0 | 0 | 5D | 4BS | 5D | 5D | 0 |
| | 5D | 5D | 5D | 5D | 3BS | 5D | 5D | 5D |
| | 5D | 5D | 4BS | 5D | 2B | 5D | 5D | 5D |
| | 5D | 4BS | 4BS | 4BS | 1 | 5D | 5D | 5D |
| 46 | 0 | 0 | 0 | 1 | 1 | 1 | 1 | 0 |
| 47 | 0 | 0 | 1 | 1 | 2BS | 3BS | 0 | 1 |
| | 0 | 0 | 1 | 1 | 1 | 1 | 0 | 1 |
| | 0 | 0 | 1 | 1 | 1 | 1 | 0 | 1 |
| 49 | 0 | 0 | 2B | 2B | 0 | 3BS | 0 | 1 |
| | 0 | 0 | 2BS | 2B | 0 | 3BS | 0 | 1 |
| | 0 | 0 | 1 | 1 | 0 | 2BS | 0 | 1 |
| 48 | 0 | 0 | 5D | 4BS | 4BS | 5D | 0 | 5D |
| | 0 | 0 | 5D | 4BS | 3BS | 5D | 0 | 5D |
| | 0 | 0 | 4BS | 4BS | 3BSP | 4BS | 0 | 5D |
| 51 | 0 | 0 | 5D | 4BS | 0 | 5D | 0 | 5D |
| | 0 | 0 | 5D | 4BS | 0 | 5D | 0 | 5D |
| | 0 | 0 | 5D | 4BS | 0 | 5D | 0 | 5D |
| 16 | 0 | 0 | 0 | 2BS | 1 | 2BS | 3BS | 0 |
| | 3BS | 3BS | 4BS | 3BS | 2S | 4BS | 4BS | 2BS |
| | 2BS | 2BS | 4BS | 2BS | 1 | 3BS | 3BS | 2SB |
| | 2BS | 2BS | 3BS | 2BS | 1 | 4BS | 3BS | 2SB |
| 17 | 0 | 0 | 0 | 5D | 3BS | 5D | 5D | 0 |
| | 3BS | 5D | 3BS | 4BS | 1 | 5D | 4BS | 4BS |
| | 3BS | 4BS | 3BS | 3BS | 1 | 5D | 4BS | 3BS |
| | 3BS | 3BS | 2B | 2BS | 1 | 4BS | 4BS | 3BS |
| 18 | 0 | 0 | 0 | 4BS | 4BS | 5D | 5D | 0 |
| | 4BS | 5D | 4BS | 5D | 3BS | 5D | 5D | 1 |
| | 2BS | 5D | 5D | 5D | 4BS | 4BS | 5D | 1 |
| | 3BS | 5D | 2B | 4BS | 3BS | 4BS | 5D | 1 |
| 19 | 0 | 0 | 0 | 3BS | 2B | 4BSB | 2BS | 0 |
| 21 | 0 | 0 | 0 | 2C | 2C | 1 | 1 | 0 |
| 22 | 0 | 0 | 0 | 5D | 5D | 5D | 5D | 0 |
| | 5D | 5D | 5D | 5D | 4BS | 5D | 5D | 5D |
| | 5D | 5D | 5D | 5D | 4BS | 5D | 5D | 5D |
| | 5D | 3BS | 5D | 5D | 3BS | 5D | 5D | 4BS |
| 15 | 0 | 0 | 0 | 4BS | 4BS | 4BS | 5D | 0 |
| | 2B | 4BS | 5D | 3BS | 3BS | 2BS | 5D | 1 |
| | 2B | 1 | 5D | 3BS | 2BS | 2BS | 5D | 1 |
| | 1 | 1 | 5D | 3BS | 2B | 2BS | 4BS | 1 |
| | 2S | 2S | 4BS | 2BS | 1 | 2BS | 3BS | 1 |
| | 2BS | 2S | 4BS | 2B | 2B | 3BS | 3BS | 1 |
| | 1 | 1 | 3BS | 2B | 1 | 2SB | 2B | 1 |
| 13 | 0 | 0 | 0 | 3BS | 1 | 4BS | 5D | 0 |
| | 4BS | 0 | 0 | 5D | 2B | 3BS | 5D | 4BS |
| | 4BS | 0 | 0 | 5D | 2BS | 2BS | 5D | 3BS |
| | 3BS | 0 | 0 | 4BS | 2B | 2BS | 5D | 3BS |
| | 3BS | 1 | 3BS | 5D | 2BS | 3BS | 5D | 3BS |
| | 2BS | 1 | 3BS | 4BS | 3BS | 3BS | 5D | 3BS |
| | 2BS | 1 | 3BS | 3BS | 1 | 4BS | 5D | 3BS |
| 9 | 0 | 0 | 0 | 3BS | 2S | 2BS | 5D | 0 |
| | 1 | 1 | 3BS | 3BS | 2BS | 2B | 5D | 1 |
| | 2B | 1 | 3BS | 3BS | 3BS | 2B | 5D | 1 |
| | 1 | 1 | 4BS | 2BS | 1 | 2B | 4BS | 2B |

-continued

| | | | POSTEMERGENCE | | | | | |
|---|---|---|---|---|---|---|---|---|
| 11 | 0 | 0 | 0 | 3BS | 3BS | 2BS | 5D | 0 |
| | 2S | 1 | 1 | 3BS | 3BS | 1 | 5D | 2B |
| | 1 | 1 | 1 | 3BS | 2SB | 1 | 5D | 2B |
| | 1 | 1 | 1 | 3BS | 2BS | 1 | 4BS | 1 |
| 12 | 0 | 0 | 0 | 1 | 1 | 1 | 1 | 0 |
| 14 | 0 | 0 | 0 | 2CB | 2BS | 2BS | 2B | 0 |
| | 1 | 1 | 0 | 2SB | 2B | 1 | 1 | 1 |
| | 1 | 1 | 0 | 1 | 1 | 1 | 1 | 1 |
| | 1 | 1 | 0 | 1 | 1 | 1 | 1 | 1 |
| 28 | 0 | 0 | 0 | 0 | 0 | 5D | 5D | 0 |
| | 0 | 0 | 0 | 4BS | 3BS | 4BS | 0 | 4BS |
| | 0 | 0 | 0 | 4BS | 2B | 4SB | 0 | 4BSF |
| | 0 | 0 | 0 | 4SBF | 2B | 4SB | 0 | 4SB |
| 33 | 0 | 0 | 0 | 0 | 0 | 5D | 5D | 0 |
| | 0 | 0 | 0 | 4BS | 4BS | 4BS | 4BS | 0 |
| 34 | 0 | 0 | 0 | 4BS | 2B | 5D | 5D | 0 |
| | 5D | 5D | 0 | 5D | 2BS | 5D | 5D | 5D |
| | 5D | 5D | 0 | 4BS | 2BS | 5D | 5D | 5D |
| | 5D | 5D | 0 | 4BS | 3BS | 5D | 5D | 5D |
| 56 | 0 | 0 | 0 | 0 | 0 | 5D | 4BS | 0 |
| | 0 | 0 | 0 | 4BS | 3CBS | 4BS | 0 | 2B |
| | 0 | 0 | 0 | 3BS | 2B | 3SB | 0 | 2B |
| | 0 | 0 | 0 | 2SB | 1 | 2B | 0 | 2B |
| 54 | 0 | 0 | 0 | 0 | 0 | 5D | 5D | 0 |
| | 0 | 0 | 0 | 2SB | 4BS | 5D | 0 | 2SB |
| | 0 | 0 | 0 | 2SB | 3BS | 4BS | 0 | 2SB |
| | 0 | 0 | 0 | 2SB | 2BS | 4BS | 0 | 2SB |
| 55 | 0 | 0 | 0 | 0 | 0 | 5D | 5D | 0 |
| | 0 | 0 | 0 | 4SB | 3SB | 5 | 0 | 5D |
| | 0 | 0 | 0 | 4SB | 4SB | 5D | 0 | 5D |
| | 0 | 0 | 0 | 3SB | 3SB | 4BS | 0 | 5D |
| 58 | 0 | 0 | 0 | 0 | 0 | 5D | 5D | 0 |
| | 0 | 0 | 0 | 4BS | 0 | 5D | 0 | 5D |
| | 0 | 0 | 0 | 4BS | 0 | 5D | 0 | 5D |
| | 0 | 0 | 0 | 4BS | 0 | 5D | 0 | 5D |
| 59 | 0 | 0 | 0 | 0 | 0 | 5D | 5D | 0 |
| | 0 | 0 | 0 | 4BS | 4BS | 5D | 0 | 5D |
| | 0 | 0 | 0 | 4BS | 4BS | 4BS | 0 | 5D |
| | 0 | 0 | 0 | 4BS | 4BS | 4BS | 0 | 5D |
| 62 | 0 | 0 | 0 | 0 | 0 | 5 | 5 | 0 |
| | 0 | 0 | 0 | 5D | 5D | 5D | 0 | 5D |
| | 0 | 0 | 0 | 5D | 5D | 5D | 0 | 5D |
| | 0 | 0 | 0 | 5D | 5D | 5D | 0 | 5D |
| 10 | 0 | 0 | 0 | 0 | 0 | 5D | 4SB | 0 |
| | 0 | 0 | 0 | 2B | 2F | 2B | 0 | 3SB |
| | 0 | 0 | 0 | 2B | 2SB | 2B | 0 | 2B |
| | 0 | 0 | 0 | 2B | 2SB | 2B | 0 | 2B |
| 66 | 0 | 0 | 0 | 0 | 0 | 5D | 5D | 0 |
| | 0 | 0 | 0 | 5D | 5D | 5D | 0 | 5D |
| | 0 | 0 | 0 | 5D | 5D | 5D | 0 | 5D |
| | 0 | 0 | 0 | 5D | 5D | 5D | 0 | 5D |
| 67 | 0 | 0 | 0 | 0 | 0 | 5D | 5D | 0 |
| | 0 | 0 | 0 | 5D | 5D | 5D | 0 | 5D |
| | 0 | 0 | 0 | 5D | 5D | 5D | 0 | 5D |
| | 0 | 0 | 0 | 5D | 5D | 5D | 0 | 5D |
| 58 | 0 | 0 | 5D | 5D | 4BS | 5D | 0 | 5D |
| | 0 | 0 | 0 | 5D | 2BS | 5D | 0 | 5D |
| | 0 | 0 | 5D | 4B | 3BS | 5DB | 0 | 5DB |
| 76 | 0 | 0 | 5D | 5D | 5D | 5D | 0 | 5D |
| | 0 | 0 | 5D | 5D | 5D | 5D | 0 | 5D |
| | 0 | 0 | 5D | 5D | 5D | 5D | 0 | 5D |
| 82 | 0 | 0 | 5D | 3SB | 5D | 3SB | 0 | 5D |
| | 0 | 0 | 5D | 2SB | 5D | 2SB | 0 | 3SB |
| | 0 | 0 | 4B | 2SB | 4B | 2SB | 0 | 4B |
| 53 | 0 | 0 | 4BS | 3SB | 2BS | 3SB | 0 | 2SB |
| | 0 | 0 | 4BS | 3SB | 2BS | 2B | 0 | 2SB |
| | 0 | 0 | 4BS | 3SB | 2SB | 2SB | 0 | 1 |

In addition, representative compounds of Formula A were further tested as follows:

TEST 2

Method:
Plant Material: Seeds of the desired test species are planted in sandy loam soil in plastic pots with a surface area of 103 sq. cm. In some instances, a fungicide treatment is used on individual species to insure highly reliable plant material is available for each test. In other instances, a seed treatment such as scarification by chemical or physical means is required to insure germination. The soil is typically of pH range 5-7.5 and organic matter content is less than 1.0% for preemergent testing and 0.5% for postemergent testing. The following species may be used in each test:

| Name | Abbreviation |
|---|---|
| Cotton (*Gossypium hirsutum*) | Cttn |

-continued

| Name | Abbreviation |
|---|---|
| Oilseed Rape (*Brassica napus*) | OlRp |
| Soybean (*Glycine max*) | Sybn |
| Sugarbeet (*Beta vulgaris*) | Sgbt |
| Cocklebur (*Xanthium strumarium*) | Ckbr |
| Jimsonweed (*Datura stramonium*) | Jmwd |
| Lambsquarter (*Chenopodium album*) | Lmqr |
| Sunflower (*Helianthus annuus*) | Sunf |
| Morningglory (Ipomoea sp.) | Mngy |
| Redroot Pigweed (*Amaranthus retroflexus*) | RdPw |
| Velvetleaf (*Abutilon theophrasti*) | Vele |
| Speedwell (*Veronica persica*) | Spwl |
| Wild buckwheat (*Polygonum convolvulus*) | WiBk |
| Corn (*Zea mays*) | Corn |
| Rice (*Oryza sativa*) | Rice |
| Wheat (*Triticum aestivum*) | Whet |
| Blackgrass (*Alopecurus mysosuroides*) | Blkg |
| Barnyardgrass (*Echinochloa crus-galli*) | Bnyd |
| Giant foxtail (*Setaria faberi*) | GiFx |
| Johnsongrass (*Sorghum halepense*) | Jngr |
| Wild oat (*Avena fatua*) | WiOa |
| Yellow nutsedge (*Cyperus esculentus*) | YlNt |

For preemergent testing, following chemical application, the pots are placed in a greenhouse, gently top-watered to move the herbicide into the seed zone, and the seeds are allowed to germinate. The plants are grown for three weeks in a greenhouse typically maintained on a 25°–33° C. day/15°–20° C. night thermoperiod and a 14 hour photoperiod. Supplemental lighting is provided when necessary by overhead 1000 watt multi-vapor lamps. The plants are regularly top-watered.

For postemergent testing, the plants are grown 7–20 days in a greenhouse typically maintained on a 25°–33° C. day/15°–20° C. night thermoperiod and a 14 hour photoperiod. Supplemental lighting is provided when necessary by overhead 1000 watt multi-vapor lamps. The plots receive regular nutrient additions. Chemical applications are typically made when plants have reached the first to second true leaf stage. Following chemical application, plants are maintained in the greenhouse. Pots are watered by sub-irrigation to prevent wash-off of the chemical from the leaf surface.

Chemical Weighing, Dilution, and Application:

Weighing: Samples of the test chemicals are weighed into 10ml glass vials. The amount weighed depends on the high rate in the test and is listed below:

| High rate (kg/ha) | Quantity weighed (mg) |
|---|---|
| *Preemergent testing:* | |
| 4.48 | 36.3 |
| 2.24 | 18.2 |
| 1.12 | 9.1 |
| 0.56 | 4.54 |
| 0.28 | 2.27 |
| 0.14 | 1.13 |
| *Postemergent testing:* | |
| 2000 | 60 |
| 1000 | 30 |
| 500 | 15 |
| 250 | 7.5 |
| 125 | 3.75 |
| 62.5 | 1.88 |
| 31.2 | 0.94 |
| 15.6 | 0.47 |

Dilution for preemergent testing: A concentrated stock solution is made by adding 8 mL of acetone:DMSO (97:3) v/v) to the weighed sample. Most samples dissolve readily. When chemicals do not dissolve readily, gentle warming or sonication are used to increase solubilization. Spray solutions for postemergence testing are formulated at five rates, a high rate (x), and four half-fold dilutions ($\frac{1}{2}$x, $\frac{1}{4}$x, $\frac{1}{8}$x, and 1/16x). The spray solutions are made by injecting aliquots of the stock solution into a spray solution comprised of water and Tween-20 99.9:0.1 v/v). The mixture used to formulate each concentration is specified below:

| Concentration | Aliquot of stock soln.(ml) | Amount of spray soln.(ml) |
|---|---|---|
| x | 4 | 8.5 |
| $\frac{1}{2}$x | 2 | 10.5 |
| $\frac{1}{4}$x | 1 | 11.5 |
| $\frac{1}{8}$x | 0.5 | 12.0 |
| 1/16x | 0.25 | 12.25 |

Dilution for postemergent testing: A concentrated solution is made by adding 4 ml of acetone:DMSO (97:3) v/v to the weighed sample. Most samples dissolve readily. When chemicals do not dissolve readily, gentle warming or sonication are used to increase solubilization. Spray solutions for postemergence testing are formulated at five rates, a high rate (x), and four half-fold dilutions ($\frac{1}{2}$x, $\frac{1}{4}$x, $\frac{1}{8}$x, and 1/16x). The spray solutions are made by injecting aliquots of the stock solution into a spray solution comprised of acetone, water isopropyl alcohol, DMSO, Atplus 411F, and Triton X-155 (48.5:39:10:1.5:1.0:0.02) v/v). The mixture used to formulate each concentration is specified below:

| Concentration | Aliquot of stock soln.(ml) | Amount of spray soln.(ml) |
|---|---|---|
| x | 2 | 13 |
| $\frac{1}{2}$x | 1 | 14 |
| $\frac{1}{4}$x | 0.5 | 14.5 |
| $\frac{1}{8}$x | 0.25 | 14.75 |
| 1/16x | 0.125 | 14.875 |

Application for preemergent testing: Solutions are sprayed onto the soil of pots seeded with the test species. The applications are made with a Cornwall 5.0 ml glass syringe fitted with a TeeJet TN-3 hollow cone nozzle. Approximately 2.5 mL of spray solution is applied to the soil in each 10 cm pot. The volume of spray solution and adjuvant consistently provide thorough spray coverage.

Application for postemergent testing: Solutions are sprayed onto the foliage of test plants with a Cornwall 2.0 mL glass syringe fitted with a TeeJet TN-3 hollow cone nozzle. Approximately 1.5 mL of spray solution is applied to the plants in each 7.6 cm pot. The volume of spray solution and adjuvant consistently provide thorough spray coverage.

Evaluation for preemergent testing: Assessment of weed control and crop injury are made three weeks after application of the test chemicals. Plant injury is visually assessed on a scale of 0–100%, with 0% equal to no injury, and 100% equal to complete kill. A blank space indicates no evaluation was performed.

Evaluation for postemergent testing: Assessment of weed control and crop injury are made two weeks after application of the test chemicals. Plant injury is visually assessed on a scale of 0–100% with 0% equal to no injury and 100% equal to complete kill. A blank space indicates no evaluation was performed.

The results obtained were as follows:

| Cmpd No. | Conc | Cttn | OlRp | Sybn | Sght | Sunf | Mngy | RdPw | Vele | WdBk | Corn | Rice | Whet | Blkg | Bnyd | GlFx | Jngr | WlOa |
|---|---|---|---|---|---|---|---|---|---|---|---|---|---|---|---|---|---|
| | | | | | | | | | | PREEMERGENCE | | | | | | | |
| 17 | 1.12 | 35 | 10 | 25 | 75 | 45 | 90 | 100 | 100 | 100 | 50 | 10 | 10 | 50 | 90 | 100 | 100 | |
| | .56 | 10 | 0 | 0 | 65 | 15 | | 100 | 100 | 100 | 65 | 5 | 5 | 75 | 90 | 100 | 50 | |
| | .28 | 0 | 0 | 0 | 20 | 0 | | 100 | 40 | 95 | 15 | 0 | 0 | 30 | 65 | 70 | 0 | |
| | .14 | 0 | 0 | 0 | 0 | 0 | 25 | 85 | 0 | 50 | 0 | 0 | 0 | 0 | 10 | 40 | 0 | |
| | .07 | 0 | 0 | 0 | 0 | 0 | 10 | 50 | 0 | | 0 | 0 | 0 | 0 | 0 | 0 | 0 | |
| 48 | 1.12 | 20 | 10 | 10 | 40 | 25 | 15 | 100 | 100 | 100 | 10 | 10 | 0 | 45 | 80 | 95 | 60 | 60 |
| | .56 | 10 | 0 | 0 | 25 | 5 | 0 | 100 | 95 | 100 | 5 | 5 | 0 | 30 | 55 | 75 | 50 | 50 |
| | .28 | 0 | 0 | 0 | 0 | 0 | 0 | 85 | 40 | 100 | 0 | 0 | 0 | 35 | 55 | 60 | 25 | 10 |
| | .14 | 0 | 0 | 0 | 0 | 0 | 0 | 0 | 0 | 0 | 0 | 0 | 0 | 0 | 0 | 0 | 0 | 0 |
| | .07 | 0 | 0 | 0 | 0 | 0 | 0 | 0 | 0 | | 0 | 0 | 0 | 0 | 0 | 0 | 0 | 0 |
| 41 | .035 | 35 | 75 | 95 | 100 | 35 | 80 | 100 | 100 | 100 | 85 | 75 | 70 | | 100 | 100 | 100 | 60 |
| | .018 | 35 | 10 | 25 | 100 | 25 | | 100 | 100 | | 65 | 30 | 50 | | 100 | 95 | 95 | 25 |
| | .009 | 10 | 0 | 0 | 100 | 10 | 15 | 100 | 100 | 0 | 55 | 10 | 10 | | 95 | 95 | 100 | 10 |
| | .004 | 0 | 0 | 0 | 45 | 0 | 20 | 100 | 40 | | 25 | 0 | 0 | | 85 | 65 | 75 | 0 |
| | .002 | 0 | 0 | 0 | 35 | 0 | 0 | 20 | 0 | | 0 | 0 | 0 | | 65 | 10 | 60 | 0 |
| 49 | 1.12 | 0 | 0 | 0 | 0 | 0 | 0 | 0 | 0 | | 0 | 10 | 0 | 0 | 0 | 0 | 20 | 0 |
| | .56 | 0 | 0 | 0 | 0 | 0 | 0 | 0 | 0 | 0 | 0 | 5 | 0 | 0 | 0 | 0 | 0 | 0 |
| | .28 | 0 | 0 | 0 | 0 | 0 | 0 | 0 | 0 | 0 | 0 | 0 | 0 | 0 | 0 | 0 | 0 | 0 |
| | .14 | 10 | 0 | 0 | 0 | 0 | 0 | 0 | 0 | 0 | 0 | 0 | 0 | 0 | 0 | 0 | 0 | 0 |
| | .070 | 0 | 0 | 0 | 0 | 0 | 0 | 0 | 0 | | 0 | 0 | 0 | | 0 | 0 | 0 | 0 |
| 40 | .018 | 10 | 10 | 0 | 70 | 30 | 25 | 90 | 90 | | 40 | 35 | 100 | | 95 | 70 | 90 | 100 |
| | .009 | 0 | 0 | 0 | 30 | 15 | 30 | 80 | 70 | | 30 | 40 | 30 | | 80 | 60 | 90 | 100 |
| | .004 | 0 | 0 | 0 | 10 | 0 | 0 | 20 | 25 | | 0 | 10 | 10 | | 35 | 15 | 65 | 80 |
| | .002 | 0 | 0 | 0 | 0 | 0 | 0 | 0 | 0 | | 0 | 0 | 0 | | 10 | 10 | 0 | 75 |
| | .001 | 0 | 0 | 0 | 0 | 0 | 0 | 0 | 0 | | 0 | 0 | 0 | | 0 | 0 | 0 | 0 |
| 62 | .56 | 100 | 100 | 60 | 100 | 95 | 100 | | 100 | 100 | 90 | 95 | 95 | 100 | 100 | 100 | 100 | 100 |
| | .28 | 100 | 100 | 40 | 100 | 90 | 100 | | 100 | 100 | 80 | 95 | 95 | 100 | 98 | 100 | 100 | 80 |
| | .14 | 95 | 100 | 30 | 95 | 75 | 100 | | 100 | 100 | 70 | 90 | 90 | 90 | 98 | 99 | 99 | 75 |
| | .14 | 70 | 100 | 20 | 100 | 75 | 99 | 99 | 100 | 100 | 30 | 85 | 70 | 90 | 99 | 99 | 99 | 80 |
| | .07 | 90 | 90 | 10 | 80 | 80 | 90 | | 100 | 100 | 70 | 90 | 80 | 50 | 98 | 90 | 95 | 70 |
| | .07 | 60 | 85 | 10 | 95 | 70 | 60 | | 100 | 100 | 40 | 85 | 60 | 80 | 80 | 50 | 90 | 50 |
| | .035 | 40 | 80 | 10 | 80 | 50 | 20 | | 100 | 100 | 5 | 70 | 50 | 25 | 40 | 100 | 70 | 70 |
| | .035 | 75 | 40 | 50 | 40 | 50 | 80 | | 100 | | 40 | 60 | 60 | 20 | 100 | 50 | 100 | 30 |
| | .018 | 30 | 25 | 10 | 20 | 30 | 0 | 95 | 40 | 70 | 0 | 20 | 25 | 10 | 40 | 100 | 100 | 20 |
| | .009 | 30 | 10 | 10 | 100 | 10 | 15 | 65 | 100 | | 25 | 85 | 95 | 100 | 90 | 100 | 100 | 95 |
| 63 | .56 | 100 | 100 | 95 | 100 | 80 | 100 | 100 | 100 | | 10 | 85 | 80 | 95 | 100 | 100 | 98 |
| | .28 | 100 | 100 | 99 | 100 | 90 | 100 | 100 | 100 | 100 | 20 | 80 | 40 | 70 | 100 | 100 | 100 | 85 |
| | .14 | 98 | 100 | 99 | 100 | 70 | 100 | | 100 | | 25 | 70 | 60 | 95 | 60 | 95 | 99 | 50 |
| | .14 | 99 | 100 | 99 | 100 | 70 | 85 | 99 | 100 | | 10 | 20 | 20 | 50 | 95 | 85 | 99 | 80 |
| | .07 | 70 | 90 | 70 | 80 | 50 | 60 | | 100 | 100 | 0 | 30 | 50 | 30 | 50 | 75 | 95 | 30 |
| | .07 | 70 | 100 | 10 | 80 | 60 | 80 | 99 | 100 | | 0 | 20 | 10 | 80 | 40 | 50 | 70 | 60 |
| | .035 | 40 | 90 | 50 | 30 | 10 | 10 | | 100 | 100 | 30 | 30 | 0 | 30 | 90 | 100 | 90 | 20 |
| 38 | .035 | 25 | 30 | 10 | 80 | 0 | 15 | 95 | 70 | | 20 | 20 | 15 | 0 | 85 | 85 | 95 | 10 |
| | .018 | 10 | 10 | 10 | 30 | 0 | 40 | 100 | 75 | 95 | 15 | 30 | 10 | 30 | 70 | 70 | 85 | 0 |
| | .009 | 0 | 0 | 15 | 40 | 0 | 30 | 100 | 65 | 90 | 0 | 20 | 15 | 15 | 65 | 85 | 70 | 25 |
| | .07 | 15 | 0 | 0 | 20 | 0 | 0 | 95 | 50 | | 30 | 10 | 10 | 10 | 50 | 30 | 40 | 0 |
| | .035 | 0 | 0 | 0 | 0 | 0 | 0 | 90 | 30 | | 15 | 0 | 0 | 0 | | | | 0 |
| | .018 | 0 | 0 | 0 | 0 | 0 | 0 | 0 | 20 | | 0 | 0 | 0 | 0 | | | | 0 |
| | .009 | 0 | 0 | 0 | 0 | 0 | 0 | | | | 0 | 0 | | | | | | 0 |
| | .004 | | | | | | | | | | | | | | | | | |

-continued

| Cmpd No. | Conc | Cttn | OlRp | Sybn | Sgbt | Sunf | Mngy | RdPw | Vele | WdBk | Corn | Rice | Whet | Blkg | Bnyd | GiFx | Jngr | WiOa |
|---|---|---|---|---|---|---|---|---|---|---|---|---|---|---|---|---|---|---|
| 42 | .004 | 0 | 0 | 0 | 0 | 5 | 10 | 10 | 0 | | 0 | 5 | 15 | | 0 | 0 | 0 | 10 |
| | .002 | 0 | 0 | 0 | 0 | 0 | 5 | 15 | 0 | | 0 | 0 | 0 | | 0 | 0 | 0 | 0 |
| | .001 | 0 | 0 | 0 | 0 | 0 | 0 | 0 | 0 | | 0 | 0 | 0 | | 0 | 0 | 0 | 0 |
| | .0005 | 0 | 0 | 0 | 0 | 0 | 0 | 0 | 0 | | 0 | 0 | 0 | | 0 | 0 | 0 | 0 |
| | .00025 | 0 | 0 | 0 | 0 | 0 | 0 | 0 | 0 | | 0 | | 0 | | 0 | 0 | 0 | 0 |
| 58 | .56 | 25 | 70 | 50 | 85 | 50 | 70 | 100 | 100 | | 60 | | 50 | 95 | 75 | 100 | 95 | 60 |
| | .28 | 30 | 80 | 35 | 80 | 45 | 35 | 100 | 100 | | 65 | | 40 | 80 | 95 | 100 | 100 | 30 |
| | .14 | 20 | 35 | 15 | 60 | 20 | 0 | 15 | 100 | | 15 | | 5 | 80 | 50 | 95 | 80 | 10 |
| | .07 | 0 | 10 | 0 | 35 | 5 | 0 | 0 | 30 | | 5 | | 0 | 25 | 60 | 80 | 85 | 5 |
| | .035 | 0 | 0 | 0 | 15 | 0 | 0 | 0 | 0 | | 0 | | 0 | 10 | 60 | 30 | 70 | 0 |
| 52 | 2.24 | 20 | 0 | 0 | 0 | 60 | 100 | | | 100 | 95 | 75 | 30 | 95 | 95 | 100 | 100 | 95 |
| | 1.12 | 20 | 0 | 0 | 0 | 40 | 100 | | | 100 | 80 | 60 | 20 | 85 | 80 | 100 | 95 | 80 |
| | .56 | 0 | 0 | 0 | 0 | 20 | 60 | | | 100 | 30 | 0 | 0 | 50 | 95 | 90 | 70 | 50 |
| | .28 | 0 | 0 | 0 | 0 | 0 | 50 | | | 100 | 10 | 0 | 0 | 20 | 20 | 30 | 30 | 0 |
| | .14 | 0 | 0 | 0 | 0 | 0 | 0 | | | 0 | 0 | 0 | 0 | 0 | 0 | 0 | 0 | 0 |
| 50 | .14 | 60 | 70 | 60 | 90 | 50 | 99 | | 30 | | 70 | 50 | 50 | 80 | 99 | 99 | 99 | 95 |
| | .07 | 60 | 40 | 50 | 80 | 30 | 99 | | 50 | | 60 | 50 | 50 | 99 | 99 | 99 | 99 | 90 |
| | .035 | 50 | 30 | 40 | 50 | 30 | 70 | | 50 | | 40 | 10 | 40 | 80 | 98 | 99 | 99 | 75 |
| | .018 | 30 | 30 | 30 | 30 | 20 | 50 | | 40 | | 25 | 0 | 20 | 70 | 70 | 50 | 90 | 60 |
| | .009 | 20 | 10 | 30 | 30 | 20 | 35 | | 20 | | 25 | 0 | 20 | 50 | 50 | 50 | 80 | 50 |

| | | | | | | | | | | POSTEMERGENCE | | | | | | | | | | | | | |
|---|---|---|---|---|---|---|---|---|---|---|---|---|---|---|---|---|---|---|---|---|---|---|---|
| Cmpd No. | Conc | Cttn | OlRp | Sybn | Sgbt | Ckbr | Jmwd | Lmqr | Mngy | RdPw | Vcle | Spwl | WdBk | Corn | Rice | Whet | Blkg | Bnyd | GlFx | Jngr | WiOa | YlNt |
| 17 | 1000 | 85 | 0 | 75 | 70 | 70 | 100 | 100 | 100 | 100 | 100 | 80 | 100 | 20 | 25 | 10 | 30 | 100 | 30 | 50 | 10 | 20 |
|  | 500 | 85 | 0 | 60 | 50 | 40 | 98 | 100 | 100 | 100 | 98 | 85 | 100 | 20 | 20 | 0 | 0 | 98 | 20 | 70 | 0 | 0 |
|  | 250 | 95 | 0 | 50 | 50 | 40 | 95 | 100 | 100 | 95 | 98 | 40 | 100 | 20 | 20 | 0 | 0 | 100 | 40 | 70 | 0 | 0 |
|  | 125 | 75 | 0 | 25 | 20 | 40 | 50 | 70 | 70 | 20 | 70 | 30 | 80 | 20 | 15 | 0 | 0 | 30 | 40 | 20 | 0 | 0 |
|  | 62.5 | 40 | 30 | 25 | 10 | 40 | 40 | 40 | 0 | 30 | 0 | 20 | 60 | 20 | 15 | 0 | 0 | 0 | 0 | 0 | 0 | 0 |
| 48 | 1000 | 99 | 30 | 30 | 55 | 50 | 100 | 100 | 100 | 100 | 100 | 60 | 100 | 20 | 25 | 25 | 50 | 40 | 40 | 20 | 0 | 0 |
|  | 500 | 98 | 30 | 25 | 55 | 40 | 90 | 100 | 100 | 100 | 98 | 60 | 80 | 20 | 20 | 20 | 30 | 80 | 20 | 60 | 0 | 0 |
|  | 250 | 60 | 30 | 20 | 55 | 40 | 80 | 98 | 100 | 90 | 90 | 60 | 100 | 20 | 25 | 20 | 30 | 40 | 30 | 20 | 0 | 0 |
|  | 125 | 50 | 0 | 20 | 60 | 35 | 85 | 98 | 70 | 45 | 45 | 0 | 80 | 20 | 25 | 10 | 0 | 40 | 30 | 60 | 0 | 0 |
|  | 62.5 | 40 | 40 | 20 | 45 | 0 | 40 | 60 | 0 | 40 | 40 | 0 | 50 | 0 | 10 | 0 | 0 | 40 | 20 | 0 | 0 | 0 |
| 49 | 1000 | 0 | 40 | 15 | 0 | 0 | 0 | 0 | 0 | 0 | 0 | 0 | 0 | 20 | 0 | 0 | 0 | 0 | 0 | 0 | 0 | 0 |
|  | 500 | 0 | 40 | 15 | 0 | 0 | 0 | 0 | 0 | 0 | 0 | 0 | 0 | 0 | 0 | 0 | 0 | 0 | 0 | 0 | 0 | 0 |
|  | 250 | 0 | 30 | 15 | 0 | 0 | 0 | 0 | 0 | 0 | 0 | 0 | 0 | 20 | 0 | 0 | 0 | 0 | 0 | 0 | 0 | 0 |
|  | 125 | 0 | 30 | 10 | 0 | 0 | 0 | 0 | 0 | 0 | 0 | 0 | 0 | 0 | 0 | 0 | 0 | 0 | 0 | 0 | 0 | 0 |
|  | 62.5 | 0 | 0 | 0 | 0 | 0 | 0 | 0 | 0 | 0 | 0 | 0 | 0 | 10 | 0 | 0 | 0 | 0 | 0 | 0 | 0 | 0 |
| 51 | 500 | 100 | 80 | 78 | 100 | 80 | 100 | 100 | 100 | 100 | 100 | 100 | 98 | 80 | 45 | 35 | 100 | 100 | 100 | 100 | 85 | 35 |
|  | 250 | 100 | 80 | 70 | 90 | 60 | 100 | 100 | 30 | 100 | 100 | 100 | 98 | 75 | 35 | 35 | 70 | 98 | 98 | 45 | 20 | 35 |
|  | 125 | 100 | 0 | 60 | 40 | 50 | 98 | 100 | 100 | 100 | 100 | 100 | 70 | 30 | 40 | 20 | 90 | 99 | 80 | 45 | 35 | 20 |
|  | 62.5 | 98 | 0 | 40 | 60 | 0 | 45 | 80 | 0 | 40 | 0 | 0 | 98 | 10 | 30 | 20 | 0 | 0 | 40 | 0 | 20 | 0 |
|  | 31.25 | 20 | 30 | 20 | 30 | 0 | 0 | 70 | 0 | 0 | 20 | 0 | 20 | 0 | 25 | 20 | 0 | 0 | 0 | 0 | 0 | 30 |
| 58 | 500 | 100 | 30 | 75 | 98 | 100 | 100 | 98 | 100 | 98 | 100 | 100 | 98 | 35 | 50 | 20 | 60 | 65 | 100 | 100 | 20 | 20 |
|  | 250 | 100 | 25 | 85 | 95 | 75 | 100 | 98 | 30 | 98 | 100 | 95 | 70 | 35 | 50 | 10 | 0 | 70 | 98 | 100 | 20 | 0 |
|  | 125 | 98 | 20 | 85 | 75 | 70 | 99 | 100 | 100 | 98 | 100 | 80 | 50 | 65 | 30 | 20 | 0 | 55 | 20 | 60 | 35 | 0 |
|  | 62.5 | 55 | 0 | 30 | 40 | 60 | 98 | 80 | 90 | 70 | 85 | 0 | 40 | 0 | 20 | 0 | 0 | 35 | 0 | 60 | 20 | 0 |
|  | 31.25 | 55 | 0 | 0 | 20 | 60 | 90 | 70 | 70 | 40 | 20 | 0 | 50 | 5 | 20 | 0 | 0 | 45 | 0 | 55 | 20 | 15 |
| 24 | 31.25 | 85 | 0 | 70 | 100 | 100 | 100 | | 65 | 80 | 100 | | 100 | 5 | 20 | 15 | | 100 | 100 | 60 | 75 | 15 |
|  | 15.625 | 90 | 0 | 88 | 100 | 100 | 100 | | 100 | 70 | 100 | | 100 | 5 | 50 | 15 | | 55 | 100 | 55 | 30 | 15 |
|  | 7.813 | 75 | 0 | 70 | 50 | 100 | 100 | | 90 | 20 | 100 | | 80 | 5 | 30 | 35 | | 10 | 65 | 60 | 20 | 10 |
|  | 3.906 | 65 | 85 | 50 | 30 | 70 | 70 | | 70 | 30 | 85 | | 85 | 5 | 20 | 15 | | 10 | 75 | 50 | 20 | 25 |
|  | 1.953 | 35 | 50 | 35 | 35 | 95 | 70 | | 65 | 20 | 20 | | 100 | 25 | 20 | 15 | | 10 | 45 | 10 | 20 | 5 |
|  | .977 | 35 | 20 | 10 | 30 | 50 | 80 | | 100 | 50 | 35 | | 80 | 35 | 20 | 65 | | 45 | 100 | 30 | 20 | 30 |
| 20 | 31.25 | 100 | 0 | 50 | 50 | 80 | 100 | | 100 | 100 | 100 | | 85 | 25 | 90 | 55 | | 100 | 100 | 10 | 40 | 20 |
|  | 15.625 | 100 | 0 | 50 | 100 | 100 | 100 | | 100 | 100 | 100 | | 100 | 0 | 50 | 35 | | 20 | 100 | 75 | 35 | 0 |
|  | 7.813 | 95 | 0 | 20 | 88 | 80 | 100 | | 70 | 70 | 70 | | 85 | 0 | 20 | 20 | | 10 | 100 | 75 | 30 | 0 |
|  | 3.906 | 35 | 0 | 20 | 80 | 80 | 90 | | 70 | 80 | 80 | | 100 | 5 | 30 | 30 | | 20 | 100 | 70 | 30 | 0 |
|  | 1.953 | 35 | 0 | 35 | 70 | 50 | 50 | | 40 | 50 | 70 | | 90 | 5 | 20 | 20 | | 10 | 20 | 20 | 20 | 0 |
|  | .975 | 85 | 0 | 30 | 90 | 20 | 100 | | 50 | 80 | 75 | | 60 | 0 | 30 | 50 | | 10 | 20 | 0 | 20 | 25 |
| 4 | 15.6 | 75 | 0 | 55 | 90 | 100 | 100 | | 100 | 100 | 70 | | 100 | 15 | 85 | 45 | | 55 | 100 | 55 | 45 | 5 |
|  | 7.8 | 40 | 0 | 45 | 70 | 100 | 100 | | 50 | 75 | 0 | | 100 | 25 | 20 | 55 | | 50 | 100 | 20 | 30 | 30 |
|  | 3.9 | 20 | 0 | 50 | 40 | 100 | 100 | | 50 | 70 | 0 | | 100 | 20 | 10 | 30 | | 45 | 100 | 30 | 10 | 20 |
|  | 1.95 | 20 | 0 | 10 | 20 | 70 | 70 | | 50 | 80 | 0 | | 85 | 5 | 5 | 10 | | 5 | 90 | 10 | 5 | 5 |
|  | .975 | 40 | 0 | 55 | 10 | 20 | 50 | | 40 | 50 | 0 | | 90 | 5 | 5 | 5 | | 5 | 15 | 10 | 5 | 5 |
|  | .488 | 40 | 0 | 0 | 5 | 80 | 100 | | 50 | 50 | 65 | | 60 | 10 | 10 | 10 | | 5 | 5 | 10 | 5 | 5 |
| 4 | 62.5 | 85 | 0 | 85 | 75 | 100 | 100 | | 100 | 100 | 65 | | 100 | 10 | 80 | 90 | | 65 | 70 | 100 | 50 | 85 |
|  | 31.25 | 88 | 0 | 70 | 75 | 100 | 100 | | 100 | 100 | 50 | | 100 | 10 | 20 | 20 | | 90 | 100 | 80 | 30 | 55 |
|  | 15.625 | 80 | 0 | 50 | 90 | 100 | 100 | | 100 | 100 | 50 | | 100 | 5 | 20 | 20 | | 45 | 85 | 65 | 20 | 25 |
|  | 7.813 | 75 | 0 | 55 | 70 | 80 | 100 | | 50 | 75 | 40 | | 90 | 5 | 5 | 10 | | 10 | 80 | 10 | 5 | 10 |
|  | 3.906 | 30 | 0 | 45 | 60 | 80 | 100 | | 40 | 40 | 45 | | 100 | 5 | 20 | 20 | | 10 | 15 | 10 | 5 | 10 |
|  | 1.953 | 28 | 0 | 30 | 60 | 85 | 100 | | 40 | 20 | 45 | | 100 | 5 | 20 | 20 | | 10 | 15 | 0 | 10 | 5 |
| 45 | 31.25 | 95 | 15 | 70 | 100 | 100 | 100 | | 100 | 100 | 100 | | 100 | 90 | 40 | 30 | | 50 | 10 | 5 | 10 | 25 |

-continued

POSTEMERGENCE

| Cmpd No. | Conc | Cttn | OlRp | Sybn | Sgbt | Ckbr | Jmwd | Lmqr | Mngy | RdRw | Velc | Spwl | WdBk | Corn | Rice | Whet | Blkg | Bnyd | GlFx | Jngr | WiOa | YlNt |
|---|---|---|---|---|---|---|---|---|---|---|---|---|---|---|---|---|---|---|---|---|---|---|
| 38 | 15.625 | 85 | 15 | 15 | 85 | 85 | 100 | | 100 | 100 | 100 | | 100 | 70 | 60 | 65 | | 15 | 80 | 5 | | 5 |
| | 7.813 | 85 | 15 | 65 | 65 | 20 | 100 | | 100 | 65 | 88 | | 100 | 40 | 15 | 20 | | 5 | 40 | 5 | | 5 |
| | 3.906 | 15 | 15 | 15 | 10 | 30 | 100 | | 80 | 88 | 35 | | 70 | 5 | 5 | 5 | | 5 | 3 | 3 | | 0 |
| | 1.953 | 65 | 15 | 5 | 10 | 20 | 100 | | 100 | 100 | 35 | | 100 | 5 | 5 | 5 | | 5 | 3 | 3 | | 0 |
| | .977 | 45 | 15 | 5 | 10 | 0 | 10 | | 20 | 15 | 40 | | 10 | 5 | 5 | 100 | | 5 | 40 | 0 | | 0 |
| | 31.25 | 88 | 20 | 20 | 25 | 100 | 100 | | 100 | 80 | 100 | | 100 | 30 | 20 | 100 | | 30 | 80 | 40 | | 20 |
| | 15.625 | 70 | 20 | 15 | 15 | 85 | 100 | | 90 | 100 | 100 | | 100 | 40 | 15 | 50 | | 20 | 60 | 30 | | 10 |
| | 7.813 | 10 | 20 | 15 | 10 | 40 | 100 | | 70 | 70 | 70 | | 100 | 20 | 10 | 10 | | 5 | 20 | 10 | | 5 |
| | 3.906 | 10 | 20 | 10 | 0 | 30 | 98 | | 80 | 20 | 50 | | 100 | 10 | 10 | 50 | | 5 | 10 | 5 | | 5 |
| | 1.953 | 0 | 20 | 0 | 20 | 0 | 85 | | 20 | 50 | 20 | | 100 | 10 | 10 | 10 | | 5 | 5 | 5 | | 5 |
| | .977 | 0 | 20 | 0 | 0 | 55 | 80 | | 60 | 20 | 50 | | 100 | 10 | 10 | 10 | | 5 | 5 | 5 | | 5 |
| 44 | 62.5 | 70 | 20 | 60 | 95 | 0 | 100 | | 100 | 60 | 70 | | 100 | 25 | 25 | 80 | | 30 | 30 | 20 | | 0 |
| | 31.25 | 75 | 5 | 15 | 85 | 5 | 100 | | 100 | 30 | 100 | | 85 | 5 | 5 | 60 | | 20 | 90 | 20 | | 20 |
| | 15.625 | 75 | 5 | 10 | 20 | 5 | 65 | | 70 | 0 | 85 | | 0 | 5 | 5 | 50 | | 10 | 50 | 10 | | 5 |
| | 7.813 | 65 | 5 | 5 | 10 | 5 | 50 | | 60 | 0 | 70 | | 0 | 0 | 5 | 10 | | 0 | 20 | 45 | | 5 |
| | 3.906 | 65 | 3 | 0 | 20 | 3 | 50 | | 10 | 0 | 30 | | 0 | 0 | 3 | 5 | | 0 | 5 | 5 | | 0 |
| | 1.953 | 20 | 10 | 0 | 30 | 2 | 20 | | 5 | 0 | 20 | | 0 | 0 | 3 | 5 | | 3 | 3 | 0 | | 0 |
| 40 | 31.25 | 80 | 0 | 45 | 100 | 98 | 100 | | 100 | 100 | 100 | | 100 | 25 | 98 | 10 | | 90 | 98 | 20 | | 0 |
| | 15.625 | 85 | 0 | 40 | 70 | 40 | 100 | | 100 | 100 | 100 | | 100 | 20 | 35 | 5 | | 0 | 40 | 25 | | 20 |
| | 7.813 | 65 | 0 | 25 | 60 | 40 | 98 | | 70 | 98 | 98 | | 85 | 20 | 20 | 5 | | 0 | 20 | 10 | | 10 |
| | 3.906 | 45 | 0 | 20 | 20 | 30 | 98 | | 60 | 50 | 100 | | 20 | 30 | 30 | 0 | | 0 | 0 | 0 | | 10 |
| | 1.953 | 35 | 0 | 30 | 30 | 20 | 50 | | 80 | 40 | 100 | | 0 | 0 | 5 | 0 | | 0 | 0 | 45 | | 0 |
| | .977 | 0 | 0 | 0 | 0 | 0 | 35 | | 40 | 0 | 40 | | 0 | 0 | 0 | 25 | 0 | 0 | 0 | 0 | 0 | 0 |
| 41 | 31.25 | 80 | 30 | 60 | 100 | 100 | 100 | 100 | 100 | 100 | 100 | 80 | 100 | 45 | 50 | 0 | 98 | 100 | 90 | 100 | 0 | 35 |
| | 15.625 | 95 | 30 | 55 | 100 | 70 | 100 | 75 | 100 | 100 | 98 | 70 | 100 | 70 | 30 | 0 | 85 | 100 | 100 | 30 | 0 | 20 |
| | 7.813 | 95 | 30 | 50 | 90 | 100 | 100 | 80 | 100 | 100 | 99 | 40 | 100 | 20 | 20 | 0 | 100 | 100 | 100 | 0 | 0 | 0 |
| | 3.906 | 85 | 0 | 25 | 0 | 75 | 100 | 80 | 70 | 100 | 100 | 40 | 90 | 0 | 20 | 0 | 75 | 100 | 100 | 0 | 0 | 0 |
| | 1.953 | 40 | 0 | 60 | 0 | 40 | 95 | 100 | 70 | 98 | 98 | 40 | 90 | 0 | 20 | 0 | 70 | 100 | 40 | 0 | 0 | 0 |
| | .977 | 30 | 0 | 35 | 0 | 25 | 100 | 100 | 70 | 40 | 40 | 100 | 60 | 50 | 20 | 0 | 80 | 85 | 0 | 0 | 25 | 30 |
| 53 | 2000 | 60 | 50 | 25 | 40 | 100 | 100 | 75 | 100 | 70 | 100 | | 100 | 45 | 30 | 10 | 0 | 100 | 75 | 80 | 0 | 0 |
| | 1000 | 55 | 35 | 25 | 40 | 70 | 100 | 80 | 100 | 20 | 20 | | 100 | 40 | 35 | 0 | 100 | 100 | 85 | 70 | 0 | 0 |
| | 500 | 30 | 35 | 25 | 40 | 60 | 100 | 80 | 98 | 20 | 0 | | 100 | 20 | 10 | 0 | 75 | 20 | 50 | 60 | 0 | 0 |
| | 250 | 0 | 0 | 0 | 0 | 20 | 90 | 100 | 70 | 0 | 0 | | 40 | 20 | 0 | 0 | 70 | 0 | 20 | 50 | 0 | 0 |
| | 125 | 0 | 0 | 0 | 0 | 20 | 100 | 100 | 70 | 0 | 0 | 100 | 40 | 20 | 0 | 0 | 35 | 0 | 20 | 50 | 0 | 0 |
| 50 | 125 | 100 | 100 | 100 | 100 | 100 | 100 | 100 | 100 | 100 | 100 | 100 | 100 | 100 | 98 | 98 | 0 | 100 | 100 | 100 | 98 | 90 |
| | 62.5 | 100 | 100 | 100 | 100 | 100 | 100 | 75 | 100 | 100 | 98 | 100 | 100 | 100 | 98 | 85 | 98 | 100 | 100 | 100 | 100 | 85 |
| | 31.25 | 100 | 98 | 98 | 100 | 70 | 100 | 80 | 100 | 100 | 99 | 100 | 100 | 99 | 99 | 40 | 100 | 100 | 100 | 100 | 40 | 60 |
| | 15.625 | 75 | 98 | 100 | 100 | 60 | 100 | 80 | 100 | 100 | 100 | 100 | 100 | 98 | 60 | 20 | 75 | 100 | 100 | 70 | 45 | 45 |
| | 7.813 | 90 | 98 | 98 | 85 | 50 | 100 | 100 | 100 | 100 | 100 | 100 | 100 | 98 | 60 | 20 | 70 | 100 | 100 | 70 | 35 | 40 |
| 50 | 15.6 | 100 | 100 | 80 | 75 | 100 | 100 | 100 | 100 | 100 | 85 | 60 | 90 | 90 | 50 | 25 | 80 | 100 | 100 | 85 | 70 | 25 |
| | 7.8 | 100 | 85 | 98 | 60 | 70 | 100 | 80 | 100 | 98 | 80 | 50 | 80 | 100 | 35 | 35 | 70 | 100 | 100 | 100 | 50 | 20 |
| | 3.9 | 85 | 75 | 50 | 60 | 50 | 100 | 80 | 100 | 40 | 40 | 40 | 90 | 98 | 30 | 20 | 80 | 85 | 100 | 70 | 40 | 10 |
| | 1.95 | 75 | 55 | 75 | 50 | 70 | 100 | 80 | 100 | 70 | 20 | 35 | 80 | 98 | 30 | 10 | 35 | 95 | 98 | 60 | 20 | 0 |
| | .975 | 55 | 10 | 85 | 40 | 25 | 90 | 80 | 100 | 20 | 20 | 0 | 80 | 75 | 35 | 10 | 0 | 40 | 80 | 40 | 10 | 0 |
| 62 | 500 | 100 | 100 | 85 | 100 | 100 | 100 | 100 | 100 | 100 | 100 | 100 | 100 | 100 | 50 | 100 | 100 | 100 | 100 | 100 | 100 | 100 |
| | 250 | 100 | 100 | 85 | 100 | 100 | 100 | 100 | 100 | 100 | 100 | 100 | 100 | 98 | 98 | 95 | 98 | 100 | 100 | 100 | 90 | 95 |
| | 125 | 100 | 100 | 70 | 100 | 100 | 100 | 98 | 100 | 100 | 100 | 100 | 100 | 75 | 80 | 50 | 40 | 100 | 100 | 100 | 45 | 90 |
| 62 | 62.5 | 100 | 100 | 65 | 100 | 100 | 100 | 98 | 100 | 100 | 100 | 100 | 100 | 75 | 80 | 40 | 40 | 100 | 100 | 100 | 45 | 70 |
| | 31.25 | 100 | 80 | 65 | 100 | 98 | 100 | 100 | 100 | 100 | 100 | 100 | 100 | 55 | 99 | 50 | 20 | 100 | 100 | 100 | 25 | 40 |

-continued

POSTEMERGENCE

| Cmpd No. | Conc | Cttn | OlRp | Sybn | Sgbt | Ckbr | Jmwd | Lmqr | Mngy | RdPw | Vclc | Spwl | WdBk | Corn | Rice | Whet | Blkg | Bnyd | GlFx | Jngr | WiOa | YlNt |
|---|---|---|---|---|---|---|---|---|---|---|---|---|---|---|---|---|---|---|---|---|---|---|
|  | 7.8 | 100 | 60 | 25 | 90 | 70 | 100 | 100 | 100 | 100 | 100 | 100 | 100 | 70 | 50 | 20 | 0 | 85 | 100 | 100 | 10 | 40 |
|  | 3.9 | 100 | 75 | 20 | 80 | 70 | 100 | 100 | 100 | 100 | 85 | 98 | 100 | 50 | 35 | 0 | 0 | 90 | 100 | 75 | 10 | 20 |
|  | 1.95 | 100 | 60 | 10 | 75 | 60 | 100 | 100 | 100 | 50 | 100 | 50 | 60 | 35 | 40 | 0 | 0 | 50 | 100 | 80 | 0 | 0 |
|  | .975 | 70 | 40 | 5 | 55 | 45 | 80 | 60 | 100 | 60 | 80 | 0 | 40 | 10 | 40 | 0 | 0 | 0 | 80 | 30 | 0 | 0 |
| 63 | 500 | 100 | 100 | 98 | 100 | 100 | 100 | 100 | 100 | 100 | 100 |  | 100 | 100 | 98 | 98 | 100 | 100 | 100 | 100 | 99 | 100 |
|  | 250 | 100 | 100 | 98 | 100 | 100 | 100 | 100 | 100 | 100 | 100 | 100 | 100 | 100 | 100 | 98 | 100 | 100 | 100 | 100 | 99 | 100 |
|  | 125 | 100 | 100 | 90 | 100 | 100 | 100 | 100 | 100 | 100 | 100 | 100 | 100 | 100 | 98 | 98 | 98 | 100 | 100 | 100 | 85 | 100 |
|  | 62.5 | 100 | 100 | 100 | 99 | 100 | 100 | 100 | 100 | 100 | 100 | 100 | 100 | 100 | 100 | 98 | 100 | 100 | 100 | 100 | 100 | 90 |
|  | 31.25 | 100 | 100 | 85 | 95 | 100 | 100 | 100 | 100 | 98 | 100 | 100 | 100 | 90 | 30 | 90 | 99 | 100 | 100 | 90 | 35 | 80 |
| 63 | 15.6 | 100 | 100 | 85 | 100 | 100 | 100 | 100 | 100 | 100 | 100 | 100 | 100 | 95 | 45 | 75 | 70 | 98 | 100 | 90 | 80 | 20 |
|  | 7.8 | 100 | 100 | 85 | 98 | 100 | 100 | 100 | 100 | 98 | 100 | 80 | 100 | 65 | 30 | 45 | 80 | 100 | 90 | 100 | 80 | 10 |
|  | 3.9 | 100 | 100 | 85 | 100 | 100 | 100 | 100 | 100 | 100 | 100 | 80 | 100 | 75 | 45 | 30 | 20 | 98 | 98 | 100 | 50 | 0 |
|  | 1.95 | 100 | 100 | 80 | 100 | 100 | 100 | 100 | 100 | 100 | 100 | 80 | 98 | 25 | 30 | 40 | 0 | 60 | 100 | 80 | 30 | 0 |
|  | .975 | 98 |  |  |  |  |  |  |  |  |  |  |  |  |  |  |  |  |  |  |  |  |

Other representative compounds of Formula A were further tested as follows:

TEST 3

Method:

Growing Medium: The growing medium for preemergence surface applied treatments is a loam soil (45% sand, 34% silt, 21% clay, 1.4% organic matter, pH 7.6). The medium for postemergence treatments is an artificial soil composed of vermiculite, sphagnum peat moss, processed bark, granite sand, and supplemental nutrients (Metro-Mix 360, W. R. Grace and Co.).

Container and Planting: All plantings are made in two plastic or galvanized pans (flats), approximately 31.5 cm long, 21.5 cm wide, and 8.0 cm deep, for each treatment type and each rate. Calculated surface area for two flats is 1.44 sq. ft. The bottoms of the flats have holes to facilitate drainage. The planting procedure starts by filling a flat two-thirds full with growing medium (approximately 5 cm deep). The medium is then leveled and tamped firm. The flats are prepared for each compound rate. Seeds of the indicator species are planted in rows parallel to the long axis of the flat, one species per half row. Species which may be used in each test are as follows:

| Name | Abbreviation |
| --- | --- |
| Rice (*Oryza sativa*) | Rice |
| Jimsonweed (*Datura stramonium*) | Jiwe |
| Cheatgrass (*Bromus secalinus*) | Chet |
| Lambsquarter (*Chenopodium album*) | Lmqr |
| Cocklebur (*Xanthium strumarium*) | Ckbr |
| Johnsongrass (*Sorghum halapense*) | Jngr |
| Cotton (*Gossypium hirsutum*) | Cttn |
| Giant Foxtail (*Setaria faberii*) | GiFt |
| Wild Oat (*Avena fatua*) | WiOa |
| Barnyardgrass (*Echinochloa crus-galli*) | Bnyd |
| Velvetleaf (*Aubutilon theophrasti*) | Vele |
| Green Foxtail (*Setaria viridis*) | GrFt |
| Corn (*Zea mays*) | Corn |
| Soybean (*Glycine max*) | Sybn |
| Wheat (*Triticum aestivum*) | Whet |
| Morningglory (Ipomoea sp.) | Mngy |
| Redroot Pigweed (*Amaranthus retroflexus*) | RdPw |
| Barley (*Hordeum vulgare*) | Brly |

The seeds are covered with approximately 1 cm of growing medium. Flats prepared for postemergence treatment are planted 8 to 11 days prior to treatment and placed in a growth chamber under artificial lighting. Environmental conditions are a 16 hour photoperiod and 24°-29° C. temperature. Preemergent test flats are planted 1 to 2 days prior to treatment.

Formulation: Each compound (3.76 mg per type of application if the high rate is to be 140 g/Ha) is dissolved in 5 mL of acetone and ethanol (1:1) containing a small amount of Toximul-R and S (1.4:1) surfactants. The solution is diluted with deionized water to 50 mL. After dilution with deionized water, concentrations in the stock solution are as follows:

| Test Compound | 0.0075% |
| --- | --- |
| Acetone | 5.0% |
| Ethanol | 5.0% |
| Toximul R and S (combined) | 0.2% |
| Deionized water | 89.8% |
| | 100.0% |

Treatment: The formulated compounds are applied with a DeVilbiss ® compressed air sprayer operated at 2-4 psi. The formulation is applied uniformly over the soil surface (preemergence, surface applied) or over the foliage of plants (postemergence). Each flat receives 12.5 mL of the formulation, equal to 200 gpa. Each compound generally is applied at four to six rates. The rates of application generally are 140, 70, 35, 17.5, 8.75, or 4.375 g/Ha, although these rates may be altered to exclude the high or low rates. Preemergence flats are watered in shortly after treatment. Both preemergence and postemergence treated flats are moved to a greenhouse equipped with growing conditions supplied above. Postemergence applications are sub-irrigated for the duration of the experiment. Preemergence applications are top-watered for nine days after treatment, then sub-irrigated for the duration of the experiment.

Evaluation (Preemergent): Assessment of weed control and crop injury is made three weeks after application of the test chemicals. Plant injury is visually assessed on a scale of 0 to 10%, with 0% equal to no injury and 10% equal to complete kill. A blank indicates no evaluation was performed. Each species per treatment is also evaluated for type of injury according to the scale listed in Test 1.

Evaluation (Postemergent): Assessment of weed control and crop injury is made two weeks after application of the test chemicals. Plant injury is visually assessed on a scale of 0 to 10%, with 0% equal to no injury and 10% equal to complete kill. A blank indicates no evaluation was performed. Each species per treatment is also evaluated for type of injury according to the scale listed in Test 1.

The results obtained were as follows:

PREEMERGENCE

| Cmpd No. | Conc (g/Ha) | Rice | Jmwd | Chet | Lmqr | Ckbr | Jngr | Cttn | GiFx | WiOa | Bnyd | Vele | GrFx | Corn | Sybn | Whet | Mngy | RdPw | Brly |
|---|---|---|---|---|---|---|---|---|---|---|---|---|---|---|---|---|---|---|
| 29 | 140 | 2B | 9BS | | | 0 | | 3B | 9BS | 2S | 7CSF | 7.5BSC | | 0 | 0 | 1B | 0 | 10 | 0 |
| | 70 | 1B | 7BS | | | 0 | | 3B | 5S | 2S | 2C | 8BSC | | 0 | 0 | 0 | 0 | 10 | 0 |
| | 35 | 0 | 7BS | | | 0 | | 2B | 0 | 0 | 0 | 3CB | | 0 | 0 | 0 | 0 | 10 | 0 |
| | 17.5 | 0 | 3SB | | | 0 | | 1B | 0 | 0 | 0 | 3C | | 0 | 0 | 0 | 0 | 10 | 0 |
| | 8.75 | 0 | 2S | | | 0 | | 1B | 0 | 0 | 0 | 3C | | 0 | 0 | 0 | 0 | 5RS | 0 |
| | 4.4 | 0 | 0 | | | 0 | | 1B | 0 | 0 | 0 | 3C | | 0 | 0 | 0 | 0 | 4RS | 0 |
| 30 | 140 | 0 | 10 | | | 0 | | 2.5B | 10 | 5SF | 4FS | 3.5CS | | 0 | 0 | 0 | 0 | 10 | 0 |
| | 70 | 0 | 8.5RSB | | | 0 | | 2B | 9.9RS | 3SF | 3F | 3CS | | 0 | 0 | 0 | 0 | 10 | 0 |
| | 35 | 0 | 7RSB | | | 0 | | 2B | 6RS | 2S | 2F | 3C | | 0 | 0 | 0 | 0 | 10 | 0 |
| | 17.5 | 0 | 6BS | | | 0 | | 1B | 4RS | 0 | 0 | 2C | | 0 | 0 | 0 | 0 | 9.5RS | 0 |
| | 8.75 | 0 | 0 | | | 0 | | 2B | 0 | 0 | 0 | 2C | | 0 | 0 | 0 | 0 | 6RS | 0 |
| | 4.4 | 0 | 0 | | | 0 | | 2B | 0 | 0 | 0 | 2C | | 0 | 0 | 0 | 0 | 0 | 0 |
| 31 | 140 | 2B | 10 | | | 0 | | 2.5BS | 9.8RS | 4S | 8.5SF | 9.8RSC | | 3F | 2S | 0 | 2S | 10 | 2S |
| | 70 | 1B | 9.8RSB | | | 0 | | 2B | 9.5RS | 3S | 7SF | 9.8RSC | | 2F | 0 | 0 | 0 | 10 | 1 |
| | 35 | 0 | 5S | | | 0 | | 1.5B | 4S | 0 | 2SF | 3CS | | 0 | 0 | 0 | 0 | 10 | 0 |
| | 17.5 | 0 | 4S | | | 0 | | 1B | 2S | 0 | 0 | 3C | | 0 | 0 | 0 | 0 | 9.5RS | 0 |
| | 8.75 | 0 | 0 | | | 0 | | 1B | 0 | 0 | 0 | 2C | | 0 | 0 | 0 | 0 | 0 | 0 |
| | 4.4 | 0 | 0 | | | 0 | | 1B | 0 | 0 | 0 | 2C | | 0 | 0 | 0 | 0 | 0 | 0 |
| 32 | 140 | 0 | 0 | | | 0 | | 1B | 0 | 0 | 0 | 2C | | 0 | 0 | 0 | 0 | 7RS | 0 |
| | 70 | 0 | 0 | | | 0 | | 1B | 0 | 0 | 0 | 2C | | 0 | 0 | 0 | 0 | 4S | 0 |
| | 35 | 0 | 0 | | | 0 | | 1B | 0 | 0 | 0 | 2C | | 0 | 0 | 0 | 0 | 2S | 0 |
| | 17.5 | 0 | 0 | | | 0 | | 1B | 0 | 0 | 0 | 2C | | 0 | 0 | 0 | 0 | 0 | 0 |
| | 8.75 | 0 | 0 | | | 0 | | 1B | 0 | 0 | 0 | 2C | | 0 | 0 | 0 | 0 | 0 | 0 |
| | 4.4 | 0 | 0 | | | 0 | | 0 | 0 | 0 | 0 | 2C | | 0 | 0 | 0 | 0 | 0 | 0 |
| 35 | 140 | 2 | 10 | 2 | 10 | 0 | 9 | 0 | 9 | 1 | 6 | 9 | 10 | 3 | 0 | 0 | 2 | | |
| | 70 | 2 | 4 | 2 | 10 | 0 | 7 | 0 | 9 | 0 | 4 | 9.5 | 8 | 1 | 2S | 0 | 0 | | |
| | 35 | 1 | 3 | 0 | 9.7 | 0 | 2 | 0 | 3 | 0 | 2 | 3 | 8 | 0 | 0 | 0 | 0 | | |
| 36 | 140 | 1 | 10 | 6 | 10 | 0 | 6 | 0 | 8 | 1 | 0 | 10 | 5 | 2 | 0 | 0 | 0 | | |
| | 70 | 0 | 10 | 5 | 10 | 0 | 7 | 0 | 5 | 0 | 9.5 | 6 | 10 | 3 | 1 | 0 | 0 | | |
| | 35 | 1 | 5 | 6 | 10 | 0 | 1 | 0 | 5 | 0 | 6 | 10 | 9 | 0 | 0 | 0 | 2 | | |
| 37 | 140 | 1 | 3 | 0 | 10 | 0 | 0 | 0 | 6 | 2 | 2 | 6 | 9.5 | 0 | 0 | 0 | 0 | | |
| | 70 | 0 | 9 | 2 | 10 | 0 | 7 | 0 | 6 | 2 | 5 | 0 | 10 | 0 | 0 | 1 | 6 | | |
| | 35 | 2 | 9.5 | 0 | 9.7 | 0 | 5 | 0 | 10 | 1 | 2 | 9.5 | 10 | 1 | 1 | 0 | 4 | | |
| 25 | 140 | 0 | 0 | 0 | 7 | 0 | 2 | 0 | 5 | 2 | 2 | 8 | 8 | 0 | 0 | 0 | 0 | | |
| | 70 | 0 | 0 | 0 | 5 | 0 | 0 | 0 | 2 | 1 | 2 | 3 | 2 | 0 | 0 | 0 | 0 | | |
| | 35 | 1 | 0 | 0 | 4 | 0 | 0 | 0 | 0 | 0 | 0 | 2 | 0 | 0 | 0 | 0 | 0 | | |
| 39 | 140 | 2 | 10 | 4 | 10 | 0 | 8 | 0 | 10 | 6 | 7 | 0 | 0 | 0 | 0 | 0 | 3 | | |
| | 70 | 1 | 10 | 2 | 10 | 0 | 7 | 0 | 8 | 2 | 5 | 10 | 2 | 5 | 0 | 0 | 2 | | |
| | 35 | 2 | 2 | 0 | 0 | 0 | 2 | 0 | 6 | 0 | 2 | 5 | 10 | 1 | 0 | 0 | 1 | | |
| | 17.5 | 2 | 0 | 0 | 0 | 0 | 2 | 0 | 5 | 0 | 0 | 8 | 10 | 0 | 0 | 0 | 0 | | |
| | | | | | | | | | | | | | 6 | | | | | | |

| Cmpd No. | Conc (g/Ha) | Rice | Jmwd | Chet | Lmqr | Ckbr | Jngr | Cttn | GlFx | WlOa | Bnyd | Vcle | GrFx | Corn | Sybn | Whet | Mngy | RdPw | Brly |
|---|---|---|---|---|---|---|---|---|---|---|---|---|---|---|---|---|---|---|
| 29 | 140 | 4CBS | 10 | | | 3BS | | 10 | 7BS | 2BS | 2B | 8BS | | 4BF | 8BSF | 3B | 10 | 7BS | 3B |
| | 70 | 4CBS | 10 | | | 2BS | | 10 | 3BS | 1B | 1B | 7BS | | 4BF | 6BSF | 2B | 10 | 6BS | 3B |
| | 35 | 3CBS | 10 | | | 2BS | | 9BS | 3BS | 0 | 1B | 7BS | | 3BF | 5BSF | 2B | 10 | 6BS | 2B |
| | 17.5 | 2C | 10 | | | 2B | | 5BS | 3BS | 0 | 0 | 4BS | | 2BF | 5BSF | 0 | 6BS | 4BS | 2B |
| | 8.75 | 0 | 7BSE | | | 2B | | 5BS | 2BS | 0 | 0 | 2BS | | 3BF | 4BSF | 0 | 5BS | 3BS | 2B |
| | 4.4 | 0 | 3BSE | | | 2B | | 2B | 2BS | 0 | 0 | 2B | | 2BF | 3BSF | 3.5B | 4BS | 2B | 0 |
| 30 | 140 | 5CBS | 10 | | | 8BS | | 10 | 9.7BS | 4BS | 6BS | 6BS | | 7BF | 9BSF | 3B | 10 | 9.5BS | 4.5BS |
| | 70 | 6CBS | 10 | | | 7BS | | 9.5BS | 9.9BS | 4BS | 5BS | 3BS | | 6BF | 8BSF | 3B | 10 | 9.7BS | 4BS |
| | 35 | 4CBS | 10 | | | 6BS | | 8BS | 8BS | 3BS | 2B | 4BS | | 4B | 7.5BSF | 2B | 9.5BS | 4BS | 4BS |
| | 17.5 | 3CBS | 10 | | | 6BS | | 7BS | 4BS | 2B | 1B | 2BS | | 3.5B | 7BSF | 1B | 9BS | 4BS | 3.5BS |
| | 8.75 | 2BC | 10 | | | 5BS | | 3BS | 5BS | 1B | 0 | 2BS | | 3B | 7BSF | 1B | 9BS | 3BS | 3B |
| | 4.4 | 1B | 10 | | | 7BS | | 3B | 4BS | 1B | 0 | 0BS | | 3B | 4BSF | 1B | 9BS | 2BS | 2B |
| 31 | 140 | 7CBS | 10 | | | 7BS | | 10 | 10 | 4BS | 5BS | 10 | | 7 | 10 | 5BS | 10 | 10 | 5BS |
| | 70 | 6CBS | 10 | | | 7BS | | 10 | 9BS | 4BS | 4BS | 10 | | 6F | 9BS | 4B | 10 | 9BS | 4BS |
| | 35 | 6CBS | 10 | | | 5BS | | 10 | 7.5BS | 2B | 3B | 10 | | 5F | 9BS | 4B | 10 | 7BS | 4BS |
| | 17.5 | 5CBS | 10 | | | 6BS | | 10 | 6BS | 1 | 2B | 9.5BS | | 5B | 7.5BSF | 3B | 9.5BS | 6BS | 3B |
| | 8.75 | 3CB | 10 | | | 3B | | 8BS | 2B | 1B | 2B | 5BS | | 3B | 7B | 2B | 9BS | 5BS | 2.5B |
| | 4.4 | 2CB | 9BS | | | | | 7.5BS | 2B | 1B | 2BS | 3B | | 2.5B | 7B | 1B | 9BS | 5BS | 2B |
| 32 | 140 | 4CB | 10 | | | 3B | | 10 | 3BS | 2B | 0 | 9.8BS | | 4B | 6BF | 2B | 9BS | 9.8BS | 2B |
| | 70 | 3CB | 10 | | | 2B | | 10 | 2B | 1B | 0 | 7BS | | 3B | 5BF | 1B | 5BS | 6BS | 2B |
| | 35 | 3CB | 9BSF | | | 2BC | | 9.5BS | 2B | 1B | 0 | 4BS | | 3B | 4.5BF | 1B | 5BS | 3B | 2B |
| | 17.5 | 2C | 5BSF | | | 0 | | 5BS | 3B | 1B | 0 | 3BS | | 2.5 | 4BF | 0 | 4BS | 3B | 1B |
| | 8.75 | 2C | 4BSF | | | 0 | | 4BS | 2B | 0 | 0 | 2BS | | 2B | 4BF | 0 | 3BS | 2B | 1B |
| | 4.4 | 4CBS | 0 | | | 0 | | 3BS | 1B | 0 | 0 | 1F | | 2B | 3B | 0 | 2BS | | |
| 35 | 28.4 | 2 | 10 | 2 | 10 | | 5 | 10 | 8 | 2 | 2 | 7 | | 5 | 6 | 3 | 8 | | |
| | 14.2 | 2 | 10 | 1 | 9.5 | | 3 | 10 | 6 | 1 | 1 | 7 | 5 | 4 | 6 | 1 | 5 | | |
| | 7.1 | 2 | 10 | 0 | 9 | | 2 | 8 | 5 | 0 | 0 | 5 | 3 | 2 | 3 | 0 | 4 | | |
| | 3.5 | 1 | 10 | 2 | 8 | | 1 | 8 | 9 | 0 | 2 | 5 | | 5 | 6 | 2 | 3 | | |
| 36 | 28.4 | 3 | 10 | 1 | 10 | | 4 | 10 | 9 | 2 | 1 | 9.5 | 6 | 6 | 6 | 0 | 7 | | |
| | 14.2 | 3 | 10 | 0 | 9 | | 4 | 10 | 8 | 0 | 0 | 7 | 6 | 4 | 4 | 2 | 4 | | |
| | 7.1 | 2 | 10 | 2 | 9 | | 3 | 10 | 4 | 2 | 1 | 5 | 4 | 3 | 3 | 2 | 5 | | |
| | 3.5 | 2 | 10 | 1 | 9 | | 2 | 8 | 8 | 0 | 0 | 3 | 3 | 4 | 3 | 1 | 3 | | |
| 37 | 28.4 | 2 | 10 | 0 | 9.5 | | 5 | 10 | 7 | 2 | 2 | 7 | 5 | 5 | 7 | 2 | 5 | | |
| | 14.2 | 1 | 10 | 1 | 9.5 | | 5 | 10 | 8 | 2 | 2 | 7 | 5 | 5 | 6 | 1 | 5 | | |
| | 7.1 | 1 | 10 | 0 | 9 | | 2 | 8 | 4 | 0 | 1 | 5 | 4 | 3 | 4 | 2 | 4 | | |
| | 3.5 | 1 | 10 | 0 | 9 | | 1 | 4 | 6 | 0 | 0 | 7 | 5 | 3 | 4 | 0 | 3 | | |
| 25 | 70 | 2 | 10 | 0 | 8 | 3 | 3 | 8 | 3 | 0 | 0 | 5 | 3 | 3 | 6 | 1 | 6 | | |
| | 35 | 2 | 10 | 0 | 8 | | 2 | 6 | 2 | 2.5 | 0 | 2 | 2 | 3 | 4 | 0 | 3 | | |
| | 17.5 | 0 | 9 | 0 | 4 | | 0 | 4 | 1 | 2 | 0 | 0 | 0 | 1 | 3 | 3 | 3 | | |
| | 8.75 | 5 | 8 | 2 | 10 | | 8 | 5 | 9 | 2 | 2 | 10 | 7 | 9 | 3 | 0 | 10 | | |
| 39 | 70 | 4 | 10 | 1 | 10 | | 4 | 10 | 9 | 1 | 1 | 10 | 3 | 8 | 8 | 3 | 10 | | |
| | 35 | 2 | 10 | 0 | 10 | | 3 | 10 | 8 | 0 | 0 | 10 | 2 | 4 | 7 | 2 | 10 | | |
| | 17.5 | 2 | 10 | 1 | 10 | | 3 | 10 | 8 | 0 | 0 | 10 | 2 | 5 | 7 | 1 | 9 | | |
| | 8.75 | 1 | 10 | | | | | | | | | | | | | | | | |

POSTEMERGENCE

As the data presented in the above tables indicate, the phenylimidazolone derivatives of the present invention possess useful broad and selective herbicidal activity, and therefore, are of particular value in the control and elimination of undesired vegetation.

The quantity of a compound of the present invention to be applied in order to exhibit a satisfactory herbicidal effect may vary over a wide range, and depends on a variety of factors, such as, for example, the hardiness of a particular vegetative species, extent of vegetation, climatic conditions, soil conditions, method of application, and the like. Typically, a herbicidally-effective amount will generally be from about 0.001 to about 15.0 pounds of compound per acre of soil (about 0.001 to about 16.8 kg/ha).

For all such uses, unmodified preparations of the compounds of the present invention may be utilized. However, the present invention also embodies the use of a herbicidally-effective amount of the compounds of the present invention in composition form with an inert material known in the art as an agricultural adjuvant or carrier in solid or liquid form. Such adjuvants or carriers must not be phytotoxic to valuable crops, particularly at the concentration employed in applying the composition when attempting selective weed control in the presence of crops. If weed control is desired in the absence of crops, it is generally sufficient to employ adjuvants or carriers which do not leave a persistent phytotoxic residue. Such compositions will generally contain from about 0.001 to about two percent by weight of active compound. The particular amount will of course be determined by the type of composition desired. The inert portions of herbicidal formulations and methods of manufacture of them are well known and conventional in the agricultural chemicals art. Similarly, the methods of applying the herbicidal formulations are well known to the ordinarily skilled artisan. Only a brief explanation of such formulations and methods of application will therefore be given.

Thus for example, a compound of the present invention can be dispersed on a finely divided solid and employed therein as a dust. The dust formulation usually will contain from about 0.001 to about 5 percent by weight of the compound. Dust formulations are prepared by intimately mixing and finely grinding the compound with an agronomically acceptable carrier, such as, for example, clay, talc, diatomaceous earth, silica, and the like.

A convenient formulation consists of the compound in a composition to be applied by spraying as a water dispersion or emulsion containing from about 0.001 percent to about 5 percent by weight of the compound. Such water dispersible or emulsifiable composition may be either a solid, for example, a wettable powder, or a liquid, for example, an emulsifiable concentrate or an aqueous suspension.

A typical wettable powder formulation comprises an intimate powder mixture of about 5 percent to about 90 percent by weight of the compound, about 0.5 percent to about 10 percent by weight of a wetting agent, such as, for example, a long chain alcohol, petroleum sulfonates, acid sulfates and derivatives, sulfonated aromatic derivatives, esters of fatty acids, and clays.

A typical emulsifiable concentrate comprises from about 0.01 pounds to about 4 pounds of the compound per gallon of liquid, dissolved in a mixture of organic solvents and emulsifiers. Useful solvents include, for example, aromatics, especially xylenes, and hydrophyllic solvents such as higher alcohols, glycols, such as ethylene glycol, and hydroxy ethers, such as 2-ethoxyethanol. Suitable emulsifiers are chosen from the same types used for wettable powders, and are used at similar weight percentages.

Solid, granular compositions are convenient for the application of the compounds to the soil. Granules comprise a compound dispersed on an inert granular agronomic carrier, such as, for example, coarsely ground clay, of from about 0.1 mm to about 3 mm particle size. The compound is most conveniently applied to the clay by dissolving it in a solvent and applying the solution to the sized clay in an appropriate solids mixer.

The formulated compounds of the present invention may be applied by any of several methods known in the art. Generally, the formulated composition will be surface applied as an aqueous spray. Such applications can be carried out by conventional ground equipment, or if desired, the sprays can be aerially applied. Soil incorporation of such surface applied compounds is accomplished by natural leaching, and is of course, facilitated by natural rainfall and melting snow. If desired, the compounds may be incorporated into the soil by conventional tillage means.

When desired, the compounds of the present invention or compositions containing the same, can be advantageously employed in combination with one or more additional pesticidal compounds. Such additional pesticidal compounds may include insecticides, nematocides, arthropodicides, herbicides, fungicides, bacteriocides, and the like, that are compatible with the compounds of the present invention in a medium selected for application, and not antagonistic to the activity of the compounds of the present invention. Typically, such formulation will contain from about 0.01 percent to about 99 percent by weight of a compound of the present invention. Such formulations will generally take the form of a tank mix or the like.

What is claimed is:

1. A compound of the formula

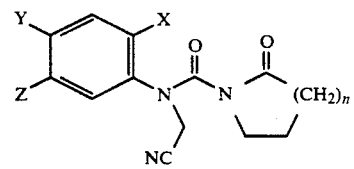

wherein
- n is an integer from 1 to 4,
- X is —H or halogen,
- Y is —H, halogen, —CN, Alk, —CF$_3$, or —OCF$_3$;
- Z is —H, halogen —OH, Alk, aryloxy, C$_{16}$ acyl, —NH$_2$, —NO$_2$, —NHSO$_2$CH$_3$, —N(SO$_2$CH$_3$)$_2$—NACOCH$_3$, or B; or Y and Z may together form a saturated, partially saturated, or unsaturated three to seven member carbon ring, wherein each carbon may be independently replaced with N, O, or S, and the ring may be substituted at any position independently with one or more Alk, —O—Alk, =O, or C$_{1-6}$ acyl groups;
- Alk is a straight, branched, or cyclic saturated or unsaturated C$_{1-6}$ hydrocarbon group; and
- B is —O—Alk, wherein each carbon may be independently replaced with one or more O or S groups, and optionally substituted with one or more halogen or C$_{1-6}$ acyl groups.

* * * * *

UNITED STATES PATENT AND TRADEMARK OFFICE
CERTIFICATE OF CORRECTION

PATENT NO. : 5,153,316
DATED : October 6, 1992
INVENTOR(S) : Michael P. Lynch It is certified that error appears in the above-identified patent and that said Letters Patent is hereby corrected as shown below:

On the title page: Item [75]

Please amend listed inventors as follows:

Delete "Gary D. Crouse, 1088 N. Shortridge Rd., Indianapolis, Ind. 46219; Michael P. Lynch, 1910 Ridge Dr., Greenfield, Ind. 46140; Jeffery D. Webster, 4444 W. Bittner Ln.; John P. Wright, 4029 S. 700 W., both of New Palestine, Ind. 46163"; and insert therefor -- Michael P. Lynch, 1910 Ridge Dr., Greenfield, Ind. 46140 --.

Please amend the specifications as follows:

On column 70, line 53, delete "$C_{16}$ acyl"; and insert therfor -- $C_{1-6}$ acyl --.

Please amend the specifications as follows:

On column 70, lines 54 and 55, delete "$-N(SO_2CH_3)_2-NACOCH_3$"; and insert therfor -- $-N(SO_2CH_3)_2-NHCOCH_3$ --.

Signed and Sealed this

Seventh Day of December, 1993

Attest:

BRUCE LEHMAN

Attesting Officer

Commissioner of Patents and Trademarks